(12) United States Patent
Fischer et al.

(10) Patent No.: US 9,414,595 B2
(45) Date of Patent: Aug. 16, 2016

(54) USE OF ANTHRANILIC ACID DIAMIDE DERIVATIVES FOR PEST CONTROL IN TRANSGENIC CROPS

(71) Applicants: BAYER CROPSCIENCE AG, Monheim (DE); BAYER INTELLECTUAL PROPERTY GMBH, Monheim (DE)

(72) Inventors: Rüdiger Fischer, Pulheim (DE); Heike Hungenberg, Langenfeld (DE); Bill Striegel, Cary, NC (US); Steven Riniker, Seffner, FL (US)

(73) Assignees: Bayer CropScience AG, Monheim (DE); Bayer Intellectual Property GmbH, Monheim am Rhein (DE)

( * ) Notice: Subject to any disclaimer, the term of this patent is extended or adjusted under 35 U.S.C. 154(b) by 0 days.

(21) Appl. No.: 14/366,068

(22) PCT Filed: Dec. 17, 2012

(86) PCT No.: PCT/EP2012/075844
§ 371 (c)(1),
(2) Date: Jun. 17, 2014

(87) PCT Pub. No.: WO2013/092519
PCT Pub. Date: Jun. 27, 2013

(65) Prior Publication Data
US 2014/0329676 A1    Nov. 6, 2014

Related U.S. Application Data

(60) Provisional application No. 61/577,233, filed on Dec. 19, 2011.

(51) Int. Cl.
*A01N 43/713* (2006.01)
*A01N 43/56* (2006.01)
*A01N 25/00* (2006.01)

(52) U.S. Cl.
CPC .............. *A01N 43/713* (2013.01); *A01N 43/56* (2013.01)

(58) Field of Classification Search
CPC .. A01N 43/713; A01N 25/00; A01N 2300/00
See application file for complete search history.

(56) References Cited

U.S. PATENT DOCUMENTS

| 8,324,390 | B2 | 12/2012 | Fischer et al. | |
| 2010/0256195 | A1* | 10/2010 | Fischer et al. | 514/341 |
| 2011/0311503 | A1 | 12/2011 | Funke et al. | |
| 2012/0010249 | A1 | 1/2012 | Fischer et al. | |
| 2013/0324560 | A1 | 12/2013 | Alig et al. | |

FOREIGN PATENT DOCUMENTS

| WO | 0170671 A2 | 9/2001 |
| WO | 03015518 A1 | 2/2003 |
| WO | 03015519 A1 | 2/2003 |
| WO | 03016282 A2 | 2/2003 |
| WO | 03016283 A1 | 2/2003 |
| WO | 03016284 A1 | 2/2003 |
| WO | 03024222 A1 | 3/2003 |
| WO | 03027099 A1 | 4/2003 |
| WO | 03062226 A1 | 7/2003 |
| WO | 2004027042 A2 | 4/2004 |
| WO | 2004033468 A1 | 4/2004 |
| WO | 2004046129 A1 | 6/2004 |
| WO | 2004067528 A1 | 8/2004 |
| WO | 2005077934 A1 | 8/2005 |
| WO | 2005085234 A2 | 9/2005 |
| WO | 2005118552 A1 | 12/2005 |
| WO | 2006000336 A2 | 1/2006 |
| WO | 2006023783 A1 | 3/2006 |
| WO | 2006040113 A1 | 4/2006 |
| WO | 2006111341 A1 | 10/2006 |
| WO | 2007006670 A1 | 1/2007 |
| WO | 2007020877 A1 | 2/2007 |
| WO | 2007024833 A1 | 3/2007 |
| WO | 2007144100 A1 | 12/2007 |
| WO | 2010069502 A2 | 6/2010 |
| WO | 2011128329 A1 | 10/2011 |
| WO | 2011157651 A1 | 12/2011 |
| WO | 2011157778 A1 | 12/2011 |

OTHER PUBLICATIONS

International Search Report received in PCT/EP2012/075844, mailed Mar. 6, 2013.

* cited by examiner

*Primary Examiner* — Kevin S Orwig
*Assistant Examiner* — Barbara Frazier
(74) *Attorney, Agent, or Firm* — McBee Moore Woodward Vanik, IP LLC

(57) ABSTRACT

The present invention relates to the use of anthranilic acid diamide derivatives with heteroaromatic and heterocyclic substituents of formula (I)

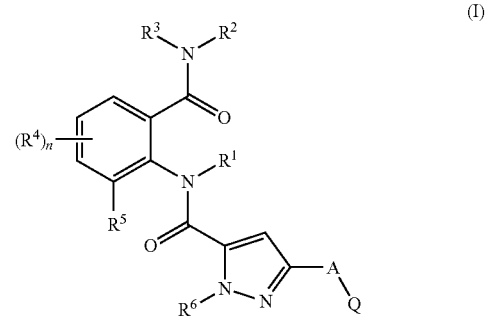

wherein $R^1$, $R^2$, $R^3$, $R^4$, $R^5$, $R^6$, n, A, Q have the meanings as given in the description—for controlling animal pests, such as insects and/or unwanted acarids and/or nematodes in transgenic crops and to methods particularly useful for controlling insects, and/or acarids and/or nematodes and/or increasing crop yield in those crops.

9 Claims, No Drawings

USE OF ANTHRANILIC ACID DIAMIDE DERIVATIVES FOR PEST CONTROL IN TRANSGENIC CROPS

CROSS REFERENCE TO RELATED APPLICATIONS

This application is a §371 National Stage Application of PCT/EP2012/075844, filed Dec. 17, 2012, which claims priority to U.S. Provisional Application 61/577,233, filed Dec. 19, 2011.

BACKGROUND

1. Field of the Invention

The present invention relates to the use of anthranilic acid diamide derivatives for controlling animal pests, such as insects and/or unwanted acarids and/or nematodes in transgenic crops and to methods particularly useful for controlling insects, and/or acarids and/or nematodes and/or increasing crop yield in those crops.

2. Description of Related Art

It is already known that certain anthranilamides (e.g. WO 01/70671, WO 03/015519, WO 03/016284, WO 03/015518, WO 03/024222, WO 03/016282, WO 03/016283, WO 03/062226, WO 03/027099, WO 04/027042, WO 04/033468, WO 2004/046129, WO 2004/067528, WO 2005/118552, WO 2005/077934, WO 2005/085234, WO 2006/023783, WO 2006/000336, WO 2006/040113, WO 2006/111341, WO 2007/006670, WO 2007/024833, WO 2007/020877) are useful for combating harmful pests which occur in agriculture.

However, environmental and economic requirements imposed in modern-day crop protection agents are continually increasing. This is particularly true with regard to the spectrum of action, toxicity, selectivity, application rate, and formation of residues. Additionally, when applying agrochemicals, there are always the problems with resistances. Thus, there is a constant need for developing new, alternative methods which in some areas at least help to fulfil the above-mentioned requirements. Also, as concerns regarding a possible impact of agrochemicals on the environment and the health of humans and animals are growing in the public opinion, efforts have to be made to reduce the amount of agrochemicals applied.

The inventors now surprisingly found that specific anthranilic diamide derivatives can advantageously be used for controlling harmful pests, such as insects and/or acarides and/or nematodes on selected transgenic crops and thus satisfying above mentioned needs. The inventors even found that a synergistic activity increase occurs by applying selected anthranilic diamide derivatives on selected transgenic crops and that crop yield on those crops is increased.

SUMMARY

Thus, the invention is directed to the use of anthranilic acid diamide derivatives with heteroaromatic and heterocyclic substituents of formula (I)

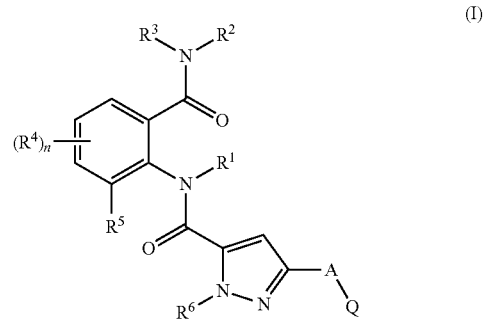

in which $R^1$ represents hydrogen, amino or hydroxyl or represents $C_1$-$C_6$-alkyl, $C_2$-$C_6$-alkenyl, $C_2$-$C_6$-alkynyl or $C_3$-$C_6$-cycloalkyl each of which is unsubstituted or substituted one or more times by identical or different substituents selectable independently of one another from halogen, cyano, nitro, hydroxyl, $C_1$-$C_4$-alkoxy, $C_1$-$C_4$-alkylthio, $C_1$-$C_4$-alkylsulphinyl, $C_1$-$C_4$-alkylsulphonyl, ($C_1$-$C_4$-alkoxy)carbonyl, $C_1$-$C_4$-alkylamino, di($C_1$-$C_4$-alkyl)amino, $C_3$-$C_6$-cycloalkylamino or ($C_1$-$C_4$-alkyl)$C_3$-$C_6$-cycloalkylamino, $R^2$ represents hydrogen, $C_1$-$C_6$-alkyl, $C_2$-$C_6$-alkenyl, $C_2$-$C_6$-alkynyl, $C_3$-$C_6$-cycloalkyl, $C_1$-$C_4$-alkoxy, $C_1$-$C_4$-alkylamino, di($C_1$-$C_4$-alkyl)amino, $C_3$-$C_6$-cycloalkylamino, $C_2$-$C_6$alkoxycarbonyl or $C_2$-$C_6$-alkylcarbonyl, $R^3$ represents hydrogen or represents $C_1$-$C_6$-alkyl, $C_1$-$C_6$-alkoxy, $C_2$-$C_6$-alkenyl, $C_2$-$C_6$-alkynyl each of which is optionally substituted one or more times by identical or different substituents selectable independently of one another from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl or $C_3$-$C_6$-trialkylsilyl, $R^3$ further represents $C_1$-$C_6$-alkyl, $C_1$-$C_6$-alkoxy, $C_2$-$C_6$-alkenyl, $C_2$-$C_6$-alkynyl each of which is optionally substituted one or more times by identical or different substituents selectable independently of one another from amino, $C_3$-$C_6$-cycloalkylamino or a 5- or 6-membered heteroaromatic ring, $R^3$ likewise further represents $C_3$-$C_{12}$-cycloalkyl, $C_3$-$C_{12}$-cycloalkyl-$C_1$-$C_6$-alkyl and $C_4$-$C_{12}$-bicycloalkyl, the substituents being selectable independently of one another from halogen, cyano, nitro, hydroxyl, amino, $C_1$-$C_6$-alkyl, $C_3$-$C_6$-cycloalkyl, $C_3$-$C_6$-cycloalkylamino, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl, $C_3$-$C_6$-trialkylsilyl or a 5- or 6-membered heteroaromatic ring, $R^2$ and $R^3$ can be joined to one another via two to six carbon atoms and form a ring which where appropriate additionally contains a further nitrogen, sulphur or oxygen atom and where appropriate may be substituted one to four times by $C_1$-$C_2$-alkyl, halogen, cyano, amino or $C_1$-$C_2$-alkoxy, $R^2$ and $R^3$ further together represent =$S(C_1-C_4$-alkyl$)_2$ or =$S(O)(C_1-C_4$-alkyl$)_2$, $R^4$ represents hydrogen, halogen, cyano, nitro, $C_1-C_4$-alkyl, $C_1-C_4$-haloalkyl, $C_2-C_6$-alkenyl, $C_2-C_6$-haloalkenyl, $C_2-C_6$-alkynyl, $C_1-C_4$-alkoxy, $C_1-C_4$-haloalkoxy, $SF_5$, $C_1-C_4$-alkylthio, $C_1-C_4$-alkylsulphinyl, $C_1-C_4$-alkylsulphonyl, $C_1-C_4$-haloalkylthio, $C_1-C_4$-haloalkylsulphinyl, $C_1-C_4$-haloalkylsulphonyl, $C_1-C_4$-alkylamino, di($C_1-C_4$-alkyl)amino, $C_3-C_6$-cycloalkylamino, ($C_1-C_4$-alkoxy)imino, ($C_1-C_4$-alkyl)($C_1-C_4$-alkoxy)imino, ($C_1-C_4$-haloalkyl)($C_1-C_4$-alkoxy)imino or $C_3-C_6$-trialkylsilyl, or two $R^4$s, via adjacent carbon atoms, form a ring which represents —(CH$_2$)$_3$—, —(CH$_2$)$_4$—, —(CH$_2$)$_5$—, —(CH=CH—)$_2$—, —OCH$_2$O—, —O(CH$_2$)$_2$O—, —OCF$_2$O—, —(CF$_2$)$_2$O—, —O(CF$_2$)$_2$O—, —(CH=CH—CH=N)— or —(CH=CH—N=CH)—, two $R^4$s further, via adjacent carbon atoms, form the following fused rings, which where appropriate are substituted one or more times by identical or different substituents selectable independently of one another from hydrogen, $C_1-C_6$-alkyl, $C_3-C_6$-cycloalkyl, $C_1-C_6$-haloalkyl, $C_3-C_6$-halocycloalkyl, halogen, $C_1-C_6$-alkoxy, $C_1-C_4$-alkylthio ($C_1-C_6$-alkyl), $C_1-C_4$-alkylsulphinyl($C_1-C_6$-alkyl), $C_1-C_4$-alkylsulphonyl($C_1-C_6$-alkyl), $C_1-C_4$-alkylamino, di($C_1-C_4$-alkyl)amino or $C_3-C_6$-cycloalkylamino,

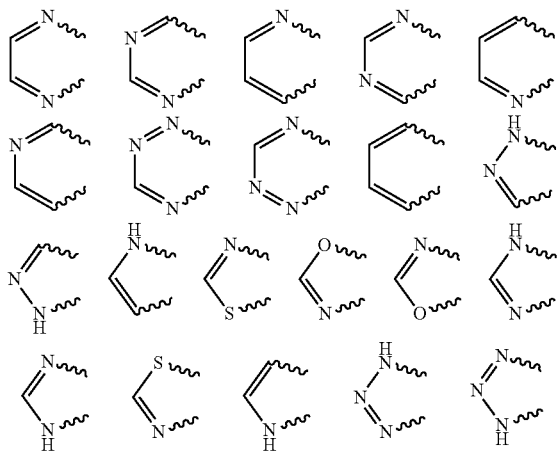

n represents 0 to 3, $R^5$ represents $C_1-C_6$-alkyl, $C_3-C_6$-cycloalkyl, $C_1-C_6$-haloalkyl, $C_1-C_6$-halocycloalkyl, $C_2-C_6$-alkenyl, $C_2-C_6$-haloalkenyl, $C_2-C_6$-alkynyl, $C_2-C_6$-haloalkynyl, $C_1-C_4$-alkoxy, $C_1-C_4$-haloalkoxy, $C_1-C_4$-alkylthio, $C_1-C_4$-alkylsulphinyl, $C_1-C_4$-alkylsulphonyl, $C_1-C_4$-haloalkylthio, $C_1-C_4$-haloalkylsulphinyl, $C_1-C_4$-haloalkylsulphonyl, halogen, cyano, nitro or $C_3-C_6$-trialkylsilyl, $R^6$ represents hydrogen, $C_1-C_6$-alkyl, $C_2-C_6$-alkenyl, $C_2-C_6$-alkynyl, $C_3-C_6$-cycloalkyl, $C_1-C_6$-haloalkyl, $C_2-C_6$-haloalkenyl or

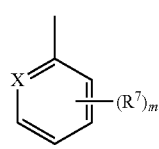

$R^6$ further represents $C_3-C_6$-cycloalkoxy, $R^7$ represents independently at each occurrence hydrogen, $C_1-C_6$-alkyl, $C_3-C_6$-cycloalkyl, $C_1-C_6$-haloalkyl, halogen, cyano, nitro, $C_1-C_4$-alkoxy, $C_1-C_4$-haloalkoxy, $C_1-C_4$-alkylthio or $C_1-C_4$-haloalkylthio, m represents 0 to 4, X represents N, CH, CF, CCl, CBr or CI, A represents —CH$_2$—, —CH$_2$O—, —CH$_2$OCH$_2$—, —CH$_2$S—, —CH$_2$SCH$_2$—, —CH$_2$N(C$_1$-C$_6$-alkyl)-, —CH$_2$N(C$_1$-C$_6$-alkyl)CH$_2$—, —CH[CO$_2$(C$_1$-C$_6$-alkyl)]-, —CH(CN)—, —CH(C$_1$-C$_6$-alkyl)-, —C(di-C$_1$-C$_6$-alkyl)-, —CH$_2$CH$_2$— or —C=NO(C$_1$-C$_6$-alkyl)-, Q represents a 5- or 6-membered heteroatomatic ring or an aromatic 8-, 9- or 10-membered fused heterobicyclic ring system, the ring system being unsubstituted or substituted one or more times by identical or different substituents selectable independently of one another from hydrogen, $C_1-C_6$-alkyl, $C_2-C_6$-alkenyl, $C_2-C_6$-alkynyl, $C_3-C_6$-cycloalkyl, $C_1-C_6$-haloalkyl, $C_2-C_6$-haloalkenyl, $C_2-C_6$-haloalkynyl, $C_3-C_6$-halocycloalkyl, halogen, CN, $CO_2H$, $CO_2NH_2$, $NO_2$, OH, $C_1-C_4$-alkoxy, $C_1-C_4$-haloalkoxy, $C_1-C_4$-alkylthio, $C_1-C_4$-alkylsulphinyl, $C_1-C_4$-alkylsulphonyl, $C_1-C_4$-haloalkylthio, $C_1-C_4$-haloalkylsulphinyl, $C_1-C_4$-haloalkylsulphonyl, $C_1-C_4$-alkylamino, di($C_1-C_4$-alkyl)amino, $C_3-C_6$-cycloalkylamino, ($C_1-C_6$-alkyl)carbonyl, ($C_1-C_6$-alkoxy)carbonyl, ($C_1-C_6$-alkyl)aminocarbonyl, di($C_1-C_4$-alkyl)aminocarbonyl, tri($C_1-C_2$-alkyl)silyl and ($C_1-C_4$-alkyl)($C_1-C_4$-alkoxy)imino, Q further represents a 5- or 6-membered heteroaromatic or heterocyclic ring or an aromatic 8-, 9- or 10-membered fused heterobicyclic ring system, the ring or the ring system being unsubstituted or substituted one or more times by identical or different substituents selectable independently of one another from hydrogen, $C_1-C_6$-alkyl, $C_2-C_6$-alkenyl, $C_2-C_6$-alkynyl, $C_3-C_6$-cycloalkyl, $C_1-C_6$-haloalkyl, $C_2-C_6$-haloalkenyl, $C_2-C_6$-haloalkynyl, $C_3-C_6$-halocycloalkyl, halogen, CN, $CO_2H$, $CO_2NH_2$, $NO_2$, OH, $C_1-C_4$-alkoxy, $C_1-C_4$-haloalkoxy, $C_1-C_4$-alkylthio, $C_1-C_4$-alkylsulphinyl, $C_1-C_4$-alkylsulphonyl, $C_1-C_4$-haloalkylthio, $C_1-C_4$-haloalkylsulphinyl, $C_1-C_4$-haloalkylsulphonyl, $C_1-C_4$-alkylamino, di($C_1-C_4$-alkyl)amino, $C_3-C_6$-cycloalkylamino, ($C_1-C_6$-alkyl)carbonyl, ($C_1-C_6$-alkoxy)carbonyl, ($C_1-C_6$-alkyl)aminocarbonyl, di($C_1-C_4$-alkyl)aminocarbonyl, tri($C_1-C_2$-alkyl)silyl and ($C_1-C_4$-alkyl)($C_1-C_4$-alkoxy)imino, or the substituents being selectable independently of one another from phenyl or a 5- or 6-membered heteroaromatic ring, it being possible for phenyl or the ring to be unsubstituted or substituted one or more times by identical or different $C_1-C_6$-alkyl, $C_2-C_6$-alkenyl, $C_2-C_6$-alkynyl, $C_3-C_6$-cycloalkyl, $C_1-C_6$-haloalkyl, $C_2-C_6$-haloalkenyl, $C_2-C_6$-haloalkynyl, $C_3-C_6$-halocycloalkyl, halogen, CN, $NO_2$, OH, $C_1-C_4$-alkoxy, $C_1-C_4$-haloalkoxy substituents, whereas the compounds of the general formula (I) also encompass N-oxides and salts, for controlling animal pests, such as insects and/or unwanted acarids and/or nematodes in transgenic crops and to methods particularly useful for controlling insects, and/or acarids and/or nematodes and/or increasing crop yield in those crops.

Accordingly, the present invention also relates to the use of compositions comprising a compound of the general formula (I) for controlling animal pests, such as insects and/or unwanted acarids and/or nematodes in transgenic crops and/or increasing crop yield in those crops.

Accordingly, the present invention also relates to the use of compositions comprising A) a compound of the general formula (I) and
B) at least one further agrochemically active compound,
for controlling animal pests, such as insects and/or unwanted acarids and/or nematodes in transgenic crops and/or increasing crop yield in those crops.

An exemplary method of the invention comprises applying a compound of the general formula (I) of the invention to either soil or a plant (e.g., seeds or foliarly) for controlling animal pests, such as insects and/or unwanted acarids and/or nematodes in transgenic crops and/or increasing crop yield in those crops.

The present invention is drawn to compositions and methods for regulating pest resistance or tolerance in plants or plant cells. By "resistance" is intended that the pest (e.g., insect or nematode) is killed upon ingestion or other contact with the plant or parts thereof. By "tolerance" is intended an impairment or reduction in the movement, feeding, reproduction, or other functions of the pest. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

In conjunction with the present invention "controlling" denotes a preventive or curative reduction of the insect or nematode infestation in comparison to the untreated crop, more preferably the infestation is essentially repelled, most preferably the infestation is totally suppressed.

By "pesticidally-effective amount" is intended an amount of the pesticide that is able to bring about death to at least one pest, or to noticeably reduce pest growth, feeding, or normal physiological development. This amount will vary depending on such factors as, for example, the specific target pests to be controlled, the specific environment, location, plant, crop, or agricultural site to be treated, the environmental conditions, and the method, rate, concentration, stability, and quantity of application of the pesticidally-effective polypeptide composition.

The present invention also relates to a method for the protection of seed and germinating plants, or plant from attack by pests, by selectively applying pesticidal agents to the seed of a transgenic plant. Pesticidal agents include chemical or biological control agents compositions applied to the seed of the transgenic plant, wherein the agent is intended to provide protection of the plant or seed thereof against damage caused by one or more plant pests. Furthermore, the invention relates to seed which has been treated with a pesticidal agent as described herein. Application of a pesticidal agent to the seed of a transgenic plant results in an improved resistance or tolerance to one or more plant pests and/or improved yield or vigor compared to a transgenic plant cultivated from a seed not treated with a pesticidal agent as described herein, or a plant of the same species as the referenced transgenic plant that has been cultivated from a seed treated with a pesticidal agent as described herein but that lacks the transgene (either of which may be herein referred to as a "control" plant).

In some embodiments, treatment of the seed with these agents not only protects the seed itself, but also the resulting plants after emergence, from pests. In this manner, the immediate treatment of the crop at the time of sowing or shortly thereafter can be dispensed with.

DETAILED DESCRIPTION OF A PREFERRED EMBODIMENT

Preferred radical definitions for the formula (I) given above are specified below.

$R^1$ preferably represents hydrogen, $C_1$-$C_6$-alkyl, $C_2$-$C_6$-alkenyl, $C_2$-$C_6$-alkynyl, $C_3$-$C_6$-cycloalkyl, cyano($C_1$-$C_6$-alkyl), $C_1$-$C_6$-haloalkyl, $C_2$-$C_6$-haloalkenyl, $C_2$-$C_6$-haloalkynyl, $C_1$-$C_4$-alkoxy-$C_1$-$C_4$-alkyl, $C_1$-$C_4$-alkylthio-$C_1$-$C_4$-alkyl, $C_1$-$C_4$-alkylsulphinyl-$C_1$-$C_4$-alkyl or $C_1$-$C_4$-alkyl-sulphonyl-$C_1$-$C_4$-alkyl.

$R^1$ more preferably represents hydrogen, methyl, cyclopropyl, cyanomethyl, methoxymethyl, methylthiomethyl, methylsulphinylmethyl or methylsulphonylmethyl.

$R^1$ very preferably represents hydrogen.

$R^2$ preferably represents hydrogen or $C_1$-$C_6$-alkyl.

$R^2$ more preferably represents hydrogen or methyl.

$R^2$ very preferably represents hydrogen.

$R^3$ preferably represents hydrogen or represents $C_1$-$C_6$-alkyl, $C_1$-$C_6$-alkoxy, $C_2$-$C_6$-alkenyl or $C_2$-$C_6$-alkynyl each of which is unsubstituted or substituted one or more times by identical or different substituents selectable from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl or $C_3$-$C_6$-trialkylsilyl, $R^3$ further preferably represents $C_3$-$C_{12}$-cycloalkyl and $C_4$-$C_{10}$-bicycloalkyl, the substituents being selectable independently of one another from halogen, cyano, nitro, hydroxy, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl or $C_3$-$C_6$-trialkylsilyl, $R^3$ more preferably represents hydrogen or represents $C_1$-$C_6$-alkyl, $C_1$-$C_6$-alkoxy each of which is unsubstituted or substituted one or more times by identical or different substituents selectable independently of one another from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkyl-sulphoximino-$C_1$-$C_4$-alkyl, $C_1$-$C_4$-alkylsulphoximino-$C_2$-$C_5$-alkylcarbonyl, $C_2$-$C_6$-alkoxy-carbonyl, $C_2$-$C_6$-alkylcarbonyl or $C_3$-$C_6$-trialkylsilyl, $R^3$ further more preferably represents $C_3$-$C_6$-cycloalkyl which is unsubstituted or substituted one or more times by identical or different substituents selectable independently of one another from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_{1-4}$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl or $C_3$-$C_6$-trialkylsilyl, $R^3$ very preferably represents $C_1$-$C_4$-alkyl (methyl, ethyl, n-propyl, isopropyl, n-butyl, isobutyl, sec-butyl or tert-butyl) or cyano-$C_1$-$C_3$-alkyl (cyanomethyl, 1-cyanoethyl, 2-cyanoethyl, 1-cyano-n-propyl, 2-cyano-n-propyl, 3-cyano-n-propyl, 1-cyanoisopropyl, 2-cyanoisopropyl).

$R^3$ with particular preference represents methyl, isopropyl or cyanomethyl.

$R^4$ preferably represents hydrogen, $C_1$-$C_4$-alkyl, $C_1$-$C_4$-haloalkyl, halogen, cyano, $C_1$-$C_4$-alkoxy, $C_1$-$C_4$-haloalkoxy, $C_1$-$C_4$-alkylthio or $C_1$-$C_4$-haloalkylthio.

Preferably, moreover, two adjacent radicals $R^4$ represent —$(CH_2)_3$—, —$(CH_2)_4$—, —$(CH_2)_5$—, —(CH=CH—)$_2$—, —OCH$_2$O—, —O(CH$_2$)$_2$O—, —OCF$_2$O—, —(CF$_2$)$_2$O—, —O(CF$_2$)$_2$O—, —(CH=CH—CH=N)— or —(CH=CH—N=CH)—.

$R^4$ more preferably represents hydrogen, $C_1$-$C_4$-alkyl, $C_1$-$C_2$-haloalkyl, halogen, cyano or $C_1$-$C_2$-haloalkoxy.

More preferably, moreover, two adjacent radicals $R^4$ represent —(CH$_2$)$_4$—, —(CH=CH—)$_2$—, —O(CH$_2$)$_2$O—, —O(CF$_2$)$_2$O—, —(CH=CH—CH=N)— or —(CH=CH—N=CH)—.

$R^4$ very preferably represents hydrogen, methyl, trifluoromethyl, cyano, fluorine, chlorine, bromine, iodine or trifluoromethoxy. Very preferably, moreover, two adjacent radicals $R^4$ represent —(CH$_2$)$_4$—, or —(CH=CH—)$_2$—.

$R^4$ with particular preference represents chlorine or bromine.

$R^4$ further with particular preference represents iodine or cyano. With particular preference, moreover, two adjacent radicals $R^4$ represent —(CH=CH—)$_2$—.

$R^5$ preferably represents $C_1$-$C_4$-alkyl, $C_3$-$C_6$-cycloalkyl, $C_1$-$C_4$-haloalkyl, $C_1$-$C_6$-halocycloalkyl, $C_2$-$C_6$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro or $C_3$-$C_6$-trialkylsilyl.

$R^5$ more preferably represents $C_1$-$C_4$-alkyl, $C_3$-$C_6$-cycloalkyl, $C_1$-$C_4$-haloalkyl, $C_1$-$C_6$-halocycloalkyl, $C_2$-$C_6$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, fluorine, chlorine, bromine, iodine, cyano, nitro or $C_3$-$C_6$-trialkylsilyl.

$R^5$ very preferably represents methyl, fluorine, chlorine, bromine or iodine.

$R^5$ with particular preference represents methyl or chlorine.

$R^6$ preferably represents $C_1$-$C_6$-alkyl or

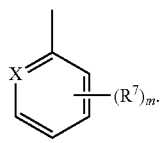

$R^6$ further preferably represents $C_3$-$C_6$-cycloalkoxy.
$R^6$ more preferably represents methyl or

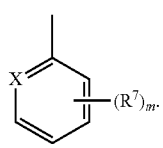

$R^7$ independently at each occurrence preferably represents hydrogen, halogen, cyano, $C_1$-$C_4$, $C_1$-$C_4$-alkoxy, $C_1$-$C_4$-haloalkyl, $C_1$-$C_4$-haloalkoxy, $C_1$-$C_4$-haloalkylsulphonyl or ($C_1$-$C_4$alkyl)$C_1$-$C_4$-alkoxyimino, $R^7$ independently at each occurrence more preferably represents hydrogen, halogen or $C_1$-$C_4$-haloalkyl, $R^7$ very preferably represents fluorine, chlorine or bromine, $R^7$ with particular preference represents chlorine.

m preferably represents 1, 2 or 3, m more preferably represents 1 or 2, m very preferably represents 1, X preferably represents N, CH, CF, CCl, CBr or CI, X more preferably represents N, CH, CF, CCl or CBr, X very preferably represents N, CCl or CH.

A preferably represents —CH$_2$—, —CH$_2$O—, —CH$_2$OCH$_2$—, —CH$_2$S—, —CH$_2$SCH$_2$—, —CH$_2$N($C_1$-$C_6$-alkyl)-, —CH$_2$N($C_1$-$C_6$-alkyl)CH$_2$—, —CH(CN)—, —CH($C_1$-$C_6$-alkyl)-, —C(di-$C_1$-$C_6$-alkyl)-, —CH$_2$CH$_2$— or —C=NO($C_1$-$C_6$-alkyl)-, A more preferably represents —CH$_2$—, —CH(CH$_3$), C(CH$_3$)$_2$ or CH$_2$CH$_2$, A further more preferably represents —CH(CN)—, A very preferably represents CH$_2$ or CH(CH$_3$), A with particular preference represents CH$_2$.

Q preferably represents an optionally mono- or polysubstituted 5- or 6-membered aromatic heterocyclic ring of series Q-1 to Q-53 or an aromatic 9-membered fused heterobicyclic ring system Q-54 to Q-56, the substituents being selectable independently of one another from $C_1$-$C_3$-alkyl, $C_1$-$C_3$-haloalkyl, $C_1$-$C_2$-alkoxy, halogen, cyano, hydroxyl, nitro or $C_1$-$C_2$-haloalkoxy.

Q further preferably represents an optionally mono- or polysubstituted 5- or 6-membered aromatic heterocyclic ring of series Q-1 to Q-53 and Q-58 to Q-59, an aromatic 9-membered fused heterobicyclic ring system Q-54 to Q-56 and also represents a 5-membered heterocyclic ring Q-60 to Q-61, the substituents being selectable independently of one another from $C_1$-$C_3$-alkyl, $C_1$-$C_3$-haloalkyl, $C_1$-$C_2$-alkoxy, halogen, cyano, hydroxyl, nitro or $C_1$-$C_2$-haloalkoxy, or the substituents being selectable independently of one another from phenyl or a 5- or 6-membered heteroaromatic ring, it being possible for phenyl or the ring to be substituted where appropriate one or more times by identical or different $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, NO$_2$, OH, $C_1$-$C_4$-alkoxy or $C_1$-$C_4$-haloalkoxy substituents, Q more preferably represents an optionally mono- or polysubstituted 5- or 6-membered aromatic heterocyclic ring of series Q-36 to Q-40 or an aromatic 9-membered fused heterobicyclic ring system Q-54 to Q-56, the substituents being selectable independently of one another from $C_1$-$C_3$-alkyl, $C_1$-$C_3$-haloalkyl, $C_1$-$C_2$-alkoxy, halogen, cyano, hydroxyl, nitro or $C_1$-$C_2$-haloalkoxy.

Q further more preferably represents an optionally mono- or polysubstituted 5- or 6-membered aromatic heterocyclic ring of series Q-36 to Q-40 and Q-58 to Q-59, an aromatic 9-membered fused heterobicyclic ring system Q-54 to Q-56 and also represents a 5-membered heterocyclic ring Q-60 to Q-61, the substituents being selectable independently of one another from $C_1$-$C_3$-alkyl, $C_1$-$C_3$-haloalkyl, $C_1$-$C_2$-alkoxy, halogen, cyano, hydroxyl, nitro or $C_1$-$C_2$-haloalkoxy, or the substituents being selectable independently of one another from phenyl or a 5- or 6-membered heteroaromatic ring, it being possible for phenyl or the ring to be unsubstituted or substituted one or more times by identical or different $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, $C_1$-$C_4$-alkoxy or $C_1$-$C_4$-haloalkoxy substituents, Q very preferably represents an optionally mono- or polysubstituted aromatic heterocyclic ring of series Q-37, Q-38, Q-39, Q-40, Q-58 and Q-59, and also represents a 5-membered heterocyclic ring Q-60, the substituents being selectable independently of one another from $C_1$-$C_3$-alkyl, $C_1$-$C_3$-haloalkyl, $C_1$-$C_2$-alkoxy, halogen, cyano, hydroxyl, nitro or $C_1$-$C_2$-haloalkoxy, or the substituents being selectable independently of one another from phenyl or a 5- or 6-membered heteroaromatic ring, it being possible for phenyl or the ring to be unsubstituted or substituted one or more times by identical or different $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, $C_1$-$C_4$-alkoxy or $C_1$-$C_4$-haloalkoxy substituents, Q further very preferably represents an optionally mono- or polysubstituted aromatic heterocyclic ring of series Q-37, Q-38, Q-39, Q-40, Q-58 and Q-59, and also represents a 5-membered heterocyclic ring Q-60, the substituents being selectable independently of one another from $C_1$-$C_3$-alkyl, $C_1$-$C_3$-haloalkyl, halogen, cyano, nitro or $C_1$-$C_2$-haloalkoxy, or the substituents being selectable independently of one another from phenyl or a 5- or 6-membered heteroaromatic ring, it being possible for phenyl or the ring to be unsubstituted or substituted one or more times by identical or different $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, $C_1$-$C_4$-alkoxy or $C_1$-$C_4$-haloalkoxy substituents, Q with particular preference represents an aromatic heterocyclic ring Q-37, Q-40, Q-58 and Q-59 which is unsubstituted or substituted once, twice or three times on carbon atoms, and also represents a 5-membered heterocyclic ring Q-60, the substituents being selectable independently of one another from chlorine, fluorine, iodine, bromine, cyano, trifluoromethyl and pentafluoroethyl, or the substituents being selectable independently of one another from phenyl, it being possible for the phenyl ring to be unsubstituted or substituted one or more times by identical or different $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$ or $C_1$-$C_4$-haloalkoxy substituents, Q further with particular preference represents an optionally mono- or polysubstituted aromatic heterocyclic ring of series Q-37, Q-40, Q-58 and Q-59, and also represents a 5-membered heterocyclic ring Q-60, the substituents being selectable independently of one another from chlorine, fluorine, iodine, cyano, trifluoromethyl and pentafluoroethyl, or the substituents being selectable independently of one another from phenyl, it being possible for the phenyl ring to be unsubstituted or substituted one or more times by identical or different chlorine, fluorine, iodine, bromine, cyano, trifluoromethyl and pentafluoroethyl substituents,

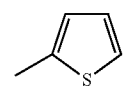 Q-1

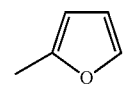 Q-2

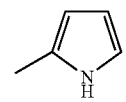 Q-3

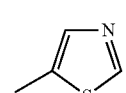 Q-4

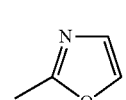 Q-5

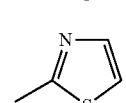 Q-6

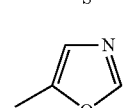 Q-7

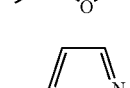 Q-8

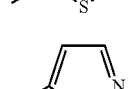 Q-9

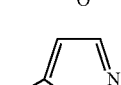 Q-10

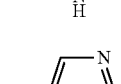 Q-11

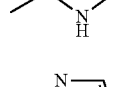 Q-12

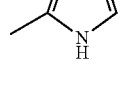 Q-13

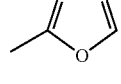 Q-14

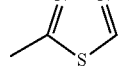 Q-15

-continued
| | |
|---|---|
| 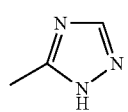 | Q-16 |
| 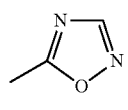 | Q-17 |
| 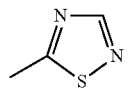 | Q-18 |
| 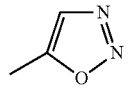 | Q-19 |
| 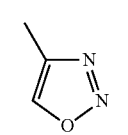 | Q-20 |
| 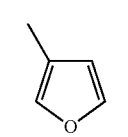 | Q-21 |
| 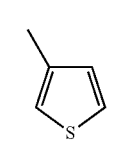 | Q-22 |
| 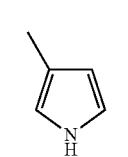 | Q-23 |
| 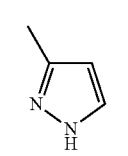 | Q-24 |
| 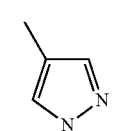 | Q-25 |
| 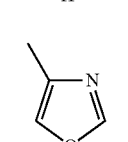 | Q-26 |
| 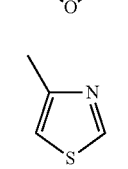 | Q-27 |
-continued
| | |
|---|---|
| 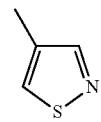 | Q-28 |
| 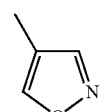 | Q-29 |
| 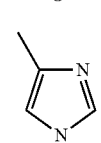 | Q-30 |
| 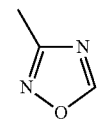 | Q-31 |
| 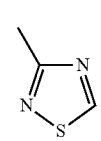 | Q-32 |
| 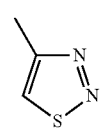 | Q-33 |
| 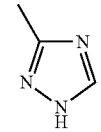 | Q-34 |
| 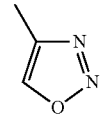 | Q-35 |
| 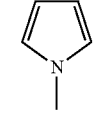 | Q-36 |
| 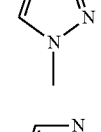 | Q-37 |
| 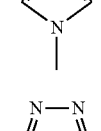 | Q-38 |
| 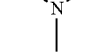 | Q-39 |

Q-40 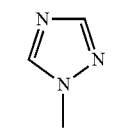
Q-41 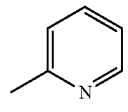
Q-42 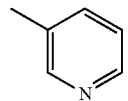
Q-43 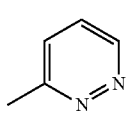
Q-44 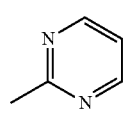
Q-45 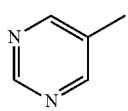
Q-46 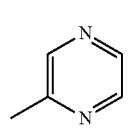
Q-47 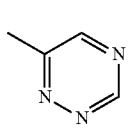
Q-48 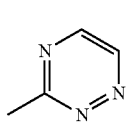
Q-49 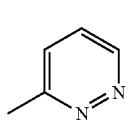
Q-50 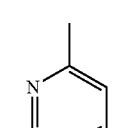
Q-51 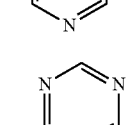
Q-52 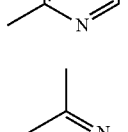
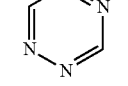
Q-53 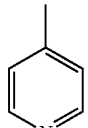
Q-54 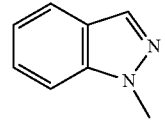
Q-55 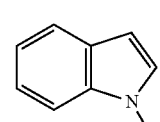
Q-56 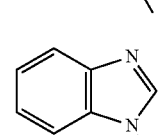
Q-57 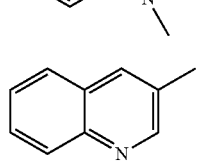
Q-58 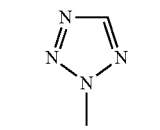
Q-59 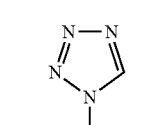
Q-60 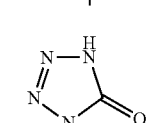
Q-61 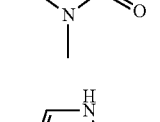
Q-62 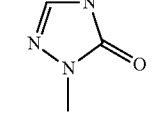
Q-63 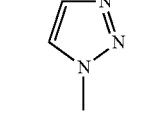
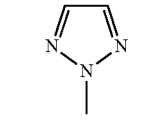
Emphasis is given to the use of compounds of the formula (I-1) according to the invention

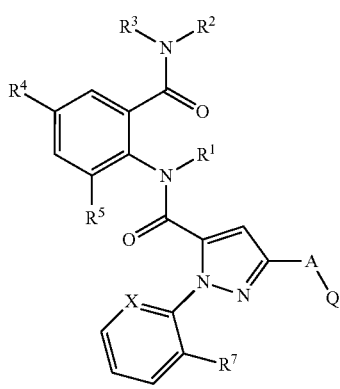

(I-1)

in which R¹, R², R³, R⁴, R⁵, R⁷, A, Q and X have the above-indicated general, preferred, more preferred, very preferred and particularly preferred definitions.

The compounds of the formula (I) or (I-1) may be present in the form of different regioisomers: for example in the form of mixture of compounds with the definition of Q62 and Q63 or in the form of mixtures of Q58 and Q59. The invention therefore also encompasses compounds of the formula (I) or (I-1) where $Q_Y$ is defined as Q62 and Q63, and Q58 and Q59, in different mixing ratios; to be used for controlling animal pests, such as insects and/or unwanted acarids and/or nematodes in transgenic crops and to methods particularly useful for controlling insects, and/or acarids and/or nematodes and/or increasing crop yield in those crops.

Preference is given to mixing ratios of compounds of the formula (I) in which the $Q_Y$ radical is Q62 or Q58 to compounds of the formula (I) in which the Qy radical is Q63 or Q59 of 60:40 to 99:1, more preferably of 70:30 to 97:3, even more preferably of 80:20 to 99:1. Especially preferred are the following mixing ratios of a compound of the formula (I) where $Q_Y$ is defined as Q62 or Q58 to the compound of the formula (I) where $Q_Y$ is defined as Q63 or Q59: 80:20; 81:19; 82:18; 83:17; 84:16; 85:15; 86:14; 87:13; 88:12; 89:11; 90:10, 91:9; 92:8; 93:7; 94:6, 95:5, 96:4, 97:3, 98:2, 99:1.

More preferred is the use of the compounds (I-1-1) to (I-1-60) according to the invention

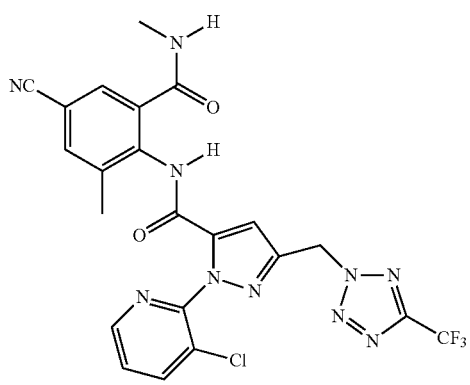

(I-1-1)

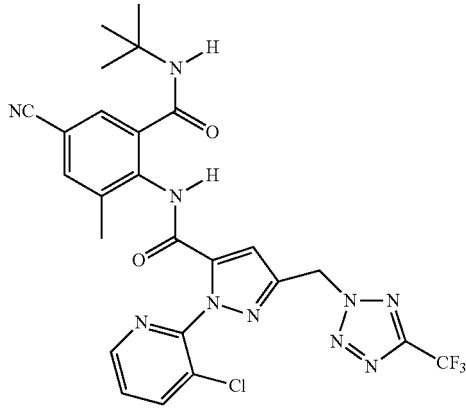

(I-1-2)

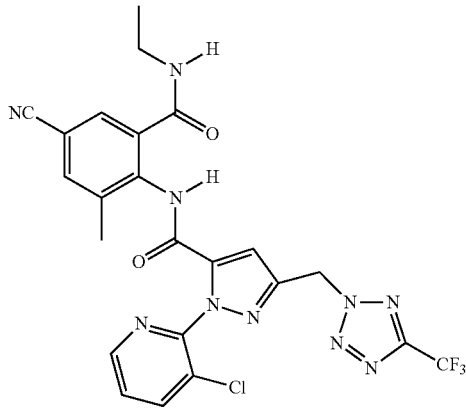

(I-1-3)

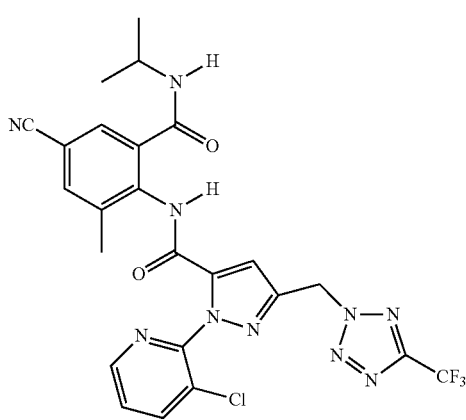

(I-1-4)

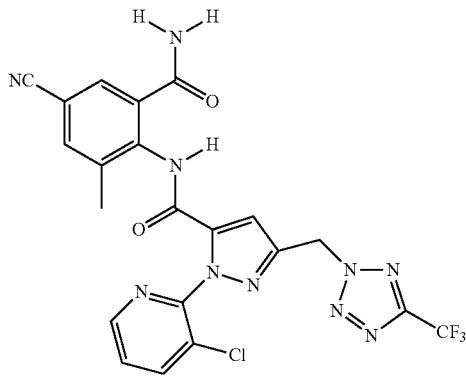

(I-1-5)

-continued
(I-1-6)
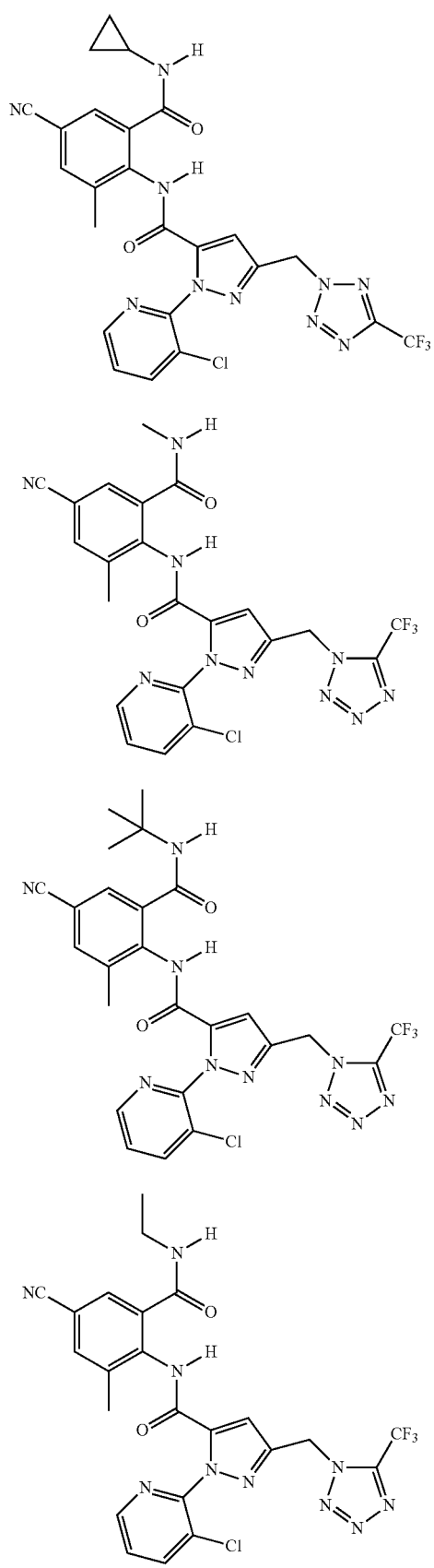
(I-1-7)
(I-1-8)
(I-1-9)
-continued
(I-1-10)
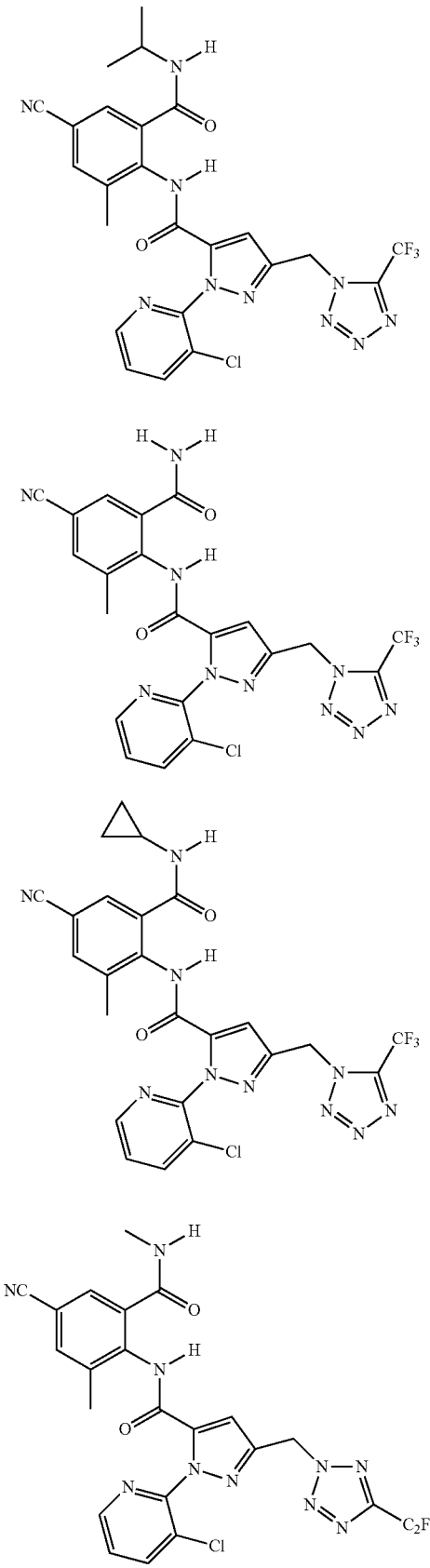
(I-1-11)
(I-1-12)
(I-1-13)

-continued
(I-1-14)
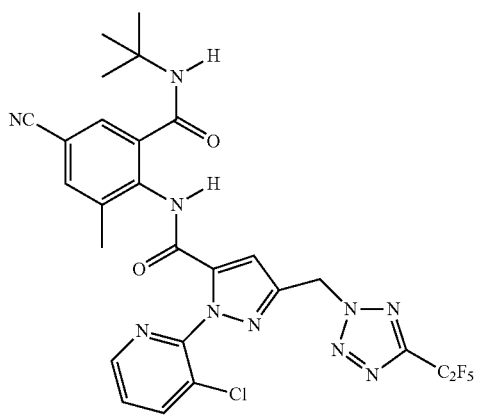
(I-1-17)
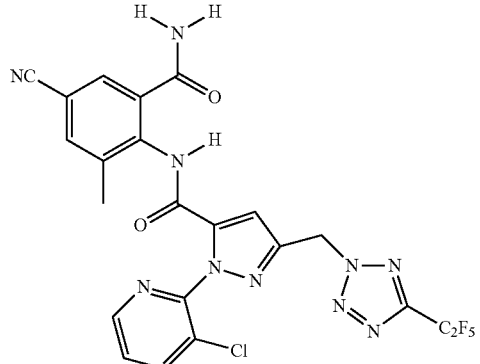
(I-1-15)
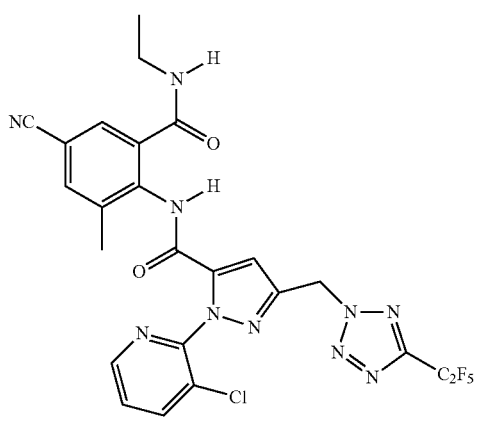
(I-1-18)
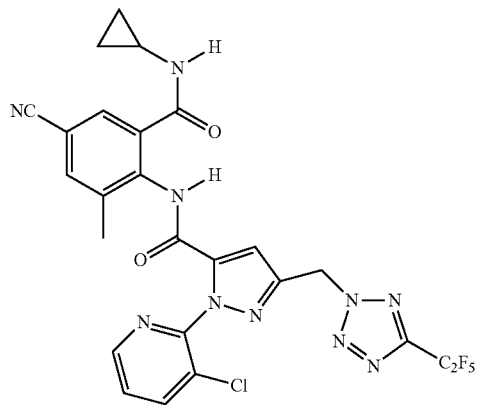
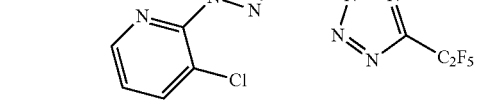
(I-1-19)
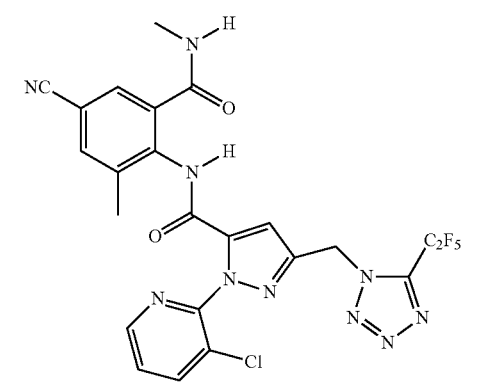
(I-1-16)
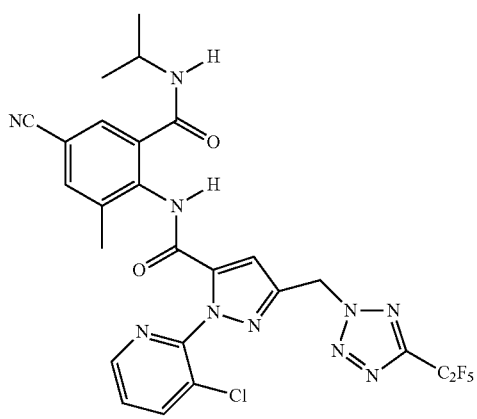
(I-1-20)
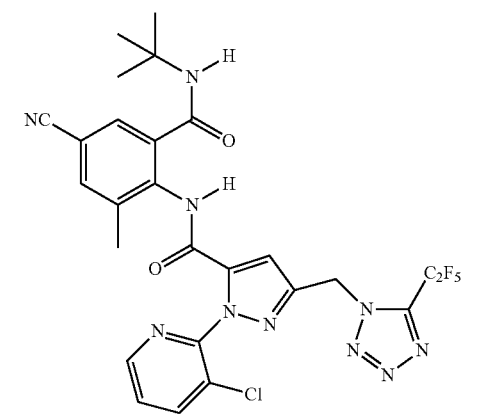

(I-1-21)
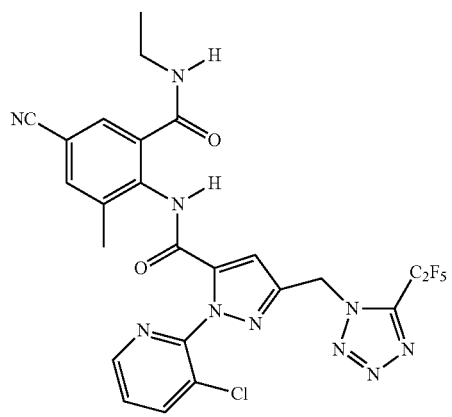
(I-1-25)
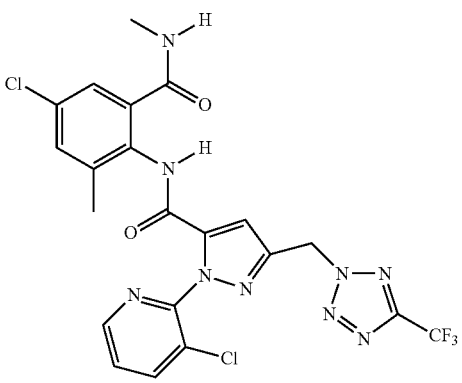
(I-1-22)
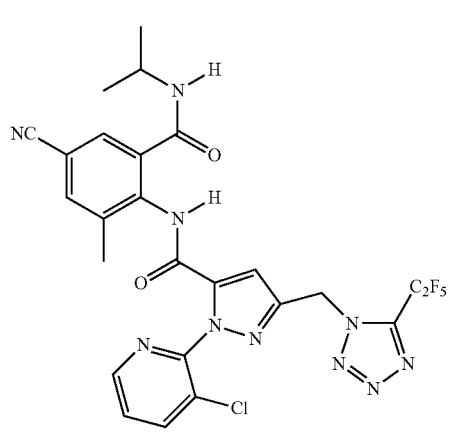
(I-1-26)
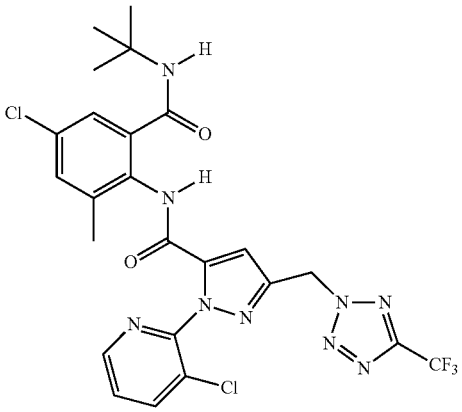
(I-1-23)
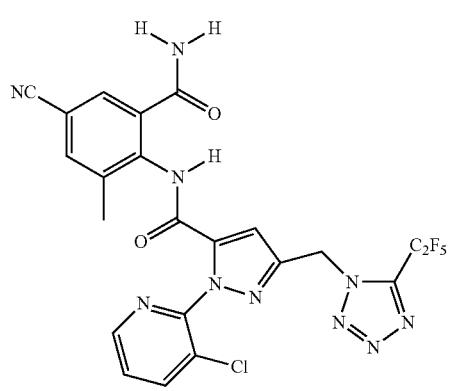
(I-1-24)
(I-1-27)
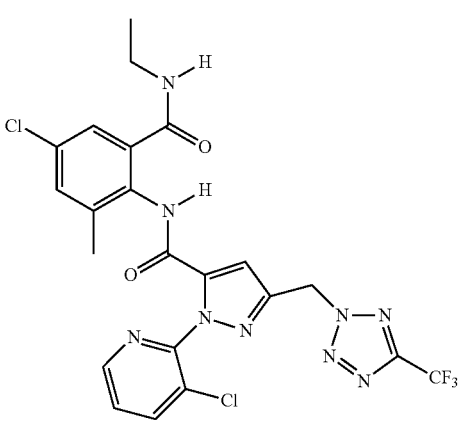

(I-1-28)
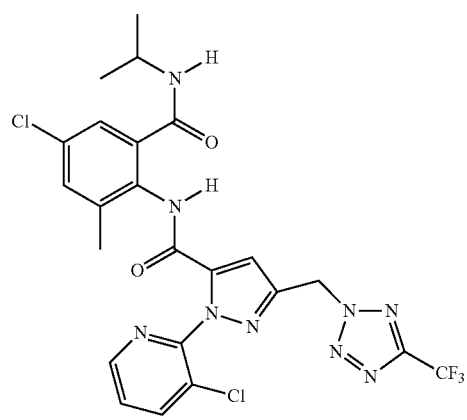
(I-1-29)
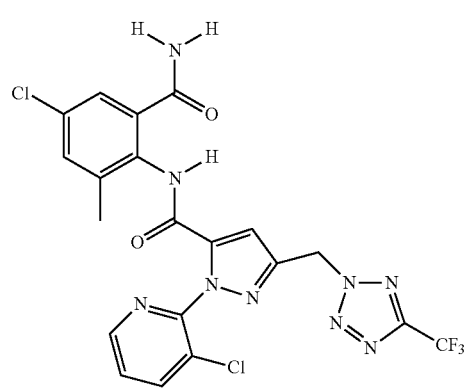
(I-1-30)
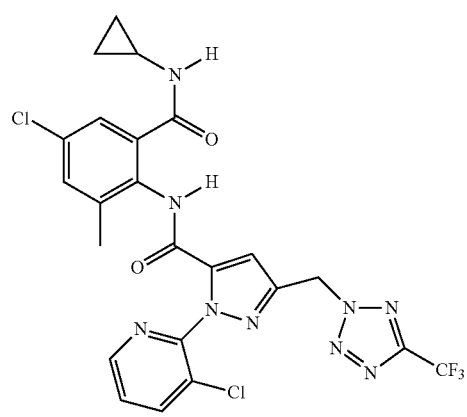
(I-1-31)
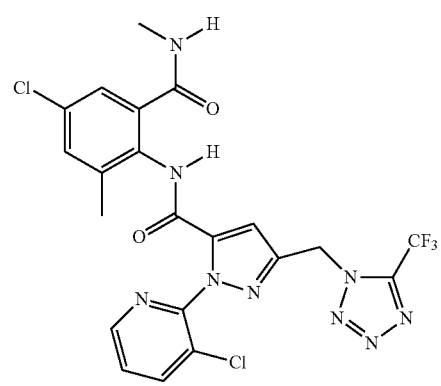
(I-1-32)
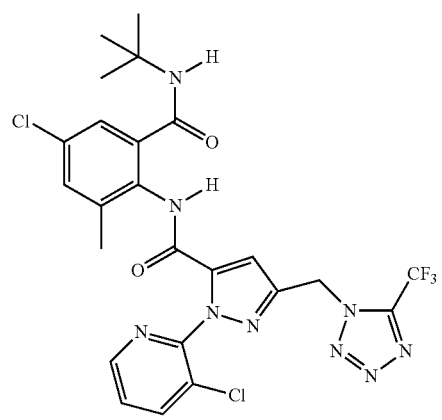
(I-1-33)
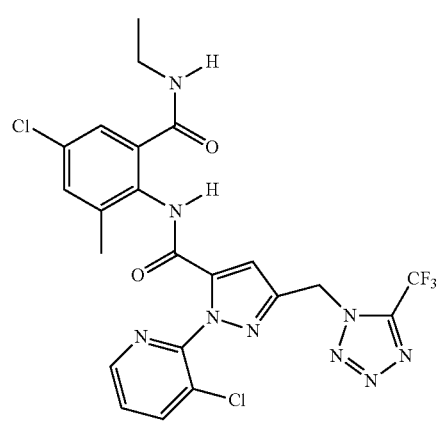
(I-1-34)
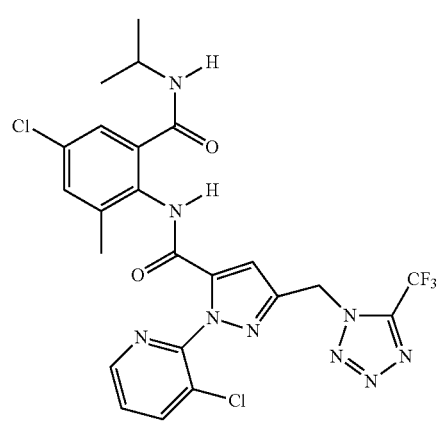
(I-1-35)
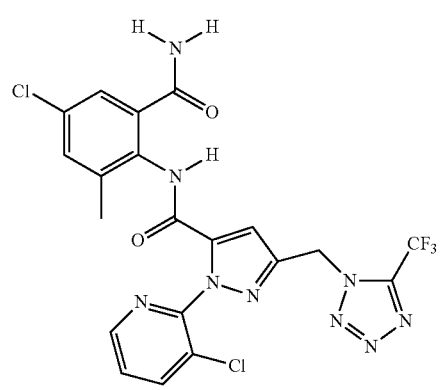

(I-1-36)
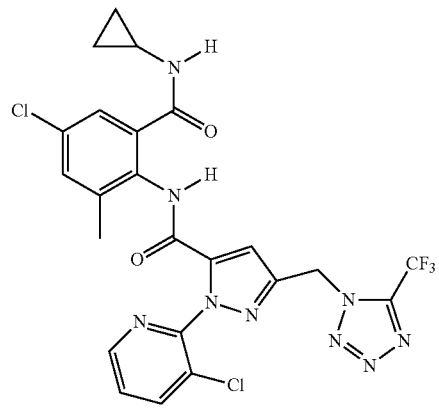
(I-1-37)
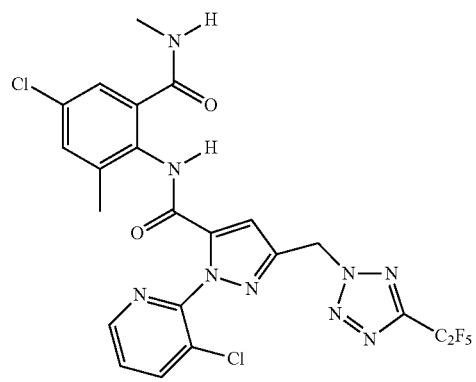
(I-1-38)
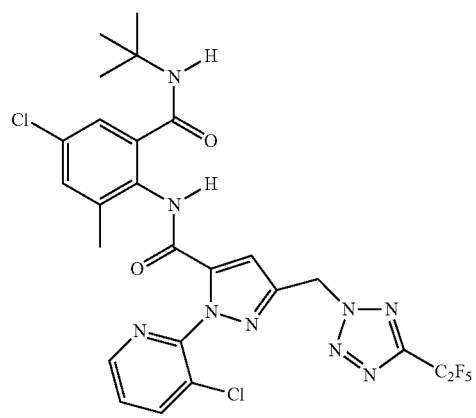
(I-1-39)
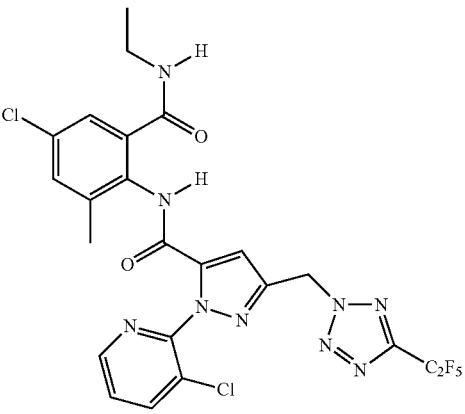
(I-1-40)
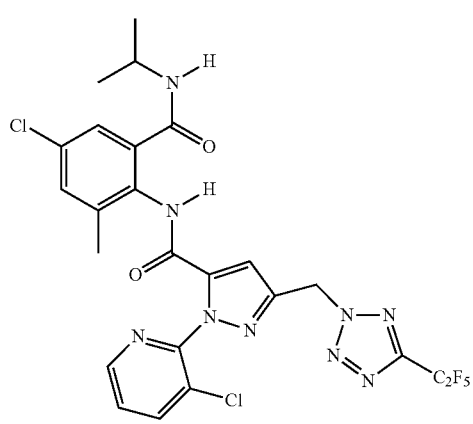
(I-1-41)
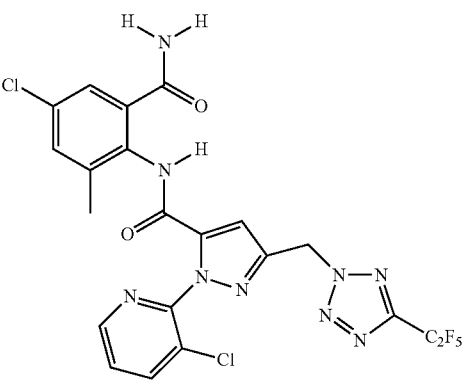

(I-1-42)
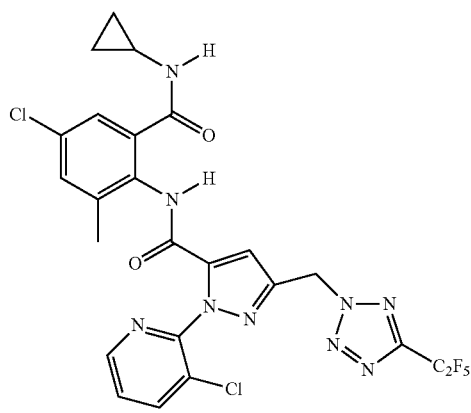
(I-1-43)
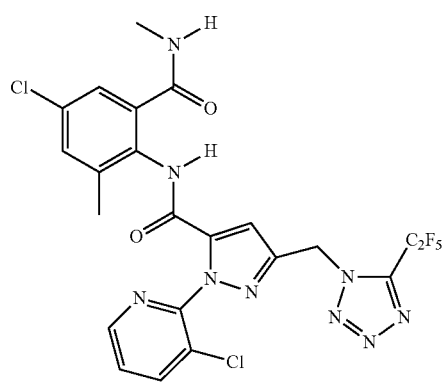
(I-1-44)
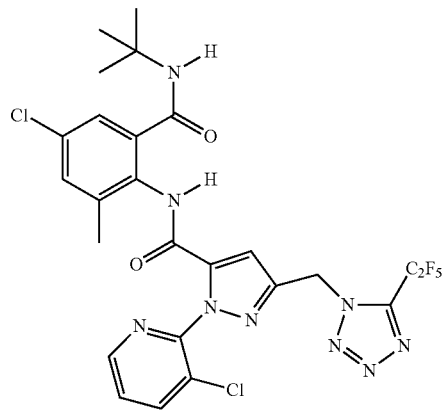
(I-1-45)
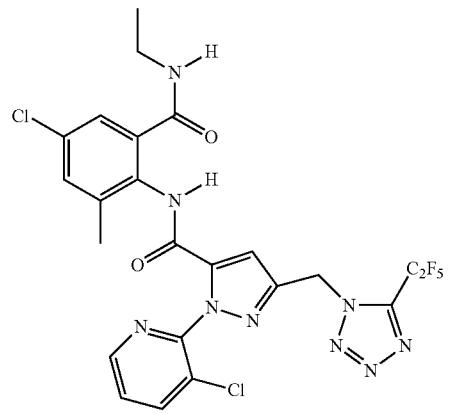
(I-1-46)
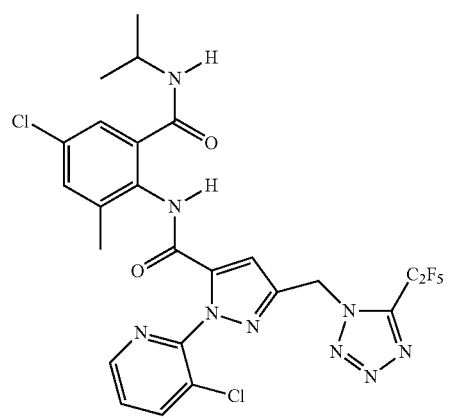
(I-1-47)
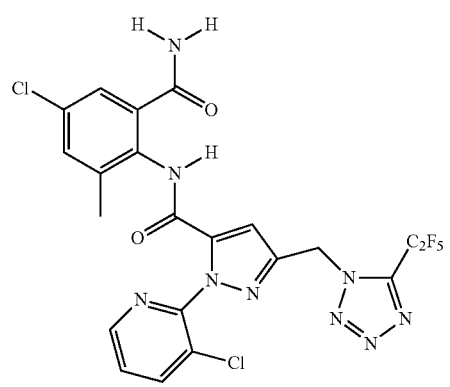
(I-1-48)
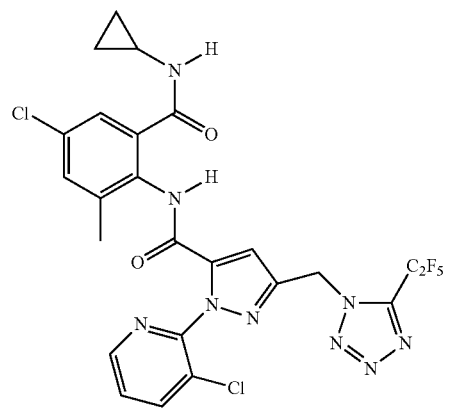

-continued
(I-1-49)
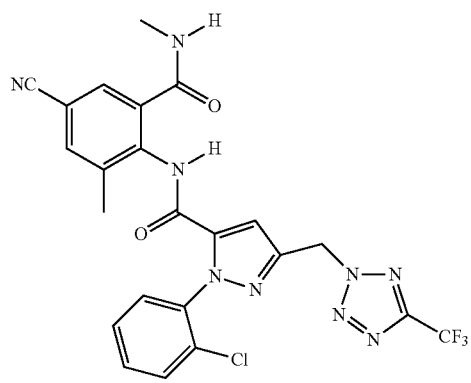
(I-1-50)
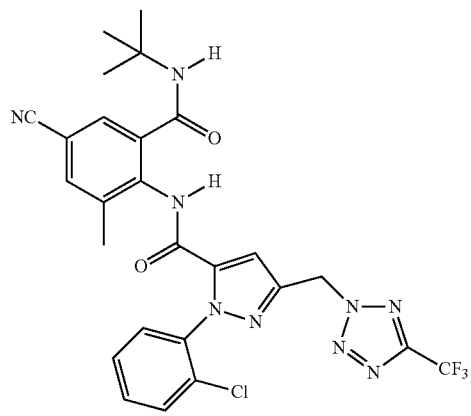
(I-1-51)
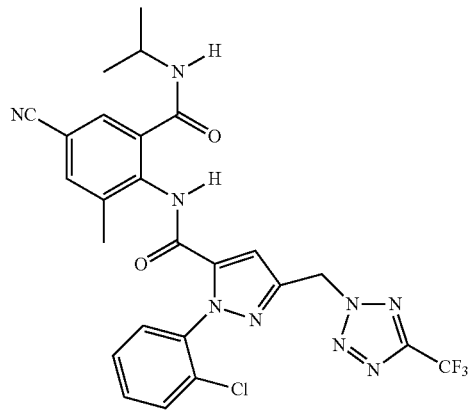
(I-1-52)
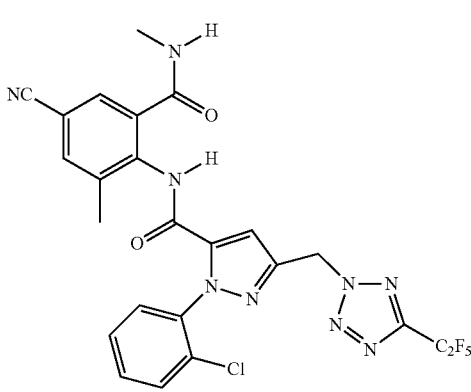
-continued
(I-1-53)
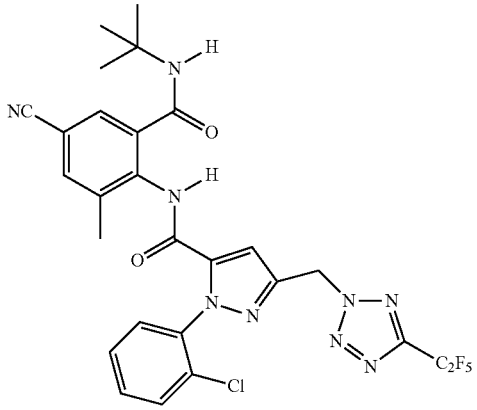
(I-1-54)
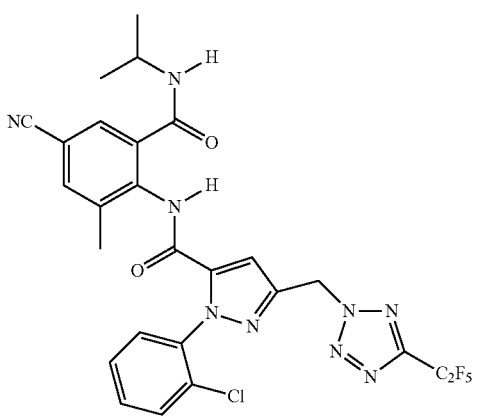
(I-1-55)
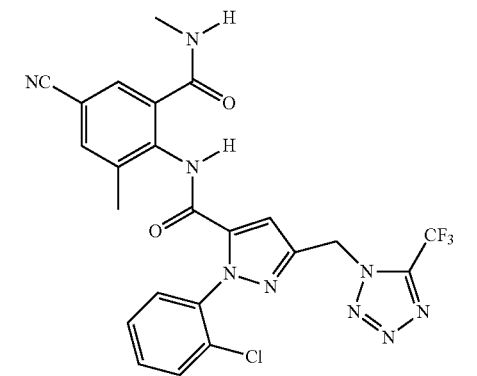
(I-1-56)
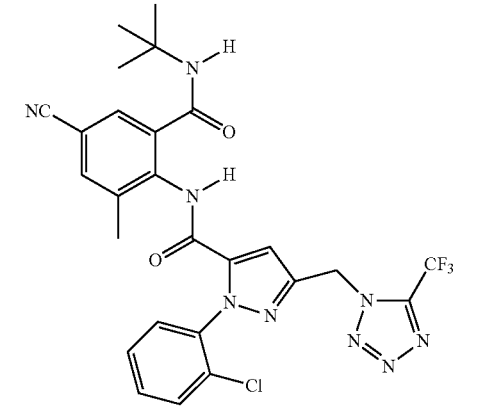

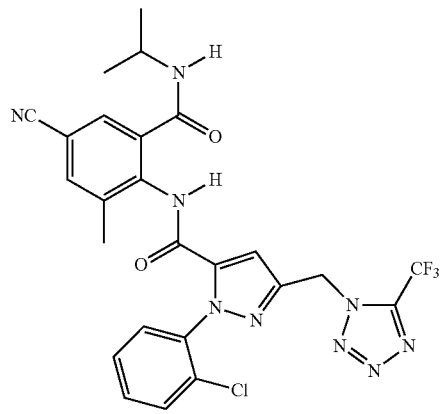
(I-1-57)

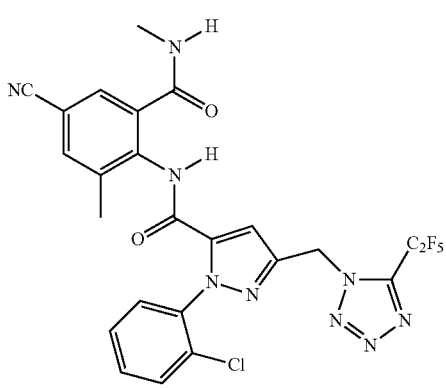
(I-1-58)

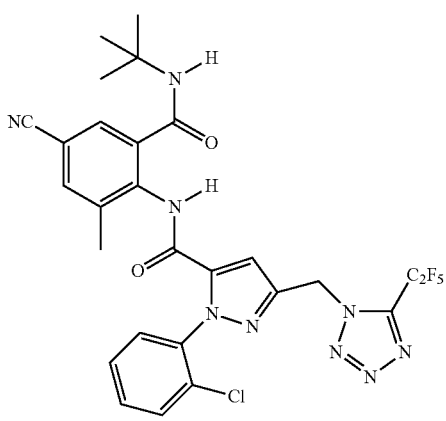
(I-1-59)

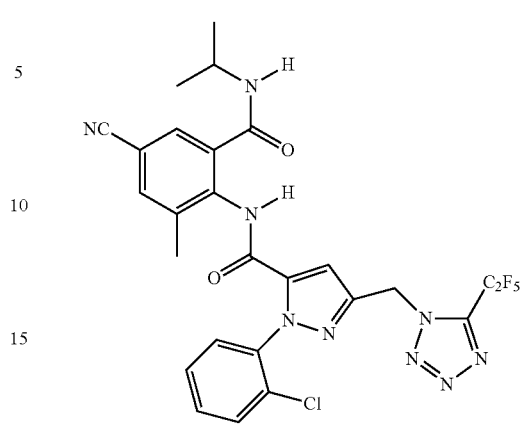
(I-1-60)

Additionally more preferred is the use of the following mixtures of compounds of the formula (I-1-1) to (I-1-60) according to the invention I-1-1-/I-1-7, 1-1-2/1-1-8, 1-1-3/1-1-9, I-1-4/1-1-10, I-1-5/1-1-11, I-1-6/1-1-12, I-1-13/I-1-1-19, 1-1-14/1-1-20, I-1-15/I-1-21, I-1-16/I-1-22, I-1-17/I-1-23, I-1-18/I-1-24, 1-1-25/1-1-31, 1-1-26/1-1-32, I-1-27/I-1-33, 1-1-28/1-1-34, I-1-29/I-1-35, I-1-30/I-1-36, 1-1-37/1-1-43, 1-1-38/1-1-44, I-1-39/I-1-45, I-1-40/I-1-46, I-1-41/I-1-47, I-1-42/I-1-48, I-1-49/I-1-55, I-1-50/I-1-56, I-1-51/I-1-57, I-1-52/I-1-58, I-1-53/I-1-59, I-1-54/I-1-60.

In a preferred embodiment the invention also relates to the use of compositions comprising A) a compound of the general formula (I-1) and
B) at least one further agrochemically active compound
for controlling animal pests, such as insects and/or unwanted acarids and/or nematodes in transgenic crops and/or increasing crop yield in those crops.

In a preferred embodiment the invention also relates to the use of compositions comprising A) compound (I-1-1) and
B) at least one further agrochemically active compound
for controlling animal pests, such as insects and/or unwanted acarids and/or nematodes in transgenic crops and/or increasing crop yield in those crops.

In a preferred embodiment the invention also relates to the use of compositions comprising A) compound (I-1-2) and
B) at least one further agrochemically active compound
for controlling animal pests, such as insects and/or unwanted acarids and/or nematodes in transgenic crops and/or increasing crop yield in those crops.

In a preferred embodiment the invention also relates to the use of compositions comprising A) a mixture of compound (I-1-1)/(I-1-7) and
B) at least one further agrochemically active compound
for controlling animal pests, such as insects and/or unwanted acarids and/or nematodes in transgenic crops and/or increasing crop yield in those crops.

In a preferred embodiment the invention also relates to the use of compositions comprising A) a mixture of compound (I-1-2)/(I-1-8) and
B) at least one further agrochemically active compound
for controlling animal pests, such as insects and/or unwanted acarids and/or nematodes in transgenic crops and/or increasing crop yield in those crops.

In the present context, agrochemically active compounds are to be understood as meaning all substances which are or may be customarily used for treating plants. Fungicides, bactericides, insecticides, acaricides, nematicides, molluscicides, safeners, plant growth regulators and plant nutrients may be mentioned as being preferred.

Mixing Partners

The agrochemically active compound described under B) are the following active ingredients being insecticides which may be mentioned are:

(1) Acetylcholinesterase (AChE) inhibitors, for example
carbamates, e.g. Alanycarb (II-1-1), Aldicarb (II-1-2), Bendiocarb (II-1-3), Benfuracarb (II-1-4), Butocarboxim (II-1-5), Butoxycarboxim (II-1-6), Carbaryl (II-1-7), Carbofuran (II-1-8), Carbosulfan (II-1-9), Ethiofencarb (II-1-10), Fenobucarb (II-1-11), Formetanate (II-1-12), Furathiocarb (II-1-13), Isoprocarb (II-1-14), Methiocarb (II-1-15), Methomyl (II-1-16), Metolcarb (II-1-17), Oxamyl (II-1-18), Pirimicarb (II-1-19), Propoxur (II-1-20), Thiodicarb (II-1-21), Thiofanox (II-1-22), Triazamate (II-1-23), Trimethacarb (II-1-24), XMC (II-1-25), and Xylylcarb (II-1-26); or
organophosphates, e.g. Acephate (II-1-27), Azamethiphos (II-1-28), Azinphos-ethyl (II-1-29), Azinphos-methyl (II-1-30), Cadusafos (II-1-31), Chlorethoxyfos (II-1-32), Chlorfenvinphos (II-1-33), Chlormephos (II-1-34), Chlorpyrifos (II-1-35), Chlorpyrifos-methyl (II-1-36), Coumaphos (II-1-37), Cyanophos (II-1-38), Demeton-S-methyl (II-1-39), Diazinon (II-1-40), Dichlorvos/DDVP (II-1-41), Dicrotophos (II-1-42), Dimethoate (II-1-43), Dimethylvinphos (II-1-44), Disulfoton (II-1-45), EPN (II-1-46), Ethion (II-1-47), Ethoprophos (II-1-48), Famphur (II-1-49), Fenamiphos (II-1-50), Fenitrothion (II-1-51), Fenthion (II-1-52), Fosthiazate (II-1-53), Heptenophos (II-1-54), Imicyafos (II-1-55), Isofenphos (II-1-56), Isopropyl O-(methoxyaminothio-phosphoryl) salicylate (II-1-57), Isoxathion (II-1-58), Malathion (II-1-59), Mecarbam (II-1-60), Methamidophos (II-1-61), Methidathion (II-1-62), Mevinphos (II-1-63), Monocrotophos (II-1-64), Naled (II-1-65), Omethoate (II-1-66), Oxydemeton-methyl (II-1-67), Parathion (II-1-68), Parathion-methyl (II-1-69), Phenthoate (II-1-70), Phorate (II-1-71), Phosalone (II-1-72), Phosmet (II-1-73), Phosphamidon (II-1-74), Phoxim (II-1-75), Pirimiphos-methyl (II-1-76), Profenofos (II-1-77), Propetamphos (II-1-78), Prothiofos (II-1-79), Pyraclofos (II-1-80), Pyridaphenthion (II-1-81), Quinalphos (II-1-82), Sulfotep (II-1-83), Tebupirimfos (II-1-84), Temephos (II-1-85), Terbufos (II-1-86), Tetrachlorvinphos (II-1-87), Thiometon (II-1-88), Triazophos (II-1-89), Trichlorfon (II-1-90), and Vamidothion (II-1-91).

(2) GABA-gated chloride channel antagonists, for example
cyclodiene organochlorines, e.g. Chlordane (II-2-1) and Endosulfan (II-2-2); or
phenylpyrazoles (fiproles), e.g. Ethiprole (II-2-3) and Fipronil (II-2-4).

(3) Sodium channel modulators/voltage-dependent sodium channel blockers, for example
pyrethroids, e.g. Acrinathrin (II-3-1), Allethrin (II-3-2), d-cis-trans Allethrin (II-3-3), d-trans Allethrin (II-3-4), Bifenthrin (II-3-5), Bioallethrin (II-3-6), Bioallethrin S-cyclopentenyl isomer (II-3-7), Bioresmethrin (II-3-8), Cycloprothrin (II-3-9), Cyfluthrin (II-3-10), beta-Cyfluthrin (II-3-11), Cyhalothrin (II-3-12), lambda-Cyhalothrin (II-3-13), gamma-Cyhalothrin (II-3-14), Cypermethrin (II-3-15), alpha-Cypermethrin (II-3-16), beta-Cypermethrin (II-3-17), theta-Cypermethrin (II-3-18), zeta-Cypermethrin (II-3-19), Cyphenothrin [(1R)-trans isomers] (II-3-20), Deltamethrin (II-3-21), Empenthrin [(EZ)-(1R) isomers) (II-3-22), Esfenvalerate (II-3-23), Etofenprox (II-3-24), Fenpropathrin (II-3-25), Fenvalerate (II-3-26), Flucythrinate (II-3-27), Flumethrin (II-3-28), tau-Fluvalinate (II-3-29), Halfenprox (II-3-30), Imiprothrin (II-3-31), Kadethrin (II-3-32), Permethrin (II-3-33), Phenothrin [(1R)-trans isomer) (II-3-34), Prallethrin (II-3-35), Pyrethrine (pyrethrum) (II-3-36), Resmethrin (II-3-37), Silafluofen (II-3-38), Tefluthrin (II-3-39), Tetramethrin (II-3-40), Tetramethrin [(1R) isomers)] (II-3-41), Tralomethrin (II-3-42), and Transfluthrin (II-3-43); or
DDT (II-3-44); or Methoxychlor (II-3-45).

(4) Nicotinic acetylcholine receptor (nAChR) agonists, for example
neonicotinoids, e.g. Acetamiprid (II-4-1), Clothianidin (II-4-2), Dinotefuran (II-4-3), Imidacloprid (II-4-4), Nitenpyram (II-4-5), Thiacloprid (II-4-6), and Thiamethoxam (II-4-7); or
Nicotine (II-4-8).

(5) Nicotinic acetylcholine receptor (nAChR) allosteric activators, for example
spinosyns, e.g. Spinetoram (II-5-1) and Spinosad (II-5-2).

(6) Chloride channel activators, for example
avermectins/milbemycins, e.g. Abamectin (II-6-1), Emamectin benzoate (II-6-2), Lepimectin (II-6-3), and Milbemectin (II-6-4).

(7) Juvenile hormone mimics, for example
juvenile hormone analogues, e.g. Hydroprene (II-7-1), Kinoprene (II-7-2), and Methoprene (II-7-3); or
Fenoxycarb (II-7-4); or Pyriproxyfen (II-7-5).

(8) Miscellaneous non-specific (multi-site) inhibitors, for example
alkyl halides, e.g. Methyl bromide (II-8-1) and other alkyl halides; or
Chloropicrin (II-8-2); or Sulfuryl fluoride (II-8-3); or Borax (II-8-4); or Tartar emetic (II-8-5).

(9) Selective homopteran feeding blockers, e.g. Pymetrozine (II-9-1); or Flonicamid (II-9-2).

(10) Mite growth inhibitors, e.g. Clofentezine (II-10-1), Hexythiazox (II-10-2), and Diflovidazin (II-10-3); or
Etoxazole (II-10-4).

(11) Microbial disruptors of insect midgut membranes, e.g. *Bacillus thuringiensis* subspecies *israelensis* (II-11-1), *Bacillus sphaericus* (II-11-2), *Bacillus thuringiensis* subspecies *aizawai* (II-11-3), *Bacillus thuringiensis* subspecies *kurstaki* (II-11-4), *Bacillus thuringiensis* subspecies *tenebrionis* (II-11-5), and BT crop proteins: Cry1Ab, Cry1Ac, Cry1Fa, Cry2Ab, mCry3A, Cry3Ab, Cry3Bb, Cry34/35Ab1 (II-11-6).

(12) Inhibitors of mitochondrial ATP synthase, for example Diafenthiuron (II-12-1); or
organotin miticides, e.g. Azocyclotin (II-12-2), Cyhexatin (II-12-3), and Fenbutatin oxide (II-12-4); or
Propargite (II-12-5); or Tetradifon (II-12-6).

(13) Uncouplers of oxidative phoshorylation via disruption of the proton gradient, for example Chlorfenapyr (II-13-1), DNOC (II-13-2), and Sulfluramid (II-13-3).

(14) Nicotinic acetylcholine receptor (nAChR) channel blockers, for example Bensultap (II-14-1), Cartap hydrochloride (II-14-2), Thiocyclam (II-14-3), and Thiosultap-sodium (II-14-4).

(15) Inhibitors of chitin biosynthesis, type 0, for example Bistrifluron (II-15-1), Chlorfluazuron (II-15-2), Diflubenzuron (II-15-3), Flucycloxuron (II-15-4), Flufenoxuron (II-15-5), Hexaflumuron (II-15-6), Lufenuron (II-15-7), Novaluron (II-15-8), Noviflumuron (II-15-9), Teflubenzuron (II-15-10), and Triflumuron (II-15-11).

(16) Inhibitors of chitin biosynthesis, type 1, for example Buprofezin (II-16-1).

(17) Moulting disruptors, for example Cyromazine (II-17-1).

(18) Ecdysone receptor agonists, for example Chromafenozide (II-18-1), Halofenozide (II-18-2), Methoxyfenozide (II-18-3), and Tebufenozide (II-18-4).

(19) Octopamine receptor agonists, for example Amitraz (II-19-1).

(20) Mitochondrial complex III electron transport inhibitors, for example Hydramethylnon (II-20-1); or Acequinocyl (II-20-2); or Fluacrypyrim (II-20-3).

(21) Mitochondrial complex I electron transport inhibitors, for example
METI acaricides, e.g. Fenazaquin (II-21-1), Fenpyroximate (II-21-2), Pyrimidifen (II-21-3), Pyridaben (II-21-4), Tebufenpyrad (II-21-5), and Tolfenpyrad (II-21-6); or
Rotenone (Derris) (II-21-7).

(22) Voltage-dependent sodium channel blockers, e.g. Indoxacarb (II-22-1); or Metaflumizone (II-22-2).

(23) Inhibitors of acetyl CoA carboxylase, for example
tetronic and tetramic acid derivatives, e.g. Spirodiclofen (II-23-1), Spiromesifen (II-23-2), and Spirotetramat (II-23-3).

(24) Mitochondrial complex IV electron transport inhibitors, for example
phosphines, e.g. Aluminium phosphide (II-24-1), Calcium phosphide (II-24-2), Phosphine (II-24-3), and Zinc phosphide (II-24-4); or
Cyanide (II-24-5).

(25) Mitochondrial complex II electron transport inhibitors, for example Cyenopyrafen (II-25-1).

(28) Ryanodine receptor modulators, for example
diamides, e.g. Chlorantraniliprole (II-28-1) and Flubendiamide (II-28-2).

Further active ingredients with unknown or uncertain mode of action, for example Amidoflumet (II-29-1), Azadirachtin (II-29-2), Benclothiaz (II-29-3), Benzoximate (II-29-4), Bifenazate (II-29-5), Bromopropylate (II-29-6), Chinomethionat (II-29-7), Cryolite (II-29-8), Cyantraniliprole (Cyazypyr) (II-29-9), Cyflumetofen (II-29-10), Dicofol (II-29-11), Diflovidazin (II-29-12), Fluensulfone (II-29-13), Flufenerim (II-29-14), Flufiprole (II-29-15), Fluopyram (II-29-16), Fufenozide (II-29-17), Imidaclothiz (II-29-18), Iprodione (II-29-19), Meperfluthrin (II-29-20), Pyridalyl (II-29-21), Pyrifluquinazon (II-29-22), Tetramethylfluthrin (II-29-23), and iodomethane (II-29-24); furthermore products based on *Bacillus firmus* (including but not limited to strain CNCM I-1582, such as, for example, VOTiVO™, BioNem) (II-29-25) or one of the following known active compounds:
3-bromo-N-{2-bromo-4-chloro-6-[(1-cyclopropylethyl)carbamoyl]phenyl}-1-(3-chloropyridin-2-yl)-1H-pyrazole-5-carboxamide (II-29-26) (known from WO2005/077934), 4-{[(6-bromopyridin-3-yl)methyl](2-fluoroethyl)
amino}furan-2(5H)-one (II-29-27) (known from WO2007/115644), 4-{[(6-fluoropyridin-3-yl)methyl](2,2-difluoroethyl)amino}furan-2(5H)-one (II-29-28) (known from WO2007/115644), 4-{[(2-chloro-1,3-thiazol-5-yl)methyl](2-fluoroethyl)amino}furan-2(5H)-one (II-29-29) (known from WO2007/115644), 4-{[(6-chloropyridin-3-yl)methyl](2-fluoroethyl)amino}furan-2(5H)-one (II-29-30) (known from WO2007/115644), Flupyradifurone (II-29-31), 4-{[(6-chlor-5-fluoropyridin-3-yl)methyl](methyl)amino}furan-2(5H)-one (II-29-32) (known from WO2007/115643), 4-{[(5,6-dichloropyridin-3-yl)methyl](2-fluoroethyl)amino}furan-2(5H)-one (II-29-33) (known from WO2007/115646), 4-{[(6-chloro-5-fluoropyridin-3-yl)methyl](cyclopropyl)amino}furan-2(5H)-one (II-29-34) (known from WO2007/115643), 4-{[(6-chloropyridin-3-yl)methyl](cyclopropyl)amino}furan-2(5H)-one (II-29-35) (known from EP-A-0 539 588), 4-{[(6-chlorpyridin-3-yl)methyl](methyl)amino}furan-2(5H)-one (II-29-36) (known from EP-A-0 539 588), {[1-(6-chloropyridin-3-yl)ethyl](methyl)oxido-$\lambda^4$-sulfanylidene}cyanamide (II-29-37) (known from WO2007/149134) and its diastereomers {[(1R)-1-(6-chloropyridin-3-yl)ethyl](methyl)oxido-$\lambda^4$-sulfanylidene}cyanamide (A) (II-29-38), and {[(1S)-1-(6-chloropyridin-3-yl)ethyl](methyl)oxido-$\lambda^4$-sulfanylidene}cyanamide (B) (II-29-39) (also known from WO2007/149134) as well as Sulfoxaflor (II-29-40) and its diastereomers [(R)-methyl(oxido){(1R)-1-[6-(trifluoromethyl)pyridin-3-yl]ethyl}-$\lambda^4$-sulfanylidene]cyanamide (A1) (II-29-41), and [(S)-methyl(oxido) {(1S)-1-[6-(trifluoromethyl)pyridin-3-yl]ethyl}-$\lambda^4$-sulfanylidene]
cyanamide (A2) (II-29-42), referred to as group of diastereomers A (known from WO2010/074747, WO2010/074751), [(R)-methyl(oxido){(1S)-1-[6-(trifluoromethyl)pyridin-3-yl]ethyl}-$\lambda^4$-sulfanylidene]cyanamide (B1) (II-29-43), and [(S)-methyl(oxido) {(1R)-1-[6-(trifluoromethyl)pyridin-3-yl]ethyl}-$\lambda^4$-sulfanylidene]cyanamide (B2) (II-29-44), referred to as group of diastereomers B (also known from WO2010/074747, WO2010/074751), and 11-(4-chloro-2,6-dimethylphenyl)-12-hydroxy-1,4-dioxa-9-azadispiro[4.2.4.2]tetradec-11-en-10-one (II-29-45) (known from WO2006/089633), 3-(4'-fluoro-2,4-dimethylbiphenyl-3-yl)-4-hydroxy-8-oxa-1-azaspiro[4.5]dec-3-en-2-one (II-29-46) (known from WO2008/067911), 1-{2-fluoro-4-methyl-5-[(2,2,2-trifluorethyl)sulfinyl]phenyl}-3-(trifluoromethyl)-1H-1,2,4-triazol-5-amine (II-29-47) (known from WO2006/043635), [(3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H,11H-benzo[f]pyrano[4,3-b]chromen-4-yl] methyl cyclopropanecarboxylate (II-29-48) (known from WO2008/066153), 2-cyano-3-(difluoromethoxy)-N,N-dimethylbenzenesulfonamide (II-29-49) (known from WO2006/056433), 2-cyano-3-(difluoromethoxy)-N-methylbenzenesulfonamide (II-29-50) (known from WO2006/100288), 2-cyano-3-(difluoromethoxy)-N-ethylbenzenesulfonamide (II-29-51) (known from WO2005/035486), 4-(difluoromethoxy)-N-ethyl-N-methyl-1,2-benzothiazol-3-amine 1,1-dioxide (II-29-52) (known from WO2007/057407), N-[1-(2,3-dimethylphenyl)-2-(3,5-dimethylphenyl)ethyl]-4,5-dihydro-1,3-thiazol-2-amine (II-29-53) (known from WO2008/104503), {1'-(2E)-3-(4-chlorophenyl)prop-2-en-1-yl]-5-fluorospiro[indole-3,4'-piperidin]-1(2H)-yl}(2-chloropyridin-4-yl)methanone (II-29-54) (known from WO2003/106457), 3-(2,5-dimethylphenyl)-4-hydroxy-8-methoxy-1,8-diazaspiro[4.5]dec-3-en-2-one (II-29-55) (known from WO2009/049851), 3-(2,5-dimethylphenyl)-8-methoxy-2-oxo-1,8-diazaspiro[4.5]dec-3-en-4-yl ethyl carbonate (II-29-56) (known from WO2009/049851), 4-(but-2-yn-1-yloxy)-6-(3,5-dimethylpiperidin-1-yl)-5-fluoropyrimidine (II-29-57) (known from WO2004/099160), (2,2,3,3,4,4,5,5-octafluoropentyl)(3,3,3-trifluoropropyl)malononitrile (II-29-58) (known from WO2005/063094), (2,2,3,3,4,4,5,5-octafluoropentyl)(3,3,4,4,4-pentafluorobutyl)malononitrile (II-29-59) (known from WO2005/063094), 8-[2-(cyclopropylmethoxy)-4-(trifluoromethyl)phenoxy]-3-[6-(trifluoromethyl)pyridazin-3-yl]-3-azabicyclo[3.2.1]octane (II-29-60) (known from WO2007/040280), Flometoquin (II-29-61), PF1364 (CAS-Reg. No. 1204776-60-2) (II-29-62) (known from JP2010/018586), 5-[5-(3,5-dichlorophenyl)-5-(trifluoromethyl)-4,5-dihydro-1,2-oxazol-3-yl]-2-(1H-1,2,4-triazol-1-yl)benzonitrile (II-29-63) (known from WO2007/075459), 5-[5-(2-chloropyridin-4-yl)-5-(trifluoromethyl)-4,5-dihydro-1,2-oxazol-3-yl]-2-(1H-1,2,4-triazol-1-yl)

benzonitrile (II-29-64) (known from WO2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (II-29-65) (known from WO2005/085216), 4-{[(6-chloropyridin-3-yl)methyl](cyclopropyl)amino}-1,3-oxazol-2(5H)-one (II-29-66), 4-{[(6-chloropyridin-3-yl)methyl](2,2-difluoroethyl)amino}-1,3-oxazol-2(5H)-one (II-29-67), 4-{[(6-chloropyridin-3-yl)methyl](ethyl)amino}-1,3-oxazol-2(5H)-one (II-29-68), 4-{[(6-chloropyridin-3-yl)methyl](methyl)amino}-1,3-oxazol-2(5H)-one (II-29-69) (all known from WO2010/005692), NNI-0711 (II-29-70) (known from WO2002/096882), 1-acetyl-N-[4-(1,1,1,3,3,3-hexafluoro-2-methoxypropan-2-yl)-3-isobutylphenyl]-N-isobutyryl-3,5-dimethyl-1H-pyrazole-4-carboxamide (II-29-71) (known from WO2002/096882), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (II-29-72) (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (II-29-73) (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (II-29-74) (known from WO2005/085216), methyl 2-[3,5-dibromo-2-({[3-bromo-1-(3-chloropyridin-2-yl)-1H-pyrazol-5-yl]carbonyl}amino)benzoyl]-1,2-diethylhydrazinecarboxylate (II-29-75) (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (II-29-76) (known from WO2005/085216), (5RS,7RS;5RS,7SR)-1-(6-chloro-3-pyridylmethyl)-1,2,3,5,6,7-hexahydro-7-methyl-8-nitro-5-propoxyimidazo[1,2-a]pyridine (II-29-77) (known from WO2007/101369), 2-{6-[2-(5-fluoropyridin-3-yl)-1,3-thiazol-5-yl]pyridin-2-yl}pyrimidine (II-29-78) (known from WO2010/006713), 2-{6-[2-(pyridin-3-yl)-1,3-thiazol-5-yl]pyridin-2-yl}pyrimidine (II-29-79) (known from WO2010/006713), (1E)-N-[(6-chloropyridin-3-yl)methyl]-N'-cyano-N-(2,2-difluoroethyl)ethanimidamide (II-29-84) (known from WO2008/009360), N-[2-(5-amino-1,3,4-thiadiazol-2-yl)-4-chloro-6-methylphenyl]-3-bromo-1-(3-chloropyridin-2-yl)-1H-pyrazole-5-carboxamide (II-29-85) (known from CN102057925), and methyl 2-[3,5-dibromo-2-({[3-bromo-1-(3-chloropyridin-2-yl)-1H-pyrazol-5-yl]carbonyl}amino)benzoyl]-2-ethyl-1-methylhydrazinecarboxylate (II-29-86) (known from WO2011/049233);

being fungicides which may be mentioned are:

(1) Inhibitors of the ergosterol biosynthesis, for example (1.1) aldimorph (1704-28-5), (1.2) azaconazole (60207-31-0), (1.3) bitertanol (55179-31-2), (1.4) bromuconazole (116255-48-2), (1.5) cyproconazole (113096-99-4), (1.6) diclobutrazole (75736-33-3), (1.7) difenoconazole (119446-68-3), (1.8) diniconazole (83657-24-3), (1.9) diniconazole-M (83657-18-5), (1.10) dodemorph (1593-77-7), (1.11) dodemorph acetate (31717-87-0), (1.12) epoxiconazole (106325-08-0), (1.13) etaconazole (60207-93-4), (1.14) fenarimol (60168-88-9), (1.15) fenbuconazole (114369-43-6), (1.16) fenhexamid (126833-17-8), (1.17) fenpropidin (67306-00-7), (1.18) fenpropimorph (67306-03-0), (1.19) fluquinconazole (136426-54-5), (1.20) flurprimidol (56425-91-3), (1.21) flusilazole (85509-19-9), (1.22) flutriafol (76674-21-0), (1.23) furconazole (112839-33-5), (1.24) furconazole-cis (112839-32-4), (1.25) hexaconazole (79983-71-4), (1.26) imazalil (60534-80-7), (1.27) imazalil sulfate (58594-72-2), (1.28) imibenconazole (86598-92-7), (1.29) ipconazole (125225-28-7), (1.30) metconazole (125116-23-6), (1.31) myclobutanil (88671-89-0), (1.32) naftifine (65472-88-0), (1.33) nuarimol (63284-71-9), (1.34) oxpoconazole (174212-12-5), (1.35) paclobutrazol (76738-62-0), (1.36) pefurazoate (101903-30-4), (1.37) penconazole (66246-88-6), (1.38) piperalin (3478-94-2), (1.39) prochloraz (67747-09-5), (1.40) propiconazole (60207-90-1), (1.41) prothioconazole (178928-70-6), (1.42) pyributicarb (88678-67-5), (1.43) pyrifenox (88283-41-4), (1.44) quinconazole (103970-75-8), (1.45) simeconazole (149508-90-7), (1.46) spiroxamine (118134-30-8), (1.47) tebuconazole (107534-96-3), (1.48) terbinafine (91161-71-6), (1.49) tetraconazole (112281-77-3), (1.50) triadimefon (43121-43-3), (1.51) triadimenol (89482-17-7), (1.52) tridemorph (81412-43-3), (1.53) triflumizole (68694-11-1), (1.54) triforine (26644-46-2), (1.55) triticonazole (131983-72-7), (1.56) uniconazole (83657-22-1), (1.57) uniconazole-p (83657-17-4), (1.58) viniconazole (77174-66-4), (1.59) voriconazole (137234-62-9), (1.60) 1-(4-chlorophenyl)-2-(1H-1,2,4-triazol-1-yl)cycloheptanol (129586-32-9), (1.61) methyl 1-(2,2-dimethyl-2,3-dihydro-1H-inden-1-yl)-1H-imidazole-5-carboxylate (110323-95-0), (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide and (1.64) O-[1-(4-methoxyphenoxy)-3,3-dimethylbutan-2-yl]1H-imidazole-1-carbothioate (111226-71-2).

(2) inhibitors of the respiratory chain at complex I or II, for example (2.1) bixafen (581809-46-3), (2.2) boscalid (188425-85-6), (2.3) carboxin (5234-68-4), (2.4) diflumetorim (130339-07-0), (2.5) fenfuram (24691-80-5), (2.6) fluopyram (658066-35-4), (2.7) flutolanil (66332-96-5), (2.8) fluxapyroxad (907204-31-3), (2.9) furametpyr (123572-88-3), (2.10) furmecyclox (60568-05-0), (2.11) isopyrazam (mixture of syn-epimeric racemate 1RS,4SR,9RS and anti-epimeric racemate 1RS,4SR,9SR) (881685-58-1), (2.12) isopyrazam (anti-epimeric racemate 1RS,4SR,9SR), (2.13) isopyrazam (anti-epimeric enantiomer 1R,4S,9S), (2.14) isopyrazam (anti-epimeric enantiomer 1S,4R,9R), (2.15) isopyrazam (syn epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil (55814-41-0), (2.19) oxycarboxin (5259-88-1), (2.20) penflufen (494793-67-8), (2.21) penthiopyrad (183675-82-3), (2.22) sedaxane (874967-67-6), (2.23) thifluzamide (130000-40-7), (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide (1092400-95-7) (WO 2008148570), (2.28) 5,8-difluoro-N-[2-(2-fluoro-4-{[4-(trifluoromethyl)pyridin-2-yl]oxy}phenyl)ethyl]quinazolin-4-amine (1210070-84-0) (WO2010025451), (2.29) N-[9-(dichloromethylene)-1,2,3,4-tetrahydro-1,4-methanonaphthalen-5-yl]-3-(difluoromethyl)-1-methyl-1H-pyrazole-4-carboxamide, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide.

(3) inhibitors of the respiratory chain at complex III, for example (3.1) ametoctradin (865318-97-4), (3.2) amisulbrom (348635-87-0), (3.3) azoxystrobin (131860-33-8), (3.4) cyazofamid (120116-88-3), (3.5) coumethoxystrobin (850881-30-0), (3.6) coumoxystrobin (850881-70-8), (3.7) dimoxystrobin (141600-52-4), (3.8) enestroburin (238410-11-2) (WO 2004/058723), (3.9) famoxadone (131807-57-3) (WO 2004/058723), (3.10) fenamidone (161326-34-7) (WO 2004/058723), (3.11) fenoxystrobin (918162-02-4), (3.12) fluoxastrobin (361377-29-9) (WO 2004/058723), (3.13) kresoxim-methyl (143390-89-0) (WO 2004/058723), (3.14) metominostrobin (133408-50-1) (WO 2004/058723), (3.15) orysastrobin (189892-69-1) (WO 2004/058723), (3.16) picoxystrobin (117428-22-5) (WO 2004/058723), (3.17) pyraclostrobin (175013-18-0) (WO 2004/058723), (3.18) pyrametostrobin (915410-70-7) (WO 2004/058723), (3.19) pyraoxystrobin (862588-11-2) (WO 2004/058723), (3.20) pyribencarb (799247-52-2) (WO 2004/058723), (3.21) triclopyricarb (902760-40-1), (3.22) trifloxystrobin (141517-21-7) (WO 2004/058723), (3.23) (2E)-2-(2-{[6-(3-chloro-2-methylphenoxy)-5-fluoropyrimidin-4-yl]oxy}phenyl)-2-(methoxyimino)-N-methylethanamide (WO 2004/058723), (3.24) (2E)-2-(methoxyimino)-N-methyl-2-(2-{[({(1E)-1-[3-(trifluoromethyl)phenyl]ethylidene}amino)oxy]methyl}phenyl)ethanamide (WO 2004/058723), (3.25) (2E)-2-(methoxyimino)-N-methyl-2-{2-[(E)-({1-[3-(trifluoromethyl)phenyl]ethoxy}imino)methyl]phenyl}ethanamide (158169-73-4), (3.26) (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide (326896-28-0), (3.27) (2E)-2-{2-[({[(2E,3E)-4-(2,6-dichlorophenyl)but-3-en-2-ylidene]amino}oxy)methyl]phenyl}-2-(methoxyimino)-N-methylethanamide, (3.28) 2-chloro-N-(1,1,3-trimethyl-2,3-dihydro-1H-inden-4-yl)pyridine-3-carboxamide (119899-14-8), (3.29) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.30) methyl (2E)-2-{2-[{(cyclopropyl[(4-methoxyphenyl)imino]methyl}sulfanyl)methyl]phenyl}-3-methoxyprop-2-enoate (149601-03-6), (3.31) N-(3-ethyl-3,5,5-trimethylcyclohexyl)-3-(formylamino)-2-hydroxybenzamide (226551-21-9), (3.32) 2-{2-[(2,5-dimethylphenoxy)methyl]phenyl}-2-methoxy-N-methylacetamide (173662-97-0) and (3.33) (2R)-2-{2-[(2,5-dimethylphenoxy)methyl]phenyl}-2-methoxy-N-methylacetamide (394657-24-0).

(4) Inhibitors of the mitosis and cell division, for example (4.1) benomyl (17804-35-2), (4.2) carbendazim (10605-21-7), (4.3) chlorfenazole (3574-96-7), (4.4) diethofencarb (87130-20-9), (4.5) ethaboxam (162650-77-3), (4.6) fluopicolide (239110-15-7), (4.7) fuberidazole (3878-19-1), (4.8) pencycuron (66063-05-6), (4.9) thiabendazole (148-79-8), (4.10) thiophanate-methyl (23564-05-8), (4.11) thiophanate (23564-06-9), (4.12) zoxamide (156052-68-5), (4.13) 5-chloro-7-(4-methylpiperidin-1-yl)-6-(2,4,6-trifluorophenyl)[1,2,4]triazolo[1,5-a]pyrimidine (214706-53-3) and (4.14) 3-chloro-5-(6-chloropyridin-3-yl)-6-methyl-4-(2,4,6-trifluorophenyl)pyridazine (1002756-87-7).

(5) Compounds capable to have a multisite action, like for example (5.1) bordeaux mixture (8011-63-0), (5.2) captafol (2425-06-1), (5.3) captan (133-06-2) (WO 02/12172), (5.4) chlorothalonil (1897-45-6), (5.5) copper hydroxide (20427-59-2), (5.6) copper naphthenate (1338-02-9), (5.7) copper oxide (1317-39-1), (5.8) copper oxychloride (1332-40-7), (5.9) copper(2+) sulfate (7758-98-7), (5.10) dichlofluanid (1085-98-9), (5.11) dithianon (3347-22-6), (5.12) dodine (2439-10-3), (5.13) dodine free base, (5.14) ferbam (14484-64-1), (5.15) fluorofolpet (719-96-0), (5.16) folpet (133-07-3), (5.17) guazatine (108173-90-6), (5.18) guazatine acetate, (5.19) iminoctadine (13516-27-3), (5.20) iminoctadine albesilate (169202-06-6), (5.21) iminoctadine triacetate (57520-17-9), (5.22) mancopper (53988-93-5), (5.23) mancozeb (8018-01-7), (5.24) maneb (12427-38-2), (5.25) metiram (9006-42-2), (5.26) metiram zinc (9006-42-2), (5.27) oxinecopper (10380-28-6), (5.28) propamidine (104-32-5), (5.29) propineb (12071-83-9), (5.30) sulphur and sulphur preparations including calcium polysulphide (7704-34-9), (5.31) thiram (137-26-8), (5.32) tolylfluanid (731-27-1), (5.33) zineb (12122-67-7) and (5.34) ziram (137-30-4).

(6) Compounds capable to induce a host defence, for example (6.1) acibenzolar-S-methyl (135158-54-2), (6.2) isotianil (224049-04-1), (6.3) probenazole (27605-76-1) and (6.4) tiadinil (223580-51-6).

(7) Inhibitors of the amino acid and/or protein biosynthesis, for example (7.1) andoprim (23951-85-1), (7.2) blasticidin-S (2079-00-7), (7.3) cyprodinil (121552-61-2), (7.4) kasugamycin (6980-18-3), (7.5) kasugamycin hydrochloride hydrate (19408-46-9), (7.6) mepanipyrim (110235-47-7), (7.7) pyrimethanil (53112-28-0) and (7.8) 3-(5-fluoro-3,3,4,4-tetramethyl-3,4-dihydroisoquinolin-1-yl)quinoline (861647-32-7) (WO2005070917).

(8) Inhibitors of the ATP production, for example (8.1) fentin acetate (900-95-8), (8.2) fentin chloride (639-58-7), (8.3) fentin hydroxide (76-87-9) and (8.4) silthiofam (175217-20-6).

(9) Inhibitors of the cell wall synthesis, for example (9.1) benthiavalicarb (177406-68-7), (9.2) dimethomorph (110488-70-5), (9.3) flumorph (211867-47-9), (9.4) iprovalicarb (140923-17-7), (9.5) mandipropamid (374726-62-2), (9.6) polyoxins (11113-80-7), (9.7) polyoxorim (22976-86-9), (9.8) validamycin A (37248-47-8) and (9.9) valifenalate (283159-94-4; 283159-90-0).

(10) Inhibitors of the lipid and membrane synthesis, for example (10.1) biphenyl (92-52-4), (10.2) chloroneb (2675-77-6), (10.3) dicloran (99-30-9), (10.4) edifenphos (17109-49-8), (10.5) etridiazole (2593-15-9), (10.6) iodocarb (55406-53-6), (10.7) iprobenfos (26087-47-8), (10.8) isoprothiolane (50512-35-1), (10.9) propamocarb (25606-41-1), (10.10) propamocarb hydrochloride (25606-41-1), (10.11) prothiocarb (19622-08-3), (10.12) pyrazophos (13457-18-6), (10.13) quintozene (82-68-8), (10.14) tecnazene (117-18-0) and (10.15) tolclofos-methyl (57018-04-9).

(11) Inhibitors of the melanine biosynthesis, for example (11.1) carpropamid (104030-54-8), (11.2) diclocymet (139920-32-4), (11.3) fenoxanil (115852-48-7), (11.4) phthalide (27355-22-2), (11.5) pyroquilon (57369-32-1), (11.6) tricyclazole (41814-78-2) and (11.7) 2,2,2-trifluoroethyl {3-methyl-1-[(4-methylbenzoyl)amino]butan-2-yl}carbamate (851524-22-6) (WO2005042474).

(12) Inhibitors of the nucleic acid synthesis, for example (12.1) benalaxyl (71626-11-4), (12.2) benalaxyl-M (kiralaxyl) (98243-83-5), (12.3) bupirimate (41483-43-6), (12.4) clozylacon (67932-85-8), (12.5) dimethirimol (5221-53-4), (12.6) ethirimol (23947-60-6), (12.7) furalaxyl (57646-30-7), (12.8) hymexazol (10004-44-1), (12.9) metalaxyl (57837-19-1), (12.10) metalaxyl-M (mefenoxam) (70630-17-0), (12.11) ofurace (58810-48-3), (12.12) oxadixyl (77732-09-3) and (12.13) oxolinic acid (14698-29-4).

(13) Inhibitors of the signal transduction, for example (13.1) chlozolinate (84332-86-5), (13.2) fenpiclonil (74738-17-3), (13.3) fludioxonil (131341-86-1), (13.4) iprodione (36734-19-7), (13.5) procymidone (32809-16-8), (13.6) quinoxyfen (124495-18-7) and (13.7) vinclozolin (50471-44-8).

(14) Compounds capable to act as an uncoupler, for example (14.1) binapacryl (485-31-4), (14.2) dinocap (131-72-6), (14.3) ferimzone (89269-64-7), (14.4) fluazinam (79622-59-6) and (14.5) meptyldinocap (131-72-6).

(15) Further compounds, for example (15.1) benthiazole (21564-17-0), (15.2) bethoxazin (163269-30-5), (15.3) capsimycin (70694-08-5), (15.4) carvone (99-49-0), (15.5) chinomethionat (2439-01-2), (15.6) pyriofenone (chlazafenone) (688046-61-9), (15.7) cufraneb (11096-18-7), (15.8) cyflufenamid (180409-60-3), (15.9) cymoxanil (57966-95-7), (15.10) cyprosulfamide (221667-31-8), (15.11) dazomet (533-74-4), (15.12) debacarb (62732-91-6), (15.13) dichlorophen (97-23-4), (15.14) diclomezine (62865-36-5), (15.15) difenzoquat (49866-87-7), (15.16) difenzoquat methylsulphate (43222-48-6), (15.17) diphenylamine (122-39-4), (15.18) ecomate, (15.19) fenpyrazamine (473798-59-3), (15.20) flumetover (154025-04-4), (15.21) fluoroimide (41205-21-4), (15.22) flusulfamide (106917-52-6), (15.23) flutianil (304900-25-2), (15.24) fosetyl-aluminium (39148-24-8), (15.25) fosetyl-calcium, (15.26) fosetyl-sodium (39148-16-8), (15.27) hexachlorobenzene (118-74-1), (15.28) irumamycin (81604-73-1), (15.29) methasulfocarb (66952-49-6), (15.30) methyl isothiocyanate (556-61-6), (15.31) metrafenone (220899-03-6), (15.32) mildiomycin (67527-71-3), (15.33) natamycin (7681-93-8), (15.34) nickel dimethyldithiocarbamate (15521-65-0), (15.35) nitrothal-isopropyl (10552-74-6), (15.36) octhilinone (26530-20-1), (15.37) oxamocarb (917242-12-7), (15.38) oxyfenthiin (34407-87-9), (15.39) pentachlorophenol and salts (87-86-5), (15.40) phenothrin, (15.41) phosphorous acid and its salts (13598-36-2), (15.42) propamocarb-fosetylate, (15.43) propanosine-sodium (88498-02-6), (15.44) proquinazid (189278-12-4), (15.45) pyrimorph (868390-90-3), (15.45e) (2E)-3-(4-tert-butylphenyl)-3-(2-chloropyridin-4-yl)-1-(morpholin-4-yl)prop-2-en-1-one (1231776-28-5), (15.45z) (2Z)-3-(4-tert-butylphenyl)-3-(2-chloropyridin-4-yl)-1-(morpholin-4-yl)prop-2-en-1-one (1231776-29-6), (15.46) pyrrolnitrine (1018-71-9) (EP-A 1 559 320), (15.47) tebufloquin (376645-78-2), (15.48) tecloftalam (76280-91-6), (15.49) tolnifanide (304911-98-6), (15.50) triazoxide (72459-58-6), (15.51) trichlamide (70193-21-4), (15.52) zarilamid (84527-51-5), (15.53) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate (517875-34-2) (WO2003035617), (15.54) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-79-6) (WO 2008013622), (15.55) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-80-9) (WO 2008013622), (15.56) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003318-67-9) (WO 2008013622), (15.57) 1-(4-methoxyphenoxy)-3,3-dimethylbutan-2-yl 1H-imidazole-1-carboxylate (111227-17-9), (15.58) 2,3,5,6-tetrachloro-4-(methylsulfonyl)pyridine (13108-52-6), (15.59) 2,3-dibutyl-6-chlorothieno[2,3-d]pyrimidin-4(3H)-one (221451-58-7), (15.60) 2,6-dimethyl-1H,5H-[1,4]dithiino[2,3-c:5,6-c'] dipyrrole-1,3,5,7(2H,6H)-tetrone, (15.61) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone (1003316-53-7) (WO 2008013622), (15.62) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone (1003316-54-8) (WO 2008013622), (15.63) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone (1003316-51-5) (WO 2008013622), (15.64) 2-butoxy-6-iodo-3-propyl-4H-chromen-4-one, (15.65) 2-chloro-5-[2-chloro-1-(2,6-difluoro-4-methoxyphenyl)-4-methyl-1H-imidazol-5-yl] pyridine, (15.66) 2-phenylphenol and salts (90-43-7), (15.67) 3-(4,4,5-trifluoro-3,3-dimethyl-3,4-dihydroisoquinolin-1-yl)quinoline (861647-85-0) (WO2005070917), (15.68) 3,4,5-trichloropyridine-2,6-dicarbonitrile (17824-85-0), (15.69) 3-[5-(4-chlorophenyl)-2,3-dimethyl-1,2-oxazolidin-3-yl]pyridine, (15.70) 3-chloro-5-(4-chlorophenyl)-4-(2,6-difluorophenyl)-6-methylpyridazine, (15.71) 4-(4-chlorophenyl)-5-(2,6-difluorophenyl)-3,6-dimethylpyridazine, (15.72) 5-amino-1,3,4-thiadiazole-2-thiol, (15.73) 5-chloro-N'-phenyl-N'-(prop-2-yn-1-yl)thiophene-2-sulfonohydrazide (134-31-6), (15.74) 5-fluoro-2-[(4-fluorobenzyl)oxy]pyrimidin-4-amine (1174376-11-4) (WO2009094442), (15.75) 5-fluoro-2-[(4-methylbenzyl)oxy]pyrimidin-4-amine (1174376-25-0) (WO2009094442), (15.76) 5-methyl-6-octyl[1,2,4]triazolo[1,5-a]pyrimidin-7-amine, (15.77) ethyl (2Z)-3-amino-2-cyano-3-phenylprop-2-enoate, (15.78) N'-(4-{[3-(4-chlorobenzyl)-1,2,4-thiadiazol-5-yl]oxy}-2,5-dimethylphenyl)-N-ethyl-N-methylimidoformamide, (15.79) N-(4-chlorobenzyl)-3-[3-methoxy-4-(prop-2-yn-1-yloxy)phenyl] propanamide, (15.80) N-[(4-chlorophenyl)(cyano)methyl]-3-[3-methoxy-4-(prop-2-yn-1-yloxy)phenyl]propanamide, (15.81) N-[(5-bromo-3-chloropyridin-2-yl)methyl]-2,4-dichloropyridine-3-carboxamide, (15.82) N-[1-(5-bromo-3-chloropyridin-2-yl)ethyl]-2,4-dichloropyridine-3-carboxamide, (15.83) N-[1-(5-bromo-3-chloropyridin-2-yl)ethyl]-2-fluoro-4-iodopyridine-3-carboxamide, (15.84) N-{(E)-[(cyclopropylmethoxy)imino][6-(difluoromethoxy)-2,3-difluorophenyl]methyl}-2-phenylacetamide (221201-92-9), (15.85) N-{(Z)-[(cyclopropylmethoxy)imino][6-(difluoromethoxy)-2,3-difluorophenyl]methyl}-2-phenylacetamide (221201-92-9), (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide (922514-49-6) (WO 2007014290), (15.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide (922514-07-6) (WO 2007014290), (15.89) N-methyl-2-(1-{[5-methyl-3-(trifluoromethyl)-1H-pyrazol-1-yl] acetyl}piperidin-4-yl)-N-[(1S)-1,2,3,4-tetrahydronaphthalen-1-yl]-1,3-thiazole-4-carboxamide (922514-48-5) (WO 2007014290), (15.90) pentyl {6-[({[(1-methyl-1H-tetrazol-5-yl)(phenyl)methylidene]amino}oxy) methyl]pyridin-2-yl}carbamate, (15.91) phenazine-1-carboxylic acid, (15.92) quinolin-8-ol (134-31-6), (15.93) quinolin-8-ol sulfate (2:1) (134-31-6) and (15.94) tert-butyl {6-[({[(1-methyl-1H-tetrazol-5-yl)(phenyl)methylene] amino}oxy)methyl]pyridin-2-yl}carbamate.

(16) Further compounds, for example (16.1) 1-methyl-3-(trifluoromethyl)-N-[2'-(trifluoromethyl)biphenyl-2-yl]-1H-pyrazole-4-carboxamide, (16.2) N-(4'-chlorobiphenyl-2-yl)-3-(difluoromethyl)-1-methyl-1H-pyrazole-4-carboxamide, (16.3) N-(2',4'-dichlorobiphenyl-2-yl)-3-(difluoromethyl)-1-methyl-1H-pyrazole-4-carboxamide, (16.4) 3-(difluoromethyl)-1-methyl-N-[4'-(trifluoromethyl)biphenyl-2-yl]-1H-pyrazole-4-carboxamide, (16.5) N-(2',5'-difluorobiphenyl-2-yl)-1-methyl-3-(trifluoromethyl)-1H-pyrazole-4-carboxamide, (16.6) 3-(difluoromethyl)-1-methyl-N-[4'-

(prop-1-yn-1-yl)biphenyl-2-yl]-1H-pyrazole-4-carboxamide (known from WO 2004/058723), (16.7) 5-fluoro-1,3-dimethyl-N-[4'-(prop-1-yn-1-yl)biphenyl-2-yl]-1H-pyrazole-4-carboxamide (known from WO 2004/058723), (16.8) 2-chloro-N-[4'-(prop-1-yn-1-yl)biphenyl-2-yl]pyridine-3-carboxamide (known from WO 2004/058723), (16.9) 3-(difluoromethyl)-N-[4'-(3,3-dimethylbut-1-yn-1-yl)biphenyl-2-yl]-1-methyl-1H-pyrazole-4-carboxamide (known from WO 2004/058723), (16.10) N-[4'-(3,3-dimethylbut-1-yn-1-yl)biphenyl-2-yl]-5-fluoro-1,3-dimethyl-1H-pyrazole-4-carboxamide (known from WO 2004/058723), (16.11) 3-(difluoromethyl)-N-(4'-ethynylbiphenyl-2-yl)-1-methyl-1H-pyrazole-4-carboxamide (known from WO 2004/058723), (16.12) N-(4'-ethynylbiphenyl-2-yl)-5-fluoro-1,3-dimethyl-1H-pyrazole-4-carboxamide (known from WO 2004/058723), (16.13) 2-chloro-N-(4'-ethynylbiphenyl-2-yl)pyridine-3-carboxamide (known from WO 2004/058723), (16.14) 2-chloro-N-[4'-(3,3-dimethylbut-1-yn-1-yl)biphenyl-2-yl]pyridine-3-carboxamide (known from WO 2004/058723), (16.15) 4-(difluoromethyl)-2-methyl-N-[4'-(trifluoromethyl)biphenyl-2-yl]-1,3-thiazole-5-carboxamide (known from WO 2004/058723), (16.16) 5-fluoro-N-[4'-(3-hydroxy-3-methylbut-1-yn-1-yl)biphenyl-2-yl]-1,3-dimethyl-1H-pyrazole-4-carboxamide (known from WO 2004/058723), (16.17) 2-chloro-N-[4'-(3-hydroxy-3-methylbut-1-yn-1-yl)biphenyl-2-yl]pyridine-3-carboxamide (known from WO 2004/058723), (16.18) 3-(difluoromethyl)-N-[4'-(3-methoxy-3-methylbut-1-yn-1-yl)biphenyl-2-yl]-1-methyl-1H-pyrazole-4-carboxamide (known from WO 2004/058723), (16.19) 5-fluoro-N-[4'-(3-methoxy-3-methylbut-1-yn-1-yl)biphenyl-2-yl]-1,3-dimethyl-1H-pyrazole-4-carboxamide (known from WO 2004/058723), (16.20) 2-chloro-N-[4'-(3-methoxy-3-methylbut-1-yn-1-yl)biphenyl-2-yl]pyridine-3-carboxamide (known from WO 2004/058723), (16.21) (5-bromo-2-methoxy-4-methylpyridin-3-yl)(2,3,4-trimethoxy-6-methylphenyl)methanone (known from EP-A 1 559 320), (16.22) N-[2-(4-{[3-(4-chlorophenyl)prop-2-yn-1-yl]oxy}-3-methoxyphenyl)ethyl]-N2-(methylsulfonyl)valinamide (220706-93-4), (16.23) 4-oxo-4-[(2-phenylethyl)amino]butanoic acid and (16.24) but-3-yn-1-yl {6-[{([(Z)-(1-methyl-1H-tetrazol-5-yl)(phenyl)methylene]amino}oxy)methyl]pyridin-2-yl}carbamate, N-[9-(dichloromethylene)-1,2,3,4-tetrahydro-1,4-methanonaphthalen-5-yl]-3-(difluoromethyl)-1-methyl-1H-pyrazole-4-carboxamide and 3-difluoromethyl-1-methyl-1H-pyrazole-4-carboxylic acid [2-(2,4-dichlorophenyl)-2-methoxy-1-methyl-ethyl]-amide.

Wherein all named mixing partners of the classes (1) to (16) can, if their functional groups enable this, optionally form salts with suitable bases or acids;

Being bactericides which may be mentioned are:

bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

being safeners which may be mentioned are:

(1) Heterocyclic carboxylic acid derivates, for example dichlorophenylpyrazolin-3-carboxylic acid derivatives, e.g. 1-(2,4-dichlorophenyl)-5-(ethoxycarbonyl)-5-methyl-4,5-dihydro-1H-pyrazole-3-carboxylic acid, diethyl 1-(2,4-dichlorophenyl)-4,5-dihydro-5-methyl-1H-pyrazole-3,5-dicarboxylate ("mefenpyr-diethyl"), and similar compounds known from WO 91/07874; for example dichlorophenylpyrazolecarboxylic acid derivatives, e.g. ethyl 1-(2,4-dichlorophenyl)-5-methyl-1H-pyrazole-3-carboxylate, ethyl 1-(2, 4-dichlorophenyl)-5-isopropyl-1H-pyrazole-3-carboxylate, ethyl 5-tert-butyl-1-(2,4-dichlorophenyl)-1H-pyrazole-3-carboxylate and similar compounds known from EP-A 0 333 131 and EP-A 0 269 806; for example 1,5-diphenylpyrazole-3-carboxylic acid derivatives, e.g. ethyl 1-(2,4-dichlorophenyl)-5-phenyl-1H-pyrazole-3-carboxylate, methyl 1-(2-chlorophenyl)-5-phenyl-1H-pyrazole-3-carboxylate, and similar compounds known from EP-A 0 268 554; for example triazolecarboxylic acid derivatives, e.g. fenchlorazole, fenchlorazole-ethyl, and similar compounds known from EP-A 0 174 562 and EP-A 0 346 620; for example 2-isoxazoline-3-carboxylic acid derivatives, e.g. ethyl 5-(2,4-dichlorobenzyl)-4,5-dihydro-1,2-oxazole-3-carboxylate, ethyl 5-phenyl-4,5-dihydro-1,2-oxazole-3-carboxylate and similar compounds known from WO 91/08202, or 5,5-diphenyl-4,5-dihydro-1,2-oxazole-3-carboxylic acid, ethyl 5,5-diphenyl-4,5-dihydro-1,2-oxazole-3-carboxylate ("isoxadifen-ethyl"), propyl 5,5-diphenyl-4,5-dihydro-1,2-oxazole-3-carboxylate, ethyl 5-(4-fluorophenyl)-5-phenyl-4,5-dihydro-1,2-oxazole-3-carboxylate known from WO 95/07897.

(2) Derivatives of 8-quinolinol, for example derivatives of (quinolin-8-yloxy)acetic acid, e.g. heptan-2-yl[(5-chloroquinolin-8-yl)oxy]acetate ("cloquintocet-mexyl"), 4-methylpentan-2-yl[(5-chloroquinolin-8-yl)-oxy]acetate,4-(allyloxy)butyl [(5-chloroquinolin-8-yl)oxy]acetate, 1-(allyloxy)propan-2-yl[(5-chloroquinolin-8-yl)oxy]acetate, ethyl [(5-chloroquinolin-8-yl)oxy]acetate, methyl [(5-chloroquinolin-8-yl)oxy]acetate, allyl [(5-chloroquinolin-8-yl)oxy]acetate, 2-{[propylideneamino]oxy}ethyl [(5-chloroquinolin-8-yl)oxy]acetate, 2-oxopropyl [(5-chloroquinolin-8-yl)oxy]acetate, and similar compounds known from EP-A 0 086 750, EP-A 0 094 349, EP-A 0 191 736 or EP-A 0 492 366, as well as [(5-chloroquinolin-8-yl)oxy]acetic acid, its hydrates and salts, e.g. the lithium, sodium, potassium, calcium, magnesium, aluminum, iron, ammonium, quartanary ammonium, sulfonium or phosphonium salts as known from WO 02/34048; for example derivatives of [(5-chloroquinolin-8-yl)oxy]malonic acid, e.g diethyl [(5-chloroquinolin-8-yl)oxy]malonate, diallyl [(5-chloroquinolin-8-yl)oxy]malonate, ethyl methyl [(5-chloroquinolin-8-yl)oxy]malonate, and similar compounds known from EP-A 0 582 198.

(3) Dichloroacetamides, which are often used as pre-emergence safeners (soil active safeners), e.g. "dichlormid" (N,N-diallyl-2,2-dichloroacetamide), "R-29148" (3dichloroacetyl-2,2,5-trimethyl-1,3-oxazolidine) and "R-28725" (3-dichloroacetyl-2,2,-dimethyl-1,3-oxazolidine) both of the company Stauffer, "benoxacor" (4-dichloroacetyl-3,4-dihydro-3-methyl-2H-1,4-benzoxazine), "PPG-1292" (N-allyl-N-[(1,3-dioxolan-2-yl)-methyl]-dichloroacetamide) of PPG Industries, "DKA-24" (N-allyl-N-[(allylaminocarbonyl)methyl]-dichloroacetamide) of Sagro-Chem, "AD-67" or "MON 4660" (3-dichloroacetyl-1-oxa-3-aza-spiro[4,5]decane) of Nitrokemia and Monsanto, "TI-35" (1-dichloroacetyl-azepane) of TRI-Chemical RT, "diclonon" (dicyclonon) or "BAS145138" or "LAB145138" (3-dichloroacetyl-2,5,5-trimethyl-1,3-diazabicyclo[4.3.0] nonane) of BASF, "Furilazol" or "MON 13900" [(RS)-3-dichloroacetyl-5-(2-furyl)-2,2-dimethyloxazolidine], as well as there (R)-isomer.

(4) Acylsulfonamides, for example N-acylsulfonamide of the formula (II)

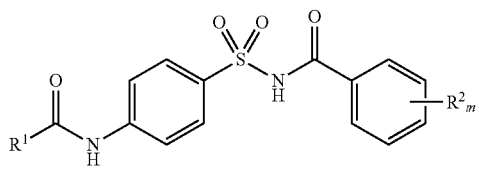

or its salts (known from WO 97/45016), wherein
$R^1$ represents $(C_1-C_6)$alkyl, which is unsubstituted or mono- to trisubstituted by substituents selected from the group consisting of halogen, $(C_1-C_4)$alkoxy, $(C_1-C_6)$haloalkoxy and $(C_1-C_4)$alkylthio;
$R^2$ represents halogen, $(C_1-C_4)$alkyl, $(C_1-C_4)$alkoxy, $CF_3$;
m is 1 or 2;
or for example 4-(benzoylsulfamoyl)benzamides of the formula (III)

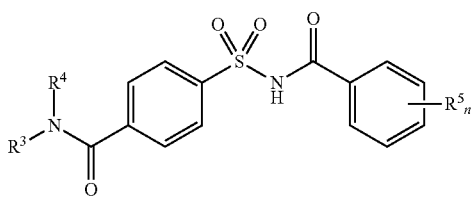

or its salts (known from WO 99/16744), wherein
$R^3$, $R^4$ independently of one another represent hydrogen, $(C_1-C_6)$alkyl, $(C_3-C_6)$alkenyl, $(C_3-C_6)$alkynyl, $(C_3-C_6)$cycloalkyl,
$R^5$ represents halogen, $(C_1-C_4)$alkyl, $(C_1-C_4)$haloalkyl or $(C_1-C_4)$alkoxy
n is 1 or 2,
in particular compounds of formula (III), wherein
$R^3$=cyclopropyl, $R^4$=hydrogen and $R^5_n$=2-OMe, ("cyprosulfamide"),
$R^3$=cyclopropyl, $R^4$=hydrogen and $R^5_n$=5-Cl-2-OMe,
$R^3$=ethyl, $R^4$=hydrogen and $R^5_n$=2-OMe,
$R^3$=isopropyl, $R^4$=hydrogen and $R^5_n$=5-Cl-2-OMe,
$R^3$=isopropyl, $R^4$=hydrogen and $R^5_n$=2-OMe.
or for example benzoylsulfamoylphenylureas of the formula (IV)

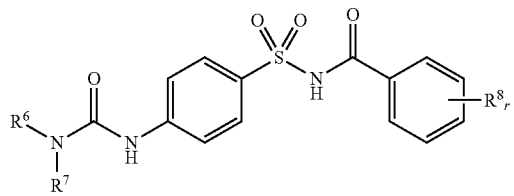

(known from EP-A 0 365 484), wherein
$R^6$, $R^7$ independently of one another represent hydrogen, $(C_1-C_8)$alkyl, $(C_3-C_6)$alkenyl, $(C_3-C_6)$alkynyl,
$R^8$ represents halogen, $(C_1-C_4)$alkyl, $(C_1-C_4)$alkoxy, $CF_3$
r is 1 or 2;

in particular
1-[4-(N-2-methoxybenzoylsulfamoyl)phenyl]-3-methyl urea,
1-[4-(N-2-methoxybenzoylsulfamoyl)phenyl]-3,3-dimethyl urea,
1-[4-(N-4,5-dimethylbenzoylsulfamoyl)phenyl]-3-methyl urea.

(5) Hydroxyaromatic compounds and aromatic-aliphatic carboxylic acid derivatives, e.g. ethyl 3,4,5-triacetoxybenzoate, 4-hydroxy-3,5-dimethoxybenzoic acid, 3,5-dihydroxybenzoic acid, 2,4-dihydroxybenzoic acid, 4-fluoro-2-hydroxybenzoic acid, 2-hydroxycinnamic acid, 2,4-dichlorocinnamic acid (cf. WO 2004/084631, WO 2005/015994, WO 2005/016001).

(6) 1,2-Dihydrochinoxalin-2-ones, e.g. 1-methyl-3-(2-thienyl)-1,2-dihydrochinoxalin-2-one, 1-methyl-3-(2-thienyl)-1,2-dihydrochinoxalin-2-thione, 1-(2-aminoethyl)-3-(2-thienyl)-1,2-dihydrochinoxalin-2-one hydrochlorid, 1-(2-methyl sulfonylaminoethyl)-3-(2-thienyl)-1,2-dihydrochinoxalin-2-one (cf. WO 2005/112630).

(7) Diphenylmethoxyacetic acid derivatives, e.g. methyl (diphenylmethoxy)acetate (CAS-Reg. No. 41858-19-9), ethyl (diphenylmethoxy)acetate or (diphenylmethoxy)acetic acid (cf. WO 98/38856).

(8) Compounds of formula (V)

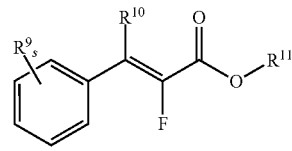

or its salts (known from WO 98/27049), wherein
$R^9$ represents halogen, $(C_1-C_4)$alkyl, $(C_1-C_4)$haloalkyl, $(C_1-C_4)$alkoxy, $(C_1-C_4)$haloalkoxy,
$R^{10}$ represents hydrogen or $(C_1-C_4)$alkyl,
$R^{10}$ represents hydrogen, in each case unsubstituted or mono- to trisubstituted $(C_1-C_8)$alkyl, $(C_2-C_4)$alkenyl, $(C_2-C_4)$alkynyl, or aryl, where the substituents are selected from the group consisting of halogen and $(C_1-C_8)$alkoxy,
s is 0, 1 or 2.

(9) 3-(5-Tetrazolylcarbonyl)-2-chinolones, e.g. 1,2-dihydro-4-hydroxy-1-ethyl-3-(5-tetrazolylcarbonyl)-2-chinolone (CAS-Reg. No. 219479-18-2), 1,2-dihydro-4-hydroxy-1-methyl-3-(5-tetrazolylcarbonyl)-2-chinolone (CAS-Reg. No. 95855-00-8) (cf. WO 99/00020).

(10) Compounds of the formulae (VI-a) and (VI-b)

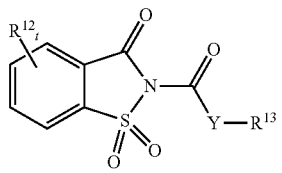

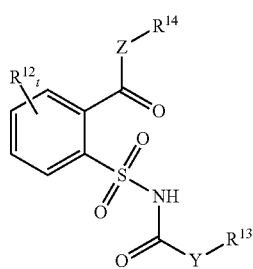

(VI-b)

(known from WO 2007/023719 and WO 2007/023764), wherein $R^{12}$ represents halogen, $(C_1-C_4)$alkyl, methoxy, nitro, cyano, $CF_3$, $OCF_3$, Y, Z independently represent O or S, t is 0, 1, 2, 3 or 4, $R^{13}$ represents $(C_1-C_{16})$alkyl, $(C_2-C_6)$alkenyl, aryl, benzyl, halogenobenzyl, $R^{14}$ represents hydrogen or $(C_1-C_6)$alkyl.

(11) Oxyimino compounds, known as seed treatment agents, e.g. "oxabetrinil" [(Z)-1,3-dioxolan-2-ylmethoxy-imino(phenyl)acetonitril], "fluxofenim" [1-(4-chlorophenyl)-2,2,2-trifluoro-1-ethanone-O-(1,3-dioxolan-2-ylmethyl)-oxime], and "cyometrinil" or "CGA-43089" [(Z)-cyanomethoxy-imino(phenyl)acetonitril], all known as seed treatment safener for sorghum against damage by metolachlor.

(12) Isothiochromanones, e.g. methyl [(3-oxo-1H-2-benzothiopyran-4(3H)-ylidene)methoxy]acetate (CAS-Reg. No. 205121-04-6) and similar compounds known from WO 98/13361.

(13) Compounds from the group consisting of "naphthalic anhydrid" (1,8-naphthalinedicarboxylic acid anhydride), which is known as seed treatment safener for corn (maize) against damage by thiocarbamate herbicides, "fenclorim" (4,6-dichloro-2-phenylpyrimidine), which is known as seed treatment safener in sown rice against damage by pretilachlor, "flurazole" (benzyl-2-chloro-4-trifluoromethyl-1,3-thiazol-5-carboxylate), which is known as seed treatment safener for sorghum against damage by alachlor and metolachlor, "CL 304415" (CAS-Reg. No. 31541-57-8), (4-carboxy-3,4-dihydro-2H-1-benzopyran-4-acetic acid) of American Cyanamid, which is known as safener for corn (maize) against damage by imidazolinones, "MG 191" (CAS-Reg. No. 96420-72-3) (2-dichloromethyl-2-methyl-1,3-dioxolane) of Nitrokemia, known as safener for corn (maize), "MG-838" (CAS-Reg. No. 133993-74-5), (2-propenyl 1-oxa-4-azaspiro[4.5]decane-4-carbodithioate) of Nitrokemia, "Disulfoton" (O,O-diethyl-S-2-ethylthioethyl phosphorodithioate), "dietholate" (O,O-diethyl-O-phenylphosphorothioate), "mephenate" (4-chlorophenyl-methylcarbamate).

(14) Compounds, which besides herbicidal activity als exhibit Safener activity in crops like rice, e.g. "Dimepiperate" or "MY-93" (S-1-methyl-1-phenylethyl-piperidin-1-carbothioate), which is known as safener for rice against damage by molinate, "daimuron" or "SK 23" [1-(1-methyl-1-phenylethyl)-3-p-tolyl-urea], which is known as safener for rice against damage by imazosulfuron, "cumyluron"="JC-940" [3-(2-chlorophenylmethyl)-1-(1-methyl-1-phenyl-ethyl) urea] (cf. JP-A 60-087254), which is known as safener for rice against damage by some herbicides, "methoxyphenon" or "NK 049" (3,3'-dimethyl-4-methoxy-benzophenone), which is known as safener for rice against damage by some herbicides, "CSB" [1-bromo-4-(chloromethylsulfonyl)benzene] of Kumiai (CAS-Reg. No. 54091-06-4), which is known as safener for rice against damage by some herbicides.

(15) Compounds, which are mainly used as herbicides, but which exhibit also safener activity on some crops, e.g. (2,4-dichlorophenoxy)acetic acid (2,4-D), (4-chlorophenoxy)acetic acid, (R,S)-2-(4-chlor-o-tolyloxy)propionic acid (mecoprop), 4-(2,4-dichlorophenoxy)butyric acid (2,4-DB), (4-chloro-o-tolyloxy)acetic acid (MCPA), 4-(4-chloro-o-tolyloxy)butyric acid, 4-(4-chlorophenoxy)butyric acid, 3,6-dichloro-2-methoxybenzoic acid (dicamba), 1-(ethoxycarbonyl)ethyl-3,6-dichloro-2-methoxybenzoate (lactidichlorethyl).

being plant growth regulators which may be mentioned are chlorocholine chloride and ethephon.

Examples of plant nutrients which may be mentioned are customary inorganic or organic fertilizers for supplying plants with macro- and/or micronutrients.

The active ingredients specified herein by their "common name" are known and described, for example, in the Pesticide Manual ("The Pesticide Manual", 14th Ed., British Crop Protection Council 2006) or can be searched in the internet (e.g. http://www.alanwood.net/pesticides).

In a preferred embodiment the present invention relates to the use of a composition comprising A) a compound of the general formula (I) and B) one or more of the following insecticides: Acrinathrin, Alpha-Cypermethrin, Betacyfluthrin, Cyhalothrin, Cypermethrin, Deltamethrin, Lambda-Cyhalothrin, Gamma-Cyhalothrin, Transfluthrin, Cyfluthrin, Bifenthrin, Tefluthrin, Imidacloprid, Acetamiprid, Thiamethoxam, Thiacloprid, Dinotefuran, Clothianidin, Lufenuron, Triflumuron, Novaluron, Flufenoxuron, Buprofezin, Methoxyfenozide, Tebufenozide, Fipronil, Ethiprole, Flubendiamide, Chlorantraniliprole (Rynaxypyr), Cyazypyr, Emamectin, Emamectin benzoate, Abamectin, Milbemectin, Tebufenpyrad, Fenpyroximat, Diafenthiuron, Spinosad, Flonicamid, Chlorfenapyr, Metaflumizone, Indoxacarb, Chlorpyrifos, Spirodiclofen, Spiromesifen, Spirotetramat, Pyridalyl, Spinetoram, Acephate, Triazophos, Profenofos, Fenamiphos, 4-{[(6-Chlorpyrid-3-yl)methyl](2,2-difluorethyl)amino}furan-2(5H)-on, Cadusaphos, Carbaryl, Carbofuran, Ethoprophos, Thiodicarb, Aldicarb, Metamidophos, Methiocarb, Sulfoxaflor, Methomyl, Imicyafos, Fluensulfone, 11-(4-Chlor-2,6-dimethylphenyl)-12-hydroxy-1,4-dioxa-9-azadispiro[4.2.4.2]tetradec-11-en-10-on, 2-{6-[2-(5-Fluorpyridin-3-yl)-1,3-thiazol-5-yl]pyridin-2-yl}pyrimidin.

In a preferred embodiment the present invention relates to the use of a composition comprising A) a compound of the general formula (I) and B) one or more of the following fungicides: Bitertanol, Bixafen, Carpropamid, Fenamidone, Fluopicolide, Fluopyram, Fluoxastrobin, Fluquinconazole, Isotianil, Metaminostrobin, Pencycuron, Penflufen, Prochloraz, Propamocarb, Propineb, Prothioconazole, Spiroxamine, Tebuconazole, Triadimenol, Triazoxide, Trifloxystrobin-Ametoctradin, Azoxystrobin, Benthiavalicarb, Boscalid, Carbendazim, Carboxin, Chlorothalonil, Cymoxanil, Cyproconazole, Cyprodinil, Cyzofamid, Difenoconazole, Dimoxystrobin, Epoxiconazole, Fenpropidin, Ferimzone, Fluazinam, Fludioxonil, Flutolanil, Flutriafol, Fluxapyroxad, Gentamycin, Hymexazol, Imazalil, Ipconazole, Isoprothiolane, Isopyrazam, Kasugamycin, Mancozeb, Mandipropamid, Maneb, Mefenoxam, Metalaxyl, Metconazole, Metrafenone, Orysastrobin, Penthiopyrad, Picoxystrobin, Probenazole, Propiconazole, Proquinazid, Pyraclostrobin, Pyrimethanil, Pyroquilon, Quinoxyfen, Sedaxane, Tetraconazole, Thiophanate-methyl, Thiram, Tolclofos-methyl, Tricyclazole, Triticonazole, Validamycin.

Agricultural Pests

The agricultural pests and pathogens to be controlled when a compound of formula (I) or compositions comprising a compound of the formula (I) are used or employed according to the invention are given hereafter:

pests from the phylum Arthropoda, especially from the class Arachnida, for example, *Acarus* spp., *Aceria sheldoni*, *Aculops* spp., *Aculus* spp., *Amblyomma* spp., *Amphitetranychus viennensis*, *Argas* spp., *Boophilus* spp., *Brevipalpus* spp., *Bryobia graminum*, *Bryobia praetiosa*, *Centruroides* spp., *Chorioptes* spp., *Dermanyssus gallinae*, *Dermatophagoides pteronyssinus*, *Dermatophagoides farinae*, *Dermacentor* spp., *Eotetranychus* spp., *Epitrimerus pyri*, *Eutetranychus* spp., *Eriophyes* spp., *Glycyphagus domesticus*, *Halotydeus destructor*, *Hemitarsonemus* spp., *Hyalomma* spp., *Ixodes* spp., *Latrodectus* spp., *Loxosceles* spp., *Metatetranychus* spp., *Neutrombicula autumnalis*, *Nuphersa* spp., *Oligonychus* spp., *Ornithodorus* spp., *Ornithonyssus* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Steneotarsonemus* spp., *Steneotarsonemus spinki*, *Tarsonemus* spp., *Tetranychus* spp., *Trombicula alfreddugesi*, *Vaejovis* spp., *Vasates lycopersici*;

from the class Chilopoda, for example, *Geophilus* spp., *Scutigera* spp.;

from the order or the class Collembola, for example, *Onychiurus armatus*;

from the class Diplopoda, for example, *Blaniulus guttulatus*;

from the class Insecta, e.g. from the order Blattodea, for example, *Blattella asahinai*, *Blattella germanica*, *Blatta orientalis*, *Leucophaea maderae*, *Panchlora* spp., *Parcoblatta* spp., *Periplaneta* spp., *Supella longipalpa*;

from the order Coleoptera, for example, *Acalymma vittatum*, *Acanthoscelides obtectus*, *Adoretus* spp., *Agelastica alni*, *Agriotes* spp., *Alphitobius diaperinus*, *Amphimallon solstitialis*, *Anobium punctatum*, *Anoplophora* spp., *Anthonomus* spp., *Anthrenus* spp., *Apion* spp., *Apogonia* spp., *Atomaria* spp., *Attagenus* spp., *Bruchidius obtectus*, *Bruchus* spp., *Cassida* spp., *Cerotoma trifurcata*, *Ceutorrhynchus* spp., *Chaetocnema* spp., *Cleonus mendicus*, *Conoderus* spp., *Cosmopolites* spp., *Costelytra zealandica*, *Ctenicera* spp., *Curculio* spp., *Cryptolestes ferrugineus*, *Cryptorhynchus lapathi*, *Cylindrocopturus* spp., *Dermestes* spp., *Diabrotica* spp., *Dichocrocis* spp., *Dicladispa armigera*, *Diloboderus* spp., *Epilachna* spp., *Epitrix* spp., *Faustinus* spp., *Gibbium psylloides*, *Gnathocerus cornutus*, *Hellula undalis*, *Heteronychus arator*, *Heteronyx* spp., *Hylamorpha elegans*, *Hylotrupes bajulus*, *Hypera postica*, *Hypomeces squamosus*, *Hypothenemus* spp., *Lachnosterna consanguinea*, *Lasioderma serricorne*, *Latheticus oryzae*, *Lathridius* spp., *Lema* spp., *Leptinotarsa decemlineata*, *Leucoptera* spp., *Lissorhoptrus oryzophilus*, *Lixus* spp., *Luperodes* spp., *Lyctus* spp., *Megascelis* spp., *Melanotus* spp., *Meligethes aeneus*, *Melolontha* spp., *Migdolus* spp., *Monochamus* spp., *Naupactus xanthographus*, *Necrobia* spp., *Niptus hololeucus*, *Oryctes rhinoceros*, *Oryzaephilus surinamensis*, *Oryzaphagus oryzae*, *Otiorrhynchus* spp., *Oxycetonia jucunda*, *Phaedon cochleariae*, *Phyllophaga* spp., *Phyllophaga helleri*, *Phyllotreta* spp., *Popillia japonica*, *Premnotrypes* spp., *Prostephanus truncatus*, *Psylliodes* spp., *Ptinus* spp., *Rhizobius ventralis*, *Rhizopertha dominica*, *Sitophilus* spp., *Sitophilus oryzae*, *Sphenophorus* spp., *Stegobium paniceum*, *Sternechus* spp., *Symphyletes* spp., *Tanymecus* spp., *Tenebrio molitor*, *Tenebrioides mauretanicus*, *Tribolium* spp., *Trogoderma* spp., *Tychius* spp., *Xylotrechus* spp., *Zabrus* spp.;

from the order Diptera, for example, *Aedes* spp., *Agromyza* spp., *Anastrepha* spp., *Anopheles* spp., *Asphondylia* spp., *Bactrocera* spp., *Bibio hortulanus*, *Calliphora erythrocephala*, *Calliphora vicina*, *Ceratitis capitata*, *Chironomus* spp., *Chrysomyia* spp., *Chrysops* spp., *Chrysozona pluvialis*, *Cochliomyia* spp., *Contarinia* spp., *Cordylobia anthropophaga*, *Cricotopus sylvestris*, *Culex* spp., *Culicoides* spp., *Culiseta* spp., *Cuterebra* spp., *Dacus oleae*, *Dasyneura* spp., *Delia* spp., *Dermatobia hominis*, *Drosophila* spp., *Echinocnemus* spp., *Fannia* spp., *Gasterophilus* spp., *Glossina* spp., *Haematopota* spp., *Hydrellia* spp., *Hydrellia griseola*, *Hylemya* spp., *Hippobosca* spp., *Hypoderma* spp., *Liriomyza* spp., *Lucilia* spp., *Lutzomyia* spp., *Mansonia* spp., *Musca* spp., *Oestrus* spp., *Oscinella frit*, *Paratanytarsus* spp., *Paralauterborniella subcincta*, *Pegomyia* spp., *Phlebotomus* spp., *Phorbia* spp., *Phormia* spp., *Piophila casei*, *Prodiplosis* spp., *Psila rosae*, *Rhagoletis* spp., *Sarcophaga* spp., *Simulium* spp., *Stomoxys* spp., *Tabanus* spp., *Tetanops* spp., *Tipula* spp.;

from the order Heteroptera, for example, *Anasa tristis*, *Antestiopsis* spp., *Boisea* spp., *Blissus* spp., *Calocoris* spp., *Campylomma livida*, *Cavelerius* spp., *Cimex* spp., *Collaria* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptocorisa varicornis*, *Leptoglossus phyllopus*, *Lygus* spp., *Macropes excavatus*, *Miridae*, *Monalonion atratum*, *Nezara* spp., *Oebalus* spp., *Pentomidae*, *Piesma quadrata*, *Piezodorus* spp., *Psallus* spp., *Pseudacysta persea*, *Rhodnius* spp., *Sahlbergella singularis*, *Scaptocoris castanea*, *Scotinophora* spp., *Stephanitis nashi*, *Tibraca* spp., *Triatoma* spp.;

from the order Homoptera, for example, *Acizzia acaciaebaileyanae*, *Acizzia dodonaeae*, *Acizzia uncatoides*, *Acrida turrita*, *Acyrthosipon* spp., *Acrogonia* spp., *Aeneolamia* spp., *Agonoscena* spp., *Aleyrodes proletella*, *Aleurolobus barodensis*, *Aleurothrixus floccosus*, *Allocaridara malayensis*, *Amrasca* spp., *Anuraphis cardui*, *Aonidiella* spp., *Aphanostigma pini*, *Aphis* spp., *Arboridia apicalis*, *Arytainilla* spp., *Aspidiella* spp., *Aspidiotus* spp., *Atanus* spp., *Aulacorthum solani*, *Bemisia tabaci*, *Blastopsylla occidentalis*, *Boreioglycaspis melaleucae*, *Brachycaudus helichrysi*, *Brachycolus* spp., *Brevicoryne brassicae*, *Cacopsylla* spp., *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chondracris rosea*, *Chromaphis juglandicola*, *Chrysomphalus ficus*, *Cicadulina mbila*, *Coccomytilus halli*, *Coccus* spp., *Cryptomyzus ribis*, *Cryptoneossa* spp., *Ctenarytaina* spp., *Dalbulus* spp., *Dialeurodes citri*, *Diaphorina citri*, *Diaspis* spp., *Drosicha* spp., *Dysaphis* spp., *Dysmicoccus* spp., *Empoasca* spp., *Eriosoma* spp., *Erythroneura* spp., *Eucalyptolyma* spp., *Euphyllura* spp., *Euscelis bilobatus*, *Ferrisia* spp., *Geococcus coffeae*, *Glycaspis* spp., *Heteropsylla cubana*, *Heteropsylla spinulosa*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Macrosteles facifrons*, *Mahanarva* spp., *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nettigoniclla spectra*, *Nilaparvata lugens*, *Oncometopia* spp., *Orthezia praelonga*, *Oxya chinensis*, *Pachypsylla* spp., *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon*

*humuli*, *Phylloxera* spp., *Pinnaspis aspidistrae*, *Planococcus* spp., *Prosopidopsylla flava*, *Protopulvinaria pyriformis*, *Pseudaulacaspis pentagona*, *Pseudococcus* spp., *Psyllopsis* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoideus titanus*, *Schizaphis graminum*, *Selenaspidus articulatus*, *Sogata* spp., *Sogatella furcifera*, *Sogatodes* spp., *Stictocephala festina*, *Siphoninus phillyreae*, *Tenalaphara malayensis*, *Tetragonocephela* spp., *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*, *Zygina* spp.;

from the order Hymenoptera, for example, *Acromyrmex* spp., *Athalia* spp., *Atta* spp., *Diprion* spp., *Hoplocampa* spp., *Lasius* spp., *Monomorium pharaonis*, *Sirex* spp., *Solenopsis invicta*, *Tapinoma* spp., *Urocerus* spp., *Vespa* spp., *Xeris* spp.;

from the order Isopoda, for example, *Armadillidium vulgare*, *Oniscus asellus*, *Porcellio scaber*;

from the order Isoptera, for example, *Coptotermes* spp., *Cornitermes cumulans*, *Cryptotermes* spp., *Incisitermes* spp., *Microtermes obesi*, *Odontotermes* spp., *Reticulitermes* spp.;

from the order Lepidoptera, for example, *Achroia grisella*, *Acronicta major*, *Adoxophyes* spp., *Aedia leucomelas*, *Agrotis* spp., *Alabama* spp., *Amyelois transitella*, *Anarsia* spp., *Anticarsia* spp., *Argyroploce* spp., *Barathra brassicae*, *Borbo cinnara*, *Bucculatrix thurberiella*, *Bupalus piniarius*, *Busseola* spp., *Cacoecia* spp., *Caloptilia theivora*, *Capua reticulana*, *Carpocapsa pomonella*, *Carposina niponensis*, *Chematobia brumata*, *Chilo* spp., *Choristoneura* spp., *Clysia ambiguella*, *Cnaphalocerus* spp., *Cnaphalocrocis medinalis*, *Cnephasia* spp., *Conopomorpha* spp., *Conotrachelus* spp., *Copitarsia* spp., *Cydia* spp., *Dalaca noctuides*, *Diaphania* spp., *Diatraea saccharalis*, *Earias* spp., *Ecdytolopha aurantium*, *Elasmopalpus lignosellus*, *Eldana saccharina*, *Ephestia* spp., *Epinotia* spp., *Epiphyas postvittana*, *Etiella* spp., *Eulia* spp., *Eupoecilia ambiguella*, *Euproctis* spp., *Euxoa* spp., *Feltia* spp., *Galleria mellonella*, *Gracillaria* spp., *Grapholitha* spp., *Hedylepta* spp., *Helicoverpa* spp., *Heliothis* spp., *Hofmannophila pseudospretella*, *Homoeosoma* spp., *Homona* spp., *Hyponomeuta padella*, *Kakivoria flavofasciata*, *Laphygma* spp., *Laspeyresia molesta*, *Leucinodes orbonalis*, *Leucoptera* spp., *Lithocolletis* spp., *Lithophane antennata*, *Lobesia* spp., *Loxagrotis albicosta*, *Lymantria* spp., *Lyonetia* spp., *Malacosoma neustria*, *Maruca testulalis*, *Mamstra brassicae*, *Melanitis leda*, *Mocis* spp., *Monopis obviella*, *Mythimna separata*, *Nemapogon cloacellus*, *Nymphula* spp., *Oiketicus* spp., *Oria* spp., *Orthaga* spp., *Ostrinia* spp., *Oulema oryzae*, *Panolis flammea*, *Parnara* spp., *Pectinophora* spp., *Perileucoptera* spp., *Phthorimaea* spp., *Phyllocnistis citrella*, *Phyllonorycter* spp., *Pieris* spp., *Platynota stultana*, *Plodia interpunctella*, *Plusia* spp., *Plutella xylostella*, *Prays* spp., *Prodenia* spp., *Protoparce* spp., *Pseudaletia* spp., *Pseudaletia unipuncta*, *Pseudoplusia includens*, *Pyrausta nubilalis*, *Rachiplusia nu*, *Schoenobius* spp., *Scirpophaga* spp., *Scirpophaga innotata*, *Scotia segetum*, *Sesamia* spp., *Sesamia inferens*, *Sparganothis* spp., *Spodoptera* spp., *Spodoptera praefica*, *Stathmopoda* spp., *Stomopteryx subsecivella*, *Synanthedon* spp., *Tecia solanivora*, *Thermesia gemmatalis*, *Tinea cloacella*, *Tinea pellionella*, *Tineola bisselliella*, *Tortrix* spp., *Trichophaga tapetzella*, *Trichoplusia* spp., *Tryporyza incertulas*, *Tuta absoluta*, *Virachola* spp.;

from the order Orthoptera or Saltatoria, for example, *Acheta domesticus*, *Dichroplus* spp., *Gryllotalpa* spp., *Hieroglyphus* spp., *Locusta* spp., *Melanoplus* spp., *Schistocerca gregaria*;

from the order Phthiraptera, for example, *Damalinia* spp., *Haematopinus* spp., *Linognathus* spp., *Pediculus* spp., *Ptirus pubis*, *Trichodectes* spp.;

from the order Psocoptera for example *Lepinatus* spp., *Liposcelis* spp.;

from the order Siphonaptera, for example, *Ceratophyllus* spp., *Ctenocephalides* spp., *Pulex irritans*, *Tunga penetrans*, *Xenopsylla cheopsis*;

from the order Thysanoptera, for example, *Anaphothrips obscurus*, *Baliothrips biformis*, *Drepanothrips reuteri*, *Enneothrips flavens*, *Frankliniella* spp., *Heliothrips* spp., *Hercinothrips femoralis*, *Rhipiphorothrips cruentatus*, *Scirtothrips* spp., *Taeniothrips cardamomi*, *Thrips* spp.;

from the order Zygentoma (=Thysanura), for example, *Ctenolepisma* spp., *Lepisma saccharina*, *Lepismodes inquilinus*, *Thermobia domestica*;

from the class Symphyla, for example, *Scutigerella* spp.;

pests from the phylum Mollusca, especially from the class Bivalvia, for example, *Dreissena* spp., and from the class Gastropoda, for example, *Anion* spp., *Biomphalaria* spp., *Bulinus* spp., *Deroceras* spp., *Galba* spp., *Lymnaea* spp., *Oncomelania* spp., *Pomacea* spp., *Succinea* spp.;

animal pests from the phylums Plathelminthes and Nematoda, for example, *Ancylostoma duodenale*, *Ancylostoma ceylanicum*, *Acylostoma braziliensis*, *Ancylostoma* spp., *Ascaris* spp., *Brugia malayi*, *Brugia timori*, *Bunostomum* spp., *Chabertia* spp., *Clonorchis* spp., *Cooperia* spp., *Dicrocoelium* spp., *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancroftiIt* is furthermore possible to control organisms from the subphylum Protozoa, especially from the order Coccidia, such as *Eimeria* spp.

Nematodes

The active compounds of the formula (I) are particularly useful in controlling plant-parasitic nematodes in nematode-resistant plants wherein the nematodes are of the following species:

*Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus* spp., *Trichodorus* spp., *Tylenchulus* spp, *Xiphinema* spp., *Helicotylenchus* spp., *Tylenchorhynchus* spp., *Scutellonema* spp., *Paratrichodorus* spp., *Meloinema* spp., *Paraphelenchus* spp., *Aglenchus* spp., *Belonolaimus* spp., *Nacobbus* spp, *Rotylenchulus* spp., *Rotylenchus* spp., *Neotylenchus* spp., *Paraphelenchus* spp., *Dolichodorus* spp., *Hoplolaimus* spp., *Punctodera* spp., *Criconemella* spp., *Quinisulcius* spp., *Hemicycliophora* spp., *Anguina* spp., *Subanguina* spp., *Hemicriconemoides* spp., *Psilenchus* spp., *Pseudohalenchus* spp., *Criconemoides* spp., *Cacopaurus* spp

*Aglenchus agricola*, *Anguina tritici*, *Aphelenchoides arachidis*, *Aphelenchoides fragariae*, *Belonolaimus gracilis*, *Belonolaimus longicaudatus*, *Belonolaimus nortoni*, *Cacopaurus pestis*, *Criconemella curvata*, *Criconemella onoensis*, *Criconemella ornata*, *Criconemella rusium*, *Criconemella xenoplax* (=*Mesocriconema xenoplax*) and *Criconemella* spp. in general, *Criconemoides ferniae*, *Criconemoides onoense*, *Criconemoides ornatum* and

*Criconemoides* spp. in general, *Ditylenchus destructor, Ditylenchus dipsaci, Ditylenchus myceliophagus* and *Ditylenchus* spp. in general, *Dolichodorus heterocephalus, Globodera pallida* (=*Heterodera pallida*), *Globodera rostochiensis, Globodera solanacearum, Globodera tabacum, Globodera virginiae, Helicotylenchus digonicus, Helicotylenchus dihystera, Helicotylenchus erythrine, Helicotylenchus multicinctus, Helicotylenchus nannus, Helicotylenchus pseudorobustus* and *Helicotylenchus* spp. in general, *Hemicriconemoides, Hemicycliophora arenaria, Hemicycliophora nudata, Hemicycliophora parvana, Heterodera avenae, Heterodera cruciferae, Heterodera glycines, Heterodera oryzae, Heterodera schachtii, Heterodera zeae* and *Heterodera* spp. in general, *Hoplolaimus aegyptii, Hoplolaimus californicus, Hoplolaimus columbus, Hoplolaimus galeatus, Hoplolaimus indicus, Hoplolaimus magnistylus, Hoplolaimus pararobustus, Longidorus africanus, Longidorus breviannulatus, Longidorus elongatus, Longidorus laevicapitatus, Longidorus vineacola* and *Longidorus* spp. in general, *Meloidogyne acronea, Meloidogyne africana, Meloidogyne arenaria, Meloidogyne arenaria thamesi, Meloidogyne artiella, Meloidogyne chitwoodi, Meloidogyne coffeicola, Meloidogyne ethiopica, Meloidogyne exigua, Meloidogyne graminicola, Meloidogyne graminis, Meloidogyne hapla, Meloidogyne incognita, Meloidogyne incognita acrita, Meloidogyne javanica, Meloidogyne kikuyensis, Meloidogyne naasi, Meloidogyne paranaensis, Meloidogyne thamesi* and *Meloidogyne* spp. in general, *Meloinema* spp., *Nacobbus aberrans, Neotylenchus vigissi, Paraphelenchus pseudoparietinus, Paratrichodorus allius, Paratrichodorus lobatus, Paratrichodorus minor, Paratrichodorus nanus, Paratrichodorus porosus, Paratrichodorus teres* and *Paratrichodorus* spp. in general, *Paratylenchus hamatus, Paratylenchus minutus, Paratylenchus projectus* and *Paratylenchus* spp. in general, *Pratylenchus agilis, Pratylenchus alleni, Pratylenchus andinus, Pratylenchus brachyurus, Pratylenchus cerealis, Pratylenchus coffeae, Pratylenchus crenatus, Pratylenchus delattrei, Pratylenchus giibbicaudatus, Pratylenchus goodeyi, Pratylenchus hamatus, Pratylenchus hexincisus, Pratylenchus loosi, Pratylenchus neglectus, Pratylenchus penetrans, Pratylenchus pratensis, Pratylenchus scribneri, Pratylenchus teres, Pratylenchus thornei, Pratylenchus vulnus, Pratylenchus zeae* and *Pratylenchus* spp. in general, *Pseudohalenchus minutus, Psilenchus magnidens, Psilenchus tumidus, Punctodera chalcoensis, Quinisulcius acutus, Radopholus citrophilus, Radopholus similis, Rotylenchulus borealis, Rotylenchulus parvus, Rotylenchulus reniformis* and *Rotylenchulus* spp. in general, *Rotylenchus laurentinus, Rotylenchus macrodoratus, Rotylenchus robustus, Rotylenchus uniformis* and *Rotylenchus* spp. in general, *Scutellonema brachyurum, Scutellonema bradys, Scutellonema clathricaudatum* and *Scutellonema* spp. in general, *Subanguina radiciola, Tetylenchus nicotianae, Trichodorus cylindricus, Trichodorus minor, Trichodorus primitivus, Trichodorus proximus, Trichodorus similis, Trichodorus sparsus* and *Trichodorus* spp. in general, *Tylenchorhynchus agri, Tylenchorhynchus brassicae, Tylenchorhynchus clarus, Tylenchorhynchus claytoni, Tylenchorhynchus digitatus, Tylenchorhynchus ebriensis, Tylenchorhynchus maximus, Tylenchorhynchus nudus, Tylenchorhynchus vulgaris* and *Tylenchorhynchus* spp. in general, *Tylenchulus semipenetrans, Xiphinema americanum, Xiphinema brevicolle, Xiphinema dimorphicaudatum, Xiphinema index* and *Xiphinema* spp The methods according to the present invention have been found to provide a greater degree of plant vigor and yield in insect and nematode infested environments than would be expected from application of a biological or chemical control agent or the presence of an insect or nematode control gene alone. At least some of the insect or nematode control agents within the scope of the present invention have been shown to provide increased root mass even in the absence of insect pressure which increased root mass leads to improved establishment of the beneficial bacteria within the rhizosphere which, in turn, reduces overall losses in crop vigor and yields caused by insects. Along with the physical combination of these components while treating plants and plant material, in one preferred embodiment of this invention, the compositions of the present invention have been formulated to provide a stable environment for living biological control agents such as spore-forming, root-colonizing bacteria. Various additives may be added to each inventive composition depending on the desired properties for a final formulation which has the necessary physical and chemical stability to produce a commercially viable product.

The active compound combinations according to the invention can be present in commercial formulations and in the use forms prepared from these formulations as a mixture with other active compounds, such as insecticides, attractants, sterilants, bactericides, acaricides, nematicides, fungicides, growth regulators or herbicides. A mixture with fertilizers is also possible.

The treatment according to the invention of the plants and plant parts with the active compound combinations or compositions is carried out directly or by action on their surroundings, habitat or storage space using customary treatment methods, for example by dipping, spraying, atomizing, irrigating, evaporating, dusting, fogging, broadcasting, foaming, painting, spreading-on, watering (drenching), drip irrigating and, in the case of propagation material, in particular in the case of seeds, furthermore as a powder for dry seed treatment, a solution for seed treatment, a water-soluble powder for slurry treatment, by incrusting, by coating with one or more coats, etc. Preference is given to application by dipping, spraying, atomizing, irrigating, evaporating, dusting, fogging, broadcasting, foaming, painting, spreading-on, watering (drenching) and drip irrigating.

In the case of seed treatment, the treatment can be carried out by applying the compound of formula (I), or a combination of the compound of formula (I) with insecticides, fungicides, as a solution, a powder (for dry seed treatment), a water-soluble powder (for slurry seed treatment), or by incrusting, by coating with one or more layers containing the compound of formula (I).

Transgenic Plants

According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods or combinations of these methods, including the transgenic plants and including plant cultivars which can or cannot be protected by plant variety protection rights. By plant parts is meant all above ground and below ground parts and organs of plants such as shoot, leaf, blossom and root, whereby for example leaves, needles, stems, branches, trunks, flowers, blossoms, fruiting bodies, fruits and seed as well as roots, tubers, corms and rhizomes are listed. Crops and vegetative and generative propagating material, for example cuttings, corms, rhizomes, runners and seeds also belong to plant parts. Plant parts also include harvested material and vegetative and generative propagation material, for example seedlings, tubers, rhizomes, cuttings and seeds. Preference is given to the treatment of the plants and the above-ground and below-ground parts and organs of the plants, such as shoot, leaf, flower and root, examples which may be mentioned being leaves, needles, stems, trunks, flowers, and fruits.

Among the plants that can be protected by the method according to the invention, mention may be made of major field crops like corn, soybean, cotton, Brassica oilseeds such as Brassica napus (e.g. canola), Brassica rapa, B. juncea (e.g. mustard) and Brassica carinata, rice, wheat, sugarbeet, sugarcane, sorghum, oats, rye, barley, millet, triticale, flax, vine and various fruits and vegetables of various botanical taxa such as Rosaceae sp. (for instance pip fruit such as apples and pears, but also stone fruit such as apricots, cherries, almonds and peaches, berry fruits such as strawberries), Ribesioidae sp., Juglandaceae sp., Betulaceae sp., Anacardiaceae sp., Fagaceae sp., Moraceae sp., Oleaceae sp., Actimidaceae sp., Lauraceae sp., Musaceae sp. (for instance banana trees and plantings), Rubiaceae sp. (for instance coffee), Theaceae sp., Sterculiceae sp., Rutaceae sp. (for instance lemons, oranges and grapefruit); Solanaceae sp. (for instance tomatoes, potatoes, peppers, eggplant), Liliaceae sp., Compositiae sp. (for instance lettuce, artichoke and chicory—including root chicory, endive or common chicory), Umbelliferae sp. (for instance carrot, parsley, celery and celeriac), Cucurbitaceae sp. (for instance cucumber—including pickling cucumber, squash, watermelon, gourds and melons), Alliaceae sp. (for instance onions and leek), Cruciferae sp. (for instance white cabbage, red cabbage, broccoli, cauliflower, brussel sprouts, pak choi, kohlrabi, radish, horseradish, cress, Chinese cabbage), Leguminosae sp. (for instance peanuts, peas and beans beans—such as climbing beans and broad beans), Chenopodiaceae sp. (for instance mangold, spinach beet, spinach, beetroots), Malvaceae (for instance okra), Asparagaceae (for instance asparagus); horticultural and forest crops; ornamental plants; as well as genetically modified homologues of these crops.

In particular, a compound of the formula (I) or a composition comprising a compound of the formula (I) and a further agrochemical active ingredient can be used according to the invention for controlling animal pests, such as insects and/or unwanted acarids and/or nematodes in transgenic corn, soybean, cotton, rice, oilseed rape, sugar cane, sugar beet, potatoes, vegetables, in particular tomatoes and curcurbits, tobacco, coffee, and fruits.

The method of treatment according to the invention can be used in the treatment of genetically modified organisms (GMOs), e.g. plants or seeds. Genetically modified plants (or transgenic plants) are plants of which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology, RNA interference—RNAi—technology or microRNA—miRNA—technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound or active compound combinations according to the invention may also have a strengthening effect in plants. Accordingly, they are also suitable for mobilizing the defense system of the plant against attack by unwanted microorganisms. This may, if appropriate, be one of the reasons of the enhanced activity of the combinations according to the invention, for example against insects or nematodes. Plant-strengthening (resistance-inducing) substances are to be understood as meaning, in the present context, those substances or combinations of substances which are capable of stimulating the defense system of plants in such a way that, when subsequently inoculated with unwanted microorganisms, the treated plants display a substantial degree of resistance to these microorganisms. In the present case, unwanted microorganisms are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Examples of nematode or insect resistant plants are described in the following patent applications: U.S. Ser. No. 11/765,491, U.S. Ser. No. 11/765,494, U.S. Ser. No. 10/926,819, U.S. Ser. No. 10/782,020, U.S. Ser. No. 12/032,479, U.S. Ser. No. 10/783,417, U.S. Ser. No. 10/782,096, U.S. Ser. No. 11/657,964, U.S. Ser. No. 12/192,904, U.S. Ser. No. 11/396,808, U.S. Ser. No. 12/166,253, U.S. Ser. No. 12/166,239, U.S. Ser. No. 12/166,124, U.S. Ser. No. 12/166,209, U.S. Ser. No. 11/762,886, U.S. Ser. No. 12/364,335, U.S. Ser. No. 11/763,947, U.S. Ser. No. 12/252,453, U.S. Ser. No. 12/209,354, U.S. Ser. No. 12/491,396 U.S. Ser. No. 12/497,221, U.S. Ser. No. 12/644,632, U.S. Ser. No. 12/646,004, U.S. Ser. No. 12/701,058, U.S. Ser. No. 12/718,059, U.S. Ser. No. 12/721,595, U.S. Ser. No. 12/638,591, U.S. Ser. No. 12/249,016, U.S. Ser. No. 12/828,594, WO2009/027539A2, WO2009/027313A2, WO2008/152008A2, WO2008/110522A1, WO2008/095972A1, WO2008/095970A1, WO2008/095969A1, WO2008/095919A1, WO2008/095916A1, WO2008/095911A2, WO2008/095910A1, WO2008/095889A1, WO2008/095886A1, WO2008/077892A1, WO2008/071726A2, WO2006/020821A2, WO2005/082932A2, WO2009/048847A1, WO2007/095469A2, WO2005/012340A1, WO2007/104570A2.

Genes described as nematode control genes are listed in Table I. The nucleotide and amino acid sequence information of these nematode control genes are represented by the SEQ ID NOs listed in columns 4 and 5 of Table 1 with respect to the United States patent application Serial No. listed in column 2 of Table I.

TABLE I

| GENE NAME | U.S. APPLICATION SERIAL NO. | FILING DATE | NUCLEOTIDE SEQ ID NO | AMINO ACID SEQ ID NO |
|---|---|---|---|---|
| axmi205 | 12/828,594 | Jul. 1, 2010 | 1 | 2, 3, 4, 5, 6, 7, 8 |
| optaxmi205v01.03 | 12/828,594 | Jul. 1, 2010 | 10 | 2 |
| optaxmi205v01.02 | 12/828,594 | Jul. 1, 2010 | 9 | 2 |
| optaxmi205v01.04 | 12/828,594 | Jul. 1, 2010 | 11 | 2 |
| optaxmiR1(evo 21) | 12/701,058 | Feb. 5, 2010 | 12 | 13 |
| optaxmiR1(evo 22) | 12/701,058 | Feb. 5, 2010 | 14 | 15 |
| optaxmiR1(evo 23) | 12/701,058 | Feb. 5, 2010 | 16 | 17 |
| optaxmiR1(evo 26) | 12/701,058 | Feb. 5, 2010 | 18 | 19 |
| optaxmi115v01 | 12/497,221 | Jul. 2, 2009 | 15 | 6 |
| optaxmi115v02 | 12/497,221 | Jul. 2, 2009 | 16 | 6 |
| axmi115v02 | 61/471,848 | Apr. 5, 2011 | any of 1-14 | any of 15-31 |
| axmi100 | 12/491,396 | Jun. 25, 2009 | 36, 282 | 96 |
| axmi076 | 12/252,453 | Oct. 16, 2008 | 4, 6, 11 | 5 |
| axmi005 | 12/497,221 | Jul. 2, 2009 | 1, 7 | 4, 9 |
| optcry1Ac | 12/249,016 | Oct. 10, 2008 | 1, 2, 3, 4, 5 | 6 |
| axmi031 | 11/762,886 | Jun. 14, 2007 | 20 | 21 |
| axn2 | 12/638,591 | Dec. 15, 2009 | 7, 10 | 8 |

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Examples of plants with the above-mentioned traits are non-exhaustively listed in Table A.

TABLE A

Non-exclusive list of transgenic plants and events for the design of experiments with the compound of formula (I) related to the invention (source: (AGBIOS, P.O. Box 475, 106 St. John St. Merrickville, Ontario K0G1N0, CANADA) accessible under: http://www.agbios.com/dbase.php.

| | Event | Company | Description | Crop | Patent Ref |
|---|---|---|---|---|---|
| A-1 | ASR-368 | Scotts Seeds | Glyphosate tolerance derived by inserting a modified 5-enolpyruvylshikimate-3-phosphate synthase (EPSPS) encoding gene from *Agrobacterium tumefaciens*, parent line B99061 | *Agrostis stolonifera* Creeping Bentgrass | US 2006-162007 |
| A-2 | GM RZ13 | Syngenta International AG | Beet Necrotic Yellow Vein Virus (BNYVV) resistance | *Beta vulgaris* (sugar beet) | WO2010076212 |
| A-3 | GTSB77 | Novartis Seeds; Monsanto Company | Glyphosate herbicide tolerant sugar beet produced by inserting a gene encoding the enzyme 5-enolypyruvylshikimate-3-phosphate synthase (EPSPS) from the CP4 strain of *Agrobacterium tumefaciens*. | *Beta vulgaris* (sugar beet) | |
| A-4 | H7-1 | Monsanto Company | Glyphosate herbicide tolerant sugar beet produced by inserting a gene encoding the enzyme 5-enolypyruvylshikimate-3-phosphate synthase (EPSPS) from the CP4 strain of *Agrobacterium tumefaciens* | *Beta vulgaris* (sugar beet) | WO 2004-074492 |

TABLE A-continued

Non-exclusive list of transgenic plants and events for the design of experiments with the compound of formula (I) related to the invention (source: (AGBIOS, P.O. Box 475, 106 St. John St. Merrickville, Ontario K0G1N0, CANADA) accessible under: http://www.agbios.com/dbase.php.

| | Event | Company | Description | Crop | Patent Ref |
|---|---|---|---|---|---|
| A-5 | T120-7 | Bayer Crop Science (Aventis CropScience(AgrEvo)) | Introduction of the PPT-acetyltransferase (PAT) encoding gene from *Streptomyces viridochromogenes*, an aerobic soil bacteria. PPT normally acts to inhibit glutamine synthetase, causing a fatal accumulation of ammonia. Acetylated PPT is inactive. | *Beta vulgaris* (sugar beet) | |
| A-6 | T227-1 | WEYENS G; BARNES S; ROSQUIN I; SES EUROPE N.V./S.A | Glyphosate tolerance | *Beta vulgaris* (sugar beet) | US 2004-117870 |
| A-7 | 23-18-17, 23-198 | Monsanto Company (formerly Calgene) | High laurate (12:0) and myristate (14:0) canola produced by inserting a thioesterase encoding gene from the California bay laurel (*Umbellularia californica*). | *Brassica napus* (Argentine Canola) | |
| A-8 | 45A37, 46A40 | Pioneer Hi-Bred International Inc. | High oleic acid and low linolenic acid canola produced through a combination of chemical mutagenesis to select for a fatty acid desaturase mutant with elevated oleic acid, and traditional back-crossing to introduce the low linolenic acid trait. | *Brassica napus* (Argentine Canola) | |
| A-9 | 46A12, 46A16 | Pioneer Hi-Bred International Inc. | Combination of chemical mutagenesis, to achieve the high oleic acid trait, and traditional breeding with registered canola varieties. | *Brassica napus* (Argentine Canola) | |
| A-10 | GT200 | Monsanto Company | Glyphosate herbicide tolerant canola produced by inserting genes encoding the enzymes 5-enolypyruvylshikimate-3-phosphate synthase (EPSPS) from the CP4 strain of *Agrobacterium tumefaciens* and glyphosate oxidase from *Ochrobactrum anthropi*. | *Brassica napus* (Argentine Canola) | |
| A-11 | GT73, RT73 | Monsanto Company | Glyphosate herbicide tolerant canola produced by inserting genes encoding the enzymes 5-enolypyruvylshikimate-3-phosphate synthase (EPSPS) from the CP4 strain of *Agrobacterium tumefaciens* and glyphosate oxidase from *Ochrobactrum anthropi*. | *Brassica napus* (Argentine Canola) | |
| A-12 | HCN10 | Aventis CropScience | Introduction of the PPT-acetyltransferase (PAT) encoding gene from *Streptomyces viridochromogenes*, an aerobic soil bacteria. PPT normally acts to inhibit glutamine synthetase, causing a fatal accumulation of ammonia. Acetylated PPT is inactive. | *Brassica napus* (Argentine Canola) | |
| A-13 | HCN92 | Bayer Crop Science (Aventis CropScience(AgrEvo)) | Introduction of the PPT-acetyltransferase (PAT) encoding gene from *Streptomyces viridochromogenes*, an aerobic soil bacteria. PPT normally acts to inhibit | *Brassica napus* (Argentine Canola) | |

TABLE A-continued

Non-exclusive list of transgenic plants and events for the design of experiments with the compound of formula (I) related to the invention (source: (AGBIOS, P.O. Box 475, 106 St. John St. Merrickville, Ontario K0G1N0, CANADA) accessible under: http://www.agbios.com/dbase.php.

| | Event | Company | Description | Crop | Patent Ref |
|---|---|---|---|---|---|
| | | | glutamine synthetase, causing a fatal accumulation of ammonia. Acetylated PPT is inactive. | | |
| A-14 | MS1, RF1 => PGS1 | Aventis Crop Science (formerly Plant Genetic Systems) | Male-sterility, fertility restoration, pollination control system displaying glufosinate herbicide tolerance. MS lines contained the barnase gene from *Bacillus amyloliquefaciens*, RF lines contained the barstar gene from the same bacteria, and both lines contained the phosphinothricin N-acetyltransferase (PAT) encoding gene from *Streptomyces hygroscopicus*. | *Brassica napus* (Argentine Canola) | |
| A-15 | MS1, RF2 => PGS2 | Aventis CropScience (formerly Plant Genetic Systems) | Male-sterility, fertility restoration, pollination control system displaying glufosinate herbicide tolerance. MS lines contained the barnase gene from *Bacillus amyloliquefaciens*, RF lines contained the barstar gene from the same bacteria, and both lines contained the phosphinothricin N-acetyltransferase (PAT) encoding gene from *Streptomyces hygroscopicus*. | *Brassica napus* (Argentine Canola) | |
| A-16 | MS8xRF3 | Bayer CropScience (Aventis CropScience(AgrEvo)) | Male-sterility, fertility restoration, pollination control system displaying glufosinate herbicide tolerance. MS lines contained the barnase gene from *Bacillus amyloliquefaciens*, RF lines contained the barstar gene from the same bacteria, and both lines contained the phosphinothricin N-acetyltransferase (PAT) encoding gene from *Streptomyces hygroscopicus*. | *Brassica napus* (Argentine Canola) | |
| A-17 | MS-B2 | AVENTIS CROPSCIENCE N.V. | Male sterility | *Brassica napus* (Argentine Canola) | WO 01/31042 |
| A-18 | MS-BN1/RF-BN1 | AVENTIS CROPSCIENCE N.V. | Male sterility/restoration | *Brassica napus* (Argentine Canola) | WO 01/41558 |
| A-19 | NS738, NS1471, NS1473 | Pioneer Hi-Bred International Inc. | Selection of somaclonal variants with altered acetolactate synthase (ALS) enzymes, following chemical mutagenesis. Two lines (P1, P2) were initially selected with modifications at different unlinked loci. NS738 contains the P2 mutation only. | *Brassica napus* (Argentine Canola) | |
| A-20 | OXY-235 | Aventis CropScience (formerly Rhone Poulenc Inc.) | Tolerance to the herbicides bromoxynil and ioxynil by incorporation of the nitrilase gene from *Klebsiella pneumoniae*. | *Brassica napus* (Argentine Canola) | |
| A-21 | PHY14, PHY35 | Aventis CropScience (formerly Plant Genetic Systems) | Male sterility was via insertion of the barnase ribonuclease gene from *Bacillus amyloliquefaciens*; fertility restoration by insertion of the barstar RNase inhibitor; PPT resistance was | *Brassica napus* (Argentine Canola) | |

TABLE A-continued

Non-exclusive list of transgenic plants and events for the design of experiments with the compound of formula (I) related to the invention (source: (AGBIOS, P.O. Box 475, 106 St. John St. Merrickville, Ontario K0G1N0, CANADA) accessible under: http://www.agbios.com/dbase.php.

| | Event | Company | Description | Crop | Patent Ref |
|---|---|---|---|---|---|
| A-22 | PHY36 | Aventis CropScience (formerly Plant Genetic Systems) | via PPT-acetyltransferase (PAT) from *Streptomyces hygroscopicus*. Male sterility was via insertion of the barnase ribonuclease gene from *Bacillus amyloliquefaciens*; fertility restoration by insertion of the barstar RNase inhibitor; PPT resistance was via PPT-acetyltransferase (PAT) from *Streptomyces hygroscopicus*. | *Brassica napus* (Argentine Canola) | |
| A-23 | RT73 | MONSANTO TECHNOLOGY LLC | Glyphosate resistance | *Brassica napus* (Argentine Canola) | WO 02/36831 |
| A-24 | T45 (HCN28) | Bayer CropScience (Aventis CropScience(AgrEvo)) | Introduction of the PPT-acetyltransferase (PAT) encoding gene from *Streptomyces viridochromogenes*, an aerobic soil bacteria. PPT normally acts to inhibit glutamine synthetase, causing a fatal accumulation of ammonia. Acetylated PPT is inactive. | *Brassica napus* (Argentine Canola) | |
| A-25 | HCR-1 | Bayer CropScience (Aventis CropScience(AgrEvo)) | Introduction of the glufosinate ammonium herbicide tolerance trait from transgenic *B. napus* line T45. This trait is mediated by the phosphinothricin acetyltransferase (PAT) encoding gene from *S. viridochromogenes*. | *Brassica rapa* (Polish Canola) | |
| A-26 | ZSR500/ 502 | Monsanto Company | Introduction of a modified 5-enol-pyruvylshikimate-3-phosphate synthase (EPSPS) and a gene from *Achromobacter* sp that degrades glyphosate by conversion to aminomethylphosphonic acid (AMPA) and glyoxylate by interspecific crossing with GT73. | *Brassica rapa* (Polish Canola) | |
| A-27 | EE-1 | MAHARASHTRA HYBRID SEEDS COMPANY LIMITED (MAHYCO) | Insect resistance (Cry1Ac) | Brinjal | WO 2007/091277 |
| A-28 | 55-1/63-1 | Cornell University | Papaya ringspot virus (PRSV) resistant papaya produced by inserting the coat protein (CP) encoding sequences from this plant potyvirus. | *Carica papaya* (Papaya) | |
| A-29 | X17-2 | University of Florida | Papaya ringspot virus (PRSV) resistant papaya produced by inserting the coat protein (CP) encoding sequences from PRSV isolate H1K with a thymidine inserted after the initiation codon to yield a frameshift. Also contains nptII as a selectable marker. | *Carica papaya* (Papaya) | |
| A-30 | RM3-3, RM3-4, RM3-6 | Bejo Zaden BV | Male sterility was via insertion of the barnase ribonuclease gene from *Bacillus amyloliquefaciens*; PPT resistance was via the bar gene from *S.* | *Cichorium intybus* (Chicory) | |

TABLE A-continued

Non-exclusive list of transgenic plants and events for the design of experiments with the compound of formula (I) related to the invention (source: (AGBIOS, P.O. Box 475, 106 St. John St. Merrickville, Ontario K0G1N0, CANADA) accessible under: http://www.agbios.com/dbase.php.

| | Event | Company | Description | Crop | Patent Ref |
|---|---|---|---|---|---|
| A-31 | A, B | Agritope Inc. | *hygroscopicus*, which encodes the PAT enzyme. Reduced accumulation of S-adenosylmethionine (SAM), and consequently reduced ethylene synthesis, by introduction of the gene encoding S-adenosylmethionine hydrolase. | *Cucumis melo* (Melon) | |
| A-32 | CZW-3 | Asgrow (USA); Seminis Vegetable Inc. (Canada) | Cucumber mosiac virus (CMV), zucchini yellows mosaic (ZYMV) and watermelon mosaic virus (WMV) 2 resistant squash (*Curcurbita pepo*) produced by inserting the coat protein (CP) encoding sequences from each of these plant viruses into the host genome. | *Cucurbita pepo* (Squash) | |
| A-33 | ZW20 | Upjohn (USA); Seminis Vegetable Inc. (Canada) | Zucchini yellows mosaic (ZYMV) and watermelon mosaic virus (WMV) 2 resistant squash (*Curcurbita pepo*) produced by inserting the coat protein (CP) encoding sequences from each of these plant potyviruses into the host genome. | *Cucurbita pepo* (Squash) | |
| A-34 | 66 | Florigene Pty Ltd. | Delayed senescence and sulfonylurea herbicide tolerant carnations produced by inserting a truncated copy of the carnation aminocyclopropane cyclase (ACC) synthase encoding gene in order to suppress expression of the endogenous unmodified gene, which is required for normal ethylene biosynthesis. Tolerance to sulfonyl urea herbicides was via the introduction of a chlorsulfuron tolerant version of the acetolactate synthase (ALS) encoding gene from tobacco. | *Dianthus caryophyllus* (Carnation) | |
| A-35 | 4, 11, 15, 16 | Florigene Pty Ltd. | Modified colour and sulfonylurea herbicide tolerant carnations produced by inserting two anthocyanin biosynthetic genes whose expression results in a violet/mauve colouration. Tolerance to sulfonyl urea herbicides was via the introduction of a chlorsulfuron tolerant version of the acetolactate synthase (ALS) encoding gene from tobacco. | *Dianthus caryophyllus* (Carnation) | |
| A-36 | 959A, 988A, 1226A, 1351A, 1363A, 1400A | Florigene Pty Ltd. | Introduction of two anthocyanin biosynthetic genes to result in a violet/mauve colouration; Introduction of a variant form of acetolactate synthase (ALS). | *Dianthus caryophyllus* (Carnation) | |
| A-37 | 127 | BASF AGROCHEMICAL PRODUCTS B.V. | ALS/AHAS inhibitor-tolerance | *Glycine max* L. (Soybean) | WO2010080829 |

TABLE A-continued

Non-exclusive list of transgenic plants and events for the design of experiments with the compound of formula (I) related to the invention (source: (AGBIOS, P.O. Box 475, 106 St. John St. Merrickville, Ontario K0G1N0, CANADA) accessible under: http://www.agbios.com/dbase.php.

| | Event | Company | Description | Crop | Patent Ref |
|---|---|---|---|---|---|
| A-38 | 3560.4.3.5 | PIONEER HI-BRED INTERNATIONAL, INC | Glyphosate/ALS inhibitor-tolerance | Glycine max L. (Soybean) | WO 2008002872, US2010184079 |
| A-39 | A2704-12, A2704-21 | Bayer CropScience (Aventis CropScience(AgrEvo)) | Glufosinate ammonium herbicide tolerant soybean produced by inserting a modified phosphinothricin acetyltransferase (PAT) encoding gene from the soil bacterium *Streptomyces viridochromogenes* | Glycine max L. (Soybean) | WO 2006/108674 |
| A-40 | A5547-127 | Bayer CropScience (Aventis CropScience(AgrEvo)) | Glufosinate ammonium herbicide tolerant soybean produced by inserting a modified phosphinothricin acetyltransferase (PAT) encoding gene from the soil bacterium *Streptomyces viridochromogenes*. | Glycine max L. (Soybean) | |
| A-41 | A5547-35 | Bayer CropScience (Aventis CropScience(AgrEvo)) | Glufosinate tolerance | Glycine max L. (Soybean) | WO 2006/108675 |
| A-42 | DP-305423-1 | Pioneer Hi-Bred International Inc. | High oleic acid/ALS inhibitor tolerance | Glycine max L. (Soybean) | WO 2008/054747 |
| A-43 | DP356043 | Pioneer Hi-Bred International Inc. | Soybean event with two herbicide tolerance genes: glyphosate N-acetlytransferase, which detoxifies glyphosate, and a modified acetolactate synthase (A | Glycine max L. (Soybean) | |
| A-44 | G94-1, G94-19, G168 | DuPont Canada Agricultural Products | High oleic acid soybean produced by inserting a second copy of the fatty acid desaturase (GmFad2-1) encoding gene from soybean, which resulted in "silencing" of the endogenous host gene. | Glycine max L. (Soybean) | |
| A-45 | GTS 40-3-2 | Monsanto Company | Glyphosate tolerant soybean variety produced by inserting a modified 5-enolpyruvylshikimate-3-phosphate synthase (EPSPS) encoding gene from the soil bacterium *Agrobacterium tumefaciens*. | Glycine max L. (Soybean) | |
| A-46 | GU262 | Bayer CropScience (Aventis CropScience(AgrEvo)) | Glufosinate ammonium herbicide tolerant soybean produced by inserting a modified phosphinothricin acetyltransferase (PAT) encoding gene *Streptomyces viridochromogenes*. | Glycine max L. (Soybean) | |
| A-47 | MON87701 | Monsanto Company | insect resistance (CryIac) | Glycine max L. (Soybean) | WO 2009064652 |
| A-48 | MON87705 | Monsanto Company | altered fatty acid levels (mid-oleic and low saturate) | Glycine max L. (Soybean) | WO 2010037016 |
| A-49 | MON87754 | Monsanto Company | increased oil content | Glycine max L. (Soybean) | WO 2010024976 |
| A-50 | MON87769 | Monsanto Company | stearidonic acid (SDA) comprising oil | Glycine max L. (Soybean) | WO 2009102873 |
| A-51 | MON89788 | Monsanto Company | Glyphosate-tolerant soybean produced by inserting a modified 5-enolpyruvylshikimate-3-phosphate synthase (EPSPS) encoding aroA (epsps) gene from *Agrobacterium tumefaciens* CP4 | Glycine max L. (Soybean) | WO2006130436 |

TABLE A-continued

Non-exclusive list of transgenic plants and events for the design of experiments with the compound of formula (I) related to the invention (source: (AGBIOS, P.O. Box 475, 106 St. John St. Merrickville, Ontario K0G1N0, CANADA) accessible under: http://www.agbios.com/dbase.php.

| | Event | Company | Description | Crop | Patent Ref |
|---|---|---|---|---|---|
| A-52 | MON19788 | Monsanto Company | Glyphosate tolerance | Glycine max L. (Soybean) | WO2006130436 |
| A-53 | OT96-15 | Agriculture & Agri-Food Canada | Low linolenic acid soybean produced through traditional cross-breeding to incorporate the novel trait from a naturally occurring fan1 gene mutant that was selected for low linolenic acid. | Glycine max L. (Soybean) | |
| A-54 | W62, W98 | Bayer CropScience (Aventis CropScience(AgrEvo)) | Glufosinate ammonium herbicide tolerant soybean produced by inserting a modified phosphinothricin acetyltransferase (PAT) encoding gene from the soil bacterium *Streptomyces hygroscopicus*. | Glycine max L. (Soybean) | |
| A-55 | MON87708 | MONSANTO TECHNOLOGY LLC | Dicamba herbicide tolerance, transformation vector PV-GMHT4355 1) DMO: full length transcript (Peanut Chlorotic Streak Virus) promoter > tobacco Etch Virus leader > ribulose 1,5-biphosphate carboxylase small subunit (*Pisum sativum*) chloroplast transit peptide > dicamba mono-oxygenase (*Stenotrophomonas maltophilia*) coding sequence > ribulose-1,5-bisphosphate carboxylase small subunit E9 (*Pisum sativum*) 3'-untranslated region. A CP4 epsps chimeric gene contained within a second T-DNA on the transformation vector used was segregated away. | Glycine max L. (Soybean) | WO 2011034704 |
| A-56 | EE-GM3/FG72 | BAYER BIOSCIENCE NV [BE]; MS TECHNOLOGIES LLC [US] | 1) Ph4a748 ABBC: sequence including the promoter region of the histone H4 gene of *Arabidopsis thaliana*, containing an internal duplication>5'tev: sequence including the leader sequence of the tobacco etch virus>TPotp Y: coding sequence of an optimized transit peptide derivative (position 55 changed into Tyrosine), containing sequence of the RuBisCO small subunit genes of *Zea mays* (corn) and *Helianthus annuus* (sunflower)>hppdPf W336: the coding sequence of the 4-hydroxyphenylpyruvate dioxygenase of *Pseudomonas fluorescens* strain A32 modified by the replacement of the amino acid *Glycine* 336 with a Tryptophane>3'nos: sequence including the 3' untranslated region of the nopaline synthase gene from the T-DNA of pTiT37 of *Agrobacterium tumefaciens*. 2) Ph4a748: sequence including the promoter region of the histone H4 gene of | Glycine max L. (Soybean) | WO 2011063411 |

TABLE A-continued

Non-exclusive list of transgenic plants and events for the design of experiments with the compound of formula (I) related to the invention (source: (AGBIOS, P.O. Box 475, 106 St. John St. Merrickville, Ontario K0G1N0, CANADA) accessible under: http://www.agbios.com/dbase.php.

| | Event | Company | Description | Crop | Patent Ref |
|---|---|---|---|---|---|
| A-57 | 416/ pDAB44 68-0416 | DOW AGROSCIENCES LLC | *Arabidopsis thaliana*>intron1 h3At: first intron of gene II of the histone H3.III variant of *Arabidopsis thaliana* >TPotp C: coding sequence of the optimized transit peptide, containing sequence o A novel aad-12 transformation event for herbicide tolerance in soybean plants - referred to herein as pDAB4468-0416. The aad-12 gene (originally from *Delftia acidovorans*) encodes the aryloxyalkanoate dioxygenase (AAD-12) protein. The trait confers tolerance to 2,4-dichlorophenoxyacetic acid, for example, and to pyridyloxyacetate herbicides. The aad-12 gene, itself, for herbicide tolerance in plants | *Glycine max* L. (Soybean) | WO 2011066384, WO 2007/053482. |
| A-58 | 15985 | Monsanto Company | Insect resistant cotton derived by transformation of the DP50B parent variety, which contained event 531 (expressing Cry1Ac protein), with purified plasmid DNA containing the cry2Ab gene from *B. thuringiensis* subsp. *kurstaki*. | *Gossypium hirsutum* L. (Cotton) | |
| A-59 | 1143-14A | SYNGENTA PARTICIPA-TIONS AG | Insect resistance (Cry1Ab) | *Gossypium hirsutum* L. (Cotton) | WO 2006/128569 |
| A-60 | 1143-51B | SYNGENTA PARTICIPA-TIONS AG | Insect resistance (Cry1Ab) | *Gossypium hirsutum* L. (Cotton) | WO 2006/128570 |
| A-61 | 19-51A | DuPont Canada Agricultural Products | Introduction of a variant form of acetolactate synthase (ALS). | *Gossypium hirsutum* L. (Cotton) | |
| A-62 | 281-24-236 | DOW AgroSciences LLC | Insect-resistant cotton produced by inserting the cry1F gene from *Bacillus thuringiensis* var. *aizawai*. The PAT encoding gene from *Streptomyces viridochromogenes* was introduced as a selectable marker. | *Gossypium hirsutum* L. (Cotton) | |
| A-63 | 3006-210-23 | DOW AgroSciences LLC | Insect-resistant cotton produced by inserting the cry1Ac gene from *Bacillus thuringiensis* subsp. *kurstaki*. The PAT encoding gene from *Streptomyces viridochromogenes* was introduced as a selectable marker. | *Gossypium hirsutum* L. (Cotton) | |
| A-64 | 31807/31808 | Calgene Inc. | Insect-resistant and bromoxynil herbicide tolerant cotton produced by inserting the cry1Ac gene from *Bacillus thuringiensis* and a nitrilase encoding gene from *Klebsiella pneumoniae*. | *Gossypium hirsutum* L. (Cotton) | |
| A-65 | BXN | Calgene Inc. | Bromoxynil herbicide tolerant cotton produced by inserting a nitrilase encoding gene from *Klebsiella pneumoniae*. | *Gossypium hirsutum* L. (Cotton) | |

TABLE A-continued

Non-exclusive list of transgenic plants and events for the design of experiments with the compound of formula (I) related to the invention (source: (AGBIOS, P.O. Box 475, 106 St. John St. Merrickville, Ontario K0G1N0, CANADA) accessible under: http://www.agbios.com/dbase.php.

| | Event | Company | Description | Crop | Patent Ref |
|---|---|---|---|---|---|
| A-66 | CE43-67B | SYNGENTA PARTICIPA-TIONS AG | Insect resistance (Cry1Ab) | *Gossypium hirsutum* L. (Cotton) | WO 2006/128573, US 2011020828 |
| A-67 | CE44-69D | SYNGENTA PARTICIPA-TIONS AG | Insect resistance (Cry1Ab) | *Gossypium hirsutum* L. (Cotton) | WO 2006/128571 |
| A-68 | CE46-02A | SYNGENTA PARTICIPA-TIONS AG | Insect resistance (Cry1Ab) | *Gossypium hirsutum* L. (Cotton) | WO 2006/128572 |
| A-69 | Cot102 | Syngenta Seeds, Inc. | Insect-resistant cotton produced by inserting the vip3A(a) gene from *Bacillus thuringiensis* AB88. The APH4 encoding gene from *E. coli* was introduced as a selectable marker | *Gossypium hirsutum* L. (Cotton) | US 2006-130175, WO2004039986, US 2010298553 |
| A-70 | COT202 | Syngenta Seeds, Inc. | Insect resistance (VIP3A) | *Gossypium hirsutum* L. (Cotton) | US2009181399 |
| A-71 | Cot202 | Syngenta Seeds, Inc. | Insect resistance (VIP3) | *Gossypium hirsutum* L. (Cotton) | US 2007-067868 |
| A-72 | Cot67B | Syngenta Seeds, Inc. | Insect-resistant cotton produced by inserting a full-length cry1Ab gene from *Bacillus thuringiensis*. The APH4 encoding gene from *E. coli* was introduced as a selectable marker. | *Gossypium hirsutum* L. (Cotton) | |
| A-73 | DAS-21Ø23-5 × DAS-24236-5 | DOW AgroSciences LLC | WideStrike ™, a stacked insect-resistant cotton derived from conventional cross-breeding of parental lines 3006-210-23 (OECD identifier: DAS-21Ø023-5) and 281-24-236 (OECD identifier: DAS-24236-5). | *Gossypium hirsutum* L. (Cotton) | |
| A-74 | DAS-21Ø23-5 × DAS-24236-5 × MON88913 | DOW AgroSciences LLC and Pioneer Hi-Bred International Inc. | Stacked insect-resistant and glyphosate-tolerant cotton derived from conventional cross-breeding of WideStrike cotton (OECD identifier: DAS-21Ø23-5 × DAS-24236-5) with MON88913, known as RoundupReady Flex (OECD identifier: MON-88913-8). | *Gossypium hirsutum* L. (Cotton) | |
| A-75 | DAS-21Ø23-5 × DAS-24236-5 × MON-Ø1445-2 | DOW AgroSciences LLC | WideStrike ™/Roundup Ready ® cotton, a stacked insect-resistant and glyphosate-tolerant cotton derived from conventional cross-breeding of WideStrike cotton (OECD identifier: DAS-21Ø23-5 × DAS-24236-5) with MON1445 (OECD identifier: MON-Ø1445-2). | *Gossypium hirsutum* L. (Cotton) | |
| A-76 | EE-GH3 | BAYER BIOSCIENCE N.V. | Glyphosate tolerance | *Gossypium hirsutum* L. (Cotton) | WO 2007/017186 |
| A-77 | EE-GH5 | BAYER BIOSCIENCE N.V. | Insect resistance (Cry1Ab) | *Gossypium hirsutum* L. (Cotton) | WO 2008/122406 |
| A-78 | EE-GH6 | BAYER BIOSCIENCE N.V. | Insect resistance (cry2Ae) | *Gossypium hirsutum* L. (Cotton) | WO2008151780, US2010218281 |
| A-79 | event 281-24-236 | DOW AGROSCIENCES LLC | Insect resistance (Cry1F) | *Gossypium hirsutum* L. (Cotton) | WO 2005/103266 |
| A-80 | Event-1 | JK Agri Genetics Ltd (India) | Insect-resistant cotton produced by inserting the cry1Ac gene from *Bacillus* | *Gossypium hirsutum* L. (Cotton) | |

TABLE A-continued

Non-exclusive list of transgenic plants and events for the design of experiments with the compound of formula (I) related to the invention (source: (AGBIOS, P.O. Box 475, 106 St. John St. Merrickville, Ontario K0G1N0, CANADA) accessible under: http://www.agbios.com/dbase.php.

| | Event | Company | Description | Crop | Patent Ref |
|---|---|---|---|---|---|
| | | | *thuringiensis* subsp. *kurstaki* HD-73 (B.t.k.). | | |
| A-81 | event300 6-210-23 | DOW AGROSCIENCES LLC | Insect resistance (Cry1Ac) | *Gossypium hirsutum* L. (Cotton) | WO 2005/103266 |
| A-82 | GBH614 | Bayer CropScience (Aventis CropScience(AgrEvo)) | Glyphosate herbicide tolerant cotton produced by inserting 2mepsps gene into variety Coker312 by *Agrobacterium* under the control of Ph4a748At and TPotpC | *Gossypium hirsutum* L. (Cotton) | |
| A-83 | LLCotton25 | Bayer CropScience (Aventis CropScience(AgrEvo)) | Glufosinate ammonium herbicide tolerant cotton produced by inserting a modified phosphinothricin acetyltransferase (PAT) encoding gene from the soil bacterium *Streptomyces hygroscopicus* | *Gossypium hirsutum* L. (Cotton) | WO2003013224, WO 2007/017186 |
| A-84 | LLCotton25 × MON15985 | Bayer CropScience (Aventis CropScience(AgrEvo)) | Stacked herbicide tolerant and insect resistant cotton combining tolerance to glufosinate ammonium herbicide from LLCotton25 (OECD identifier: ACS-GHØØ1-3) with resistance to insects from MON15985 (OECD identifier: MON-15985-7) | *Gossypium hirsutum* L. (Cotton) | |
| A-85 | MON15985 | MONSANTO TECHNOLOGY LLC | Insect resistance (Cry1Ac/Cry2Ab) | *Gossypium hirsutum* L. (Cotton) | US 2004-250317 |
| A-86 | MON1445/1698 | Monsanto Company | Glyphosate herbicide tolerant cotton produced by inserting a naturally glyphosate tolerant form of the enzyme 5-enolpyruvyl shikimate-3-phosphate synthase (EPSPS) from *A. tumefaciens* strain CP4. | *Gossypium hirsutum* L. (Cotton) | |
| A-87 | MON15985 × MON88913 | Monsanto Company | Stacked insect resistant and glyphosate tolerant cotton produced by conventional cross-breeding of the parental lines MON88913 (OECD identifier: MON-88913-8) and 15985 (OECD identifier: MON-15985-7). Glyphosate tolerance is derived from MON88913 which contains two genes encoding the enzyme 5-enolypyruvylshikimate-3-phosphate synthase (EPSPS) from the CP4 strain of *Agrobacterium tumefaciens*. Insect resistance is derived MON15985 which was produced by transformation of the DP50B parent variety, which contained event 531 (expressing Cry1Ac protein), with purified plasmid DNA containing the cry2Ab gene from *B. thuringiensis* subsp. *kurstaki*. | *Gossypium hirsutum* L. (Cotton) | |
| A-88 | MON-15985-7 × MON-Ø1445-2 | Monsanto Company | Stacked insect resistant and herbicide tolerant cotton derived from conventional cross-breeding of the parental lines 15985 (OECD identifier: MON-15985-7) and MON1445 (OECD identifier: MON-Ø1445-2). | *Gossypium hirsutum* L. (Cotton) | |

TABLE A-continued

Non-exclusive list of transgenic plants and events for the design of experiments with the compound of formula (I) related to the invention (source: (AGBIOS, P.O. Box 475, 106 St. John St. Merrickville, Ontario K0G1N0, CANADA) accessible under: http://www.agbios.com/dbase.php.

| | Event | Company | Description | Crop | Patent Ref |
|---|---|---|---|---|---|
| A-89 | MON531/ 757/1076 | Monsanto Company | Insect-resistant cotton produced by inserting the cry1Ac gene from *Bacillus thuringiensis* subsp. *kurstaki* HD-73 (B.t.k.). | *Gossypium hirsutum* L. (Cotton) | |
| A-90 | MON531/ 757/1076 | Monsanto Company | Insect-resistant cotton produced by inserting the cry1Ac gene from *Bacillus thuringiensis* subsp. *kurstaki* HD-73 (B.t.k.). | *Gossypium hirsutum* L. (Cotton) | |
| A-91 | MON88913 | Monsanto Company | Glyphosate herbicide tolerant cotton produced by inserting two genes encoding the enzyme 5-enolypyruvylshikimate-3-phosphate synthase (EPSPS) from the CP4 strain of *Agrobacterium tumefaciens*,; WO 2004/072235 | *Gossypium hirsutum* L. (Cotton) | WO 2004/072235 |
| A-92 | MON-ØØ531-6 × MON-Ø1445-2 | Monsanto Company | Stacked insect resistant and herbicide tolerant cotton derived from conventional cross-breeding of the parental lines MON531 (OECD identifier: MON-ØØ531-6) and MON1445 (OECD identifier: MON-Ø1445-2). | *Gossypium hirsutum* L. (Cotton) | |
| A-93 | PV-GHGT07 (1445) | MONSANTO TECHNOLOGY LLC BAYER BIOSCIENCE NV | Glyphosate tolerance | *Gossypium hirsutum* L. (Cotton) | US 2004-148666 |
| A-94 | T304-40 | | Insect-resistance (Cry1Ab) | *Gossypium hirsutum* L. (Cotton) | WO2008/122406, US2010077501 |
| A-95 | T342-142 | SYNGENTA PARTICIPA-TIONS AG | Insect resistance (Cry1Ab) | *Gossypium hirsutum* L. (Cotton) | WO 2006/128568 |
| A-96 | LLcotton25 | BAYER BIOSCIENCE N.V. | Glufosinate resistance | *Gossypium hirsutum* L. (Cotton) | WO 2003013224 |
| A-97 | X81359 | BASF Inc. | Tolerance to imidazolinone herbicides by selection of a naturally occurring mutant. | *Helianthus annuus* (Sunflower) | |
| A-98 | RH44 | BASF Inc. | Selection for a mutagenized version of the enzyme acetohydroxyacid synthase (AHAS), also known as acetolactate synthase (ALS) or acetolactate pyruvate-lyase. | *Lens culinaris* (Lentil) | |
| A-99 | FP967 | University of Saskatchewan, Crop Dev. Centre | A variant form of acetolactate synthase (ALS) was obtained from a chlorsulfuron tolerant line of *A. thaliana* and used to transform flax. | *Linum usitatissimum* L. (Flax, Linseed) | |
| A-100 | 5345 | Monsanto Company | Resistance to lepidopteran pests through the introduction of the cry1Ac gene from *Bacillus thuringiensis* subsp. *Kurstaki*. | *Lycopersicon esculentum* (Tomato) | |
| A-101 | 8338 | Monsanto Company | Introduction of a gene sequence encoding the enzyme 1-amino-cyclopropane-1-carboxylic acid deaminase (ACCd) that metabolizes the precursor of the fruit ripening hormone ethylene. | *Lycopersicon esculentum* (Tomato) | |
| A-102 | 1345-4 | DNA Plant Technology Corporation | Delayed ripening tomatoes produced by inserting an additional copy of a truncated gene encoding 1- | *Lycopersicon esculentum* (Tomato) | |

TABLE A-continued

Non-exclusive list of transgenic plants and events for the design of experiments with the compound of formula (I) related to the invention (source: (AGBIOS, P.O. Box 475, 106 St. John St. Merrickville, Ontario K0G1N0, CANADA) accessible under: http://www.agbios.com/dbase.php.

| | Event | Company | Description | Crop | Patent Ref |
|---|---|---|---|---|---|
| | | | aminocyclopropane-1-carboxyllic acid (ACC) synthase, which resulted in downregulation of the endogenous ACC synthase and reduced ethylene accumulation. | | |
| A-103 | 35 1 N | Agritope Inc. | Introduction of a gene sequence encoding the enzyme S-adenosylmethionine hydrolase that metabolizes the precursor of the fruit ripening hormone ethylene | Lycopersicon esculentum (Tomato) | |
| A-104 | B, Da, F | Zeneca Seeds | Delayed softening tomatoes produced by inserting a truncated version of the polygalacturonase (PG) encoding gene in the sense or anti-sense orientation in order to reduce expression of the endogenous PG gene, and thus reduce pectin degradation. | Lycopersicon esculentum (Tomato) | |
| A-105 | FLAVR SAVR | Calgene Inc. | Delayed softening tomatoes produced by inserting an additional copy of the polygalacturonase (PG) encoding gene in the anti-sense orientation in order to reduce expression of the endogenous PG gene and thus reduce pectin degradation. | Lycopersicon esculentum (Tomato) | |
| A-106 | J101, J163 | Monsanto Company and Forage Genetics International | Glyphosate herbicide tolerant alfalfa (lucerne) produced by inserting a gene encoding the enzyme 5-enolypyruvylshikimate-3-phosphate synthase (EPSPS) from the CP4 strain of *Agrobacterium tumefaciens*. | Medicago sativa (Alfalfa) | |
| A-107 | C/F/93/08-02 | Societe National d'Exploitation des Tabacs et Allumettes | Tolerance to the herbicides bromoxynil and ioxynil by incorporation of the nitrilase gene from *Klebsiella pneumoniae*. | Nicotiana tabacum L. (Tobacco) | |
| A-108 | Vector 21-41 | Vector Tobacco Inc. | Reduced nicotine content through introduction of a second copy of the tobacco quinolinic acid phosphoribosyltransferase (QTPase) in the antisense orientation. The NPTII encoding gene from *E. coli* was introduced as a selectable marker to identify transformants. | Nicotiana tabacum L. (Tobacco) | |
| A-109 | 17053 | MONSANTO TECHNOLOGY LLC | Glyphosate tolerance | Oryza sativa (Rice) | WO2010117737 |
| A-110 | 17314 | MONSANTO TECHNOLOGY LLC | Glyphosate tolerance | Oryza sativa (Rice) | WO2010117735 |
| A-111 | CL121, CL141, CFX51 | BASF Inc. | Tolerance to the imidazolinone herbicide, imazethapyr, induced by chemical mutagenesis of the acetolactate synthase (ALS) enzyme using ethyl methanesulfonate (EMS). | Oryza sativa (Rice) | |
| A-112 | GAT-OS2 | AVENTIS CROPSCIENCE, N.V. | Glufosinate tolerance | Oryza sativa (Rice) | WO 01/83818 |

TABLE A-continued

Non-exclusive list of transgenic plants and events for the design of experiments with the compound of formula (I) related to the invention (source: (AGBIOS, P.O. Box 475, 106 St. John St. Merrickville, Ontario K0G1N0, CANADA) accessible under: http://www.agbios.com/dbase.php.

| | Event | Company | Description | Crop | Patent Ref |
|---|---|---|---|---|---|
| A-113 | GAT-OS3 | BAYER BIOSCIENCE NV | Glufosinate tolerance | *Oryza sativa* (Rice) | US 2008-289060 |
| A-114 | IMINTA-1, IMINTA-4 | BASF Inc. | Tolerance to imidazolinone herbicides induced by chemical mutagenesis of the acetolactate synthase (ALS) enzyme using sodium azide. | *Oryza sativa* (Rice) | |
| A-115 | LLRICE 06, LLRICE 62 | Aventis CropScience | Glufosinate ammonium herbicide tolerant rice produced by inserting a modified phosphinothricin acetyltransferase (PAT) encoding gene from the soil bacterium *Streptomyces hygroscopicus*). | *Oryza sativa* (Rice) | |
| A-116 | LLRICE 601 | Bayer CropScience (Aventis CropScience(AgrEvo)) | Glufosinate ammonium herbicide tolerant rice produced by inserting a modified phosphinothricin acetyltransferase (PAT) encoding gene from the soil bacterium *Streptomyces hygroscopicus*). | *Oryza sativa* (Rice) | |
| A-117 | PE-7 | MAHARASHTRA HYBRID SEEDS COMPANY LIMITED | Insect resistance (Cry1Ac) | *Oryza sativa* (Rice) | WO 2008/114282 |
| A-118 | PWC16 | BASF Inc. | Tolerance to the imidazolinone herbicide, imazethapyr, induced by chemical mutagenesis of the acetolactate synthase (ALS) enzyme using ethyl methanesulfonate (EMS). | *Oryza sativa* (Rice) | |
| A-119 | TT51 | UNIV ZHEJIANG | Insect resistance (Cry1Ab/Cry1Ac) | *Oryza sativa* (Rice) | CN1840655 |
| A-120 | Kefeng No. 6 | CHINA NAT RICE RES INST | Transgenic rice Kefeng 6 is a transformation event containing two insect-resistant genes, cry1Ac and SCK (modified CpTI gene) in China. | *Oryza sativa* (Rice) | CN 101824411 |
| A-121 | C5 | United States Department of Agriculture - Agricultural Research Service | Plum pox virus (PPV) resistant plum tree produced through *Agrobacterium*-mediated transformation with a coat protein (CP) gene from the virus. | *Prunus domestica* (Plum) | |
| A-122 | ATBT04-6, ATBT04-27, ATBT04-30, ATBT04-31, ATBT04-36, SPBT02-5, SPBT02-7 | Monsanto Company | Colorado potato beetle resistant potatoes produced by inserting the cry3A gene from *Bacillus thuringiensis* (subsp. *Tenebrionis*). | *Solanum tuberosum* L. (Potato) | |
| A-123 | BT6, BT10, BT12, BT16, BT17, BT18, BT23 | Monsanto Company | Colorado potato beetle resistant potatoes produced by inserting the cry3A gene from *Bacillus thuringiensis* (subsp. *Tenebrionis*). | *Solanum tuberosum* L. (Potato) | |
| A-124 | RBMT15-101, SEMT15-02, SEMT15-15 | Monsanto Company | Colorado potato beetle and potato virus Y (PVY) resistant potatoes produced by inserting the cry3A gene from *Bacillus thuringiensis* (subsp. *Tenebrionis*) and the coat protein encoding gene from PVY. | *Solanum tuberosum* L. (Potato) | |

TABLE A-continued

Non-exclusive list of transgenic plants and events for the design of experiments with the compound of formula (I) related to the invention (source: (AGBIOS, P.O. Box 475, 106 St. John St. Merrickville, Ontario K0G1N0, CANADA) accessible under: http://www.agbios.com/dbase.php.

| | Event | Company | Description | Crop | Patent Ref |
|---|---|---|---|---|---|
| A-125 | RBMT21-129, RBMT21-350, RBMT22-082 | Monsanto Company | Colorado potato beetle and potato leafroll virus (PLRV) resistant potatoes produced by inserting the cry3A gene from Bacillus thuringiensis (subsp. Tenebrionis) and the replicase encoding gene from PLRV. | Solanum tuberosum L. (Potato) | |
| A-126 | EH92-527 | BASF Plant Science | Crop composition; Amflora; Unique EU identifier: BPS-25271-9 | Solanum tuberosum L. (Potato) | |
| A-127 | AP205CL | BASF Inc. | Selection for a mutagenized version of the enzyme acetohydroxyacid synthase (AHAS), also known as acetolactate synthase (ALS) or acetolactate pyruvate-lyase. | Triticum aestivum (Wheat) | |
| A-128 | AP602CL | BASF Inc. | Selection for a mutagenized version of the enzyme acetohydroxyacid synthase (AHAS), also known as acetolactate synthase (ALS) or acetolactate pyruvate-lyase. | Triticum aestivum (Wheat) | |
| A-129 | BW255-2, BW238-3 | BASF Inc. | Selection for a mutagenized version of the enzyme acetohydroxyacid synthase (AHAS), also known as acetolactate synthase (ALS) or acetolactate pyruvate-lyase. | Triticum aestivum (Wheat) | |
| A-130 | BW7 | BASF Inc. | Tolerance to imidazolinone herbicides induced by chemical mutagenesis of the acetohydroxyacid synthase (AHAS) gene using sodium azide. | Triticum aestivum (Wheat) | |
| A-131 | Event 1 | SYNGENTA PARTICIPA-TIONS AG | Fusarium resistance (trichothecene 3-O-acetyltransferase) | Triticum aestivum (Wheat) | CA 2561992 |
| A-132 | JOPLIN1 | SYNGENTA PARTICIPA-TIONS AG | disease (fungal) resistance (trichothecene 3-O-acetyltransferase) | Triticum aestivum (Wheat) | WO; US 2008064032 |
| A-133 | MON71800 | Monsanto Company | Glyphosate tolerant wheat variety produced by inserting a modified 5-enolpyruvylshikimate-3-phosphate synthase (EPSPS) encoding gene from the soil bacterium Agrobacterium tumefaciens, strain CP4. | Triticum aestivum (Wheat) | |
| A-134 | SWP965001 | Cyanamid Crop Protection | Selection for a mutagenized version of the enzyme acetohydroxyacid synthase (AHAS), also known as acetolactate synthase (ALS) or acetolactate pyruvate-lyase. | Triticum aestivum (Wheat) | |
| A-135 | Teal 11A | BASF Inc. | Selection for a mutagenized version of the enzyme acetohydroxyacid synthase (AHAS), also known as acetolactate synthase (ALS) or acetolactate pyruvate-lyase. | Triticum aestivum (Wheat) | |
| A-136 | 176 | Syngenta Seeds, Inc. | Insect-resistant maize produced by inserting the cry1Ab gene from Bacillus thuringiensis subsp. kurstaki. The genetic modification affords resistance to attack by the European corn borer (ECB). | Zea mays L. (Maize) | |

TABLE A-continued

Non-exclusive list of transgenic plants and events for the design of experiments with the compound of formula (I) related to the invention (source: (AGBIOS, P.O. Box 475, 106 St. John St. Merrickville, Ontario K0G1N0, CANADA) accessible under: http://www.agbios.com/dbase.php.

| | Event | Company | Description | Crop | Patent Ref |
|---|---|---|---|---|---|
| A-137 | 3272 | SYNGENTA PARTICIPATIONS AG | Self processing corn (alpha-amylase) | *Zea mays* L. (Maize) | US 2006-230473, US2010063265 |
| A-138 | 5307 | SYNGENTA PARTICIPATIONS AG | Insect (corn rootworm) resistance (FR8a) | *Zea mays* L. (Maize) | WO2010077816 |
| A-139 | 3751IR | Pioneer Hi-Bred International Inc. | Selection of somaclonal variants by culture of embryos on imidazolinone containing media. | *Zea mays* L. (Maize) | |
| A-140 | 676, 678, 680 | Pioneer Hi-Bred International Inc. | Male-sterile and glufosinate ammonium herbicide tolerant maize produced by inserting genes encoding DNA adenine methylase and phosphinothricin acetyltransferase (PAT) from *Escherichia coli* and *Streptomyces viridochromogenes*, respectively. | *Zea mays* L. (Maize) | |
| A-141 | ACS-ZMØØ3-2 × MON-ØØ81Ø-6 | Bayer CropScience (Aventis CropScience(AgrEvo)) | Stacked insect resistant and herbicide tolerant corn hybrid derived from conventional cross-breeding of the parental lines T25 (OECD identifier: ACS-ZMØØ3-2) and MON810 (OECD identifier: MON-ØØ81Ø-6). | *Zea mays* L. (Maize) | |
| A-142 | B16 | DEKALB GENETICS CORP | Glufosinate resistance | *Zea mays* L. (Maize) | US 2003-126634 |
| A-143 | B16 (DLL25) | Dekalb Genetics Corporation | Glufosinate ammonium herbicide tolerant maize produced by inserting the gene encoding phosphinothricin acetyltransferase (PAT) from *Streptomyces hygroscopicus*. | *Zea mays* L. (Maize) | |
| A-144 | BT11 (X4334CBR, X4734CBR) | Syngenta Seeds, Inc. | Insect-resistant and herbicide tolerant maize produced by inserting the cry1Ab gene from *Bacillus thuringiensis* subsp. *kurstaki*, and the phosphinothricin N-acetyltransferase (PAT) encoding gene from *S. viridochromogenes*. | *Zea mays* L. (Maize) | WO 2010148268 |
| A-145 | BT11 × GA21 | Syngenta Seeds, Inc. | Stacked insect resistant and herbicide tolerant maize produced by conventional cross breeding of parental lines BT11 (OECD unique identifier: SYN-BTØ11-1) and GA21 (OECD unique identifier: MON-ØØØ21-9). | *Zea mays* L. (Maize) | |
| A-146 | BT11 × MIR162 | Syngenta Seeds, Inc. | Stacked insect resistant and herbicide tolerant maize produced by conventional cross breeding of parental lines BT11 (OECD unique identifier: SYN-BTØ11-1) and MIR162 (OECD unique identifier: SYN-IR162-4). Resistance to the European Corn Borer and tolerance to the herbicide glufosinate ammonium (Liberty) is derived from BT11, which contains the cry1Ab gene from *Bacillus thuringiensis* subsp. *kurstaki*, and the phosphinothricin N-acetyltransferase (PAT) | *Zea mays* L. (Maize) | |

TABLE A-continued

Non-exclusive list of transgenic plants and events for the design of experiments with the compound of formula (I) related to the invention (source: (AGBIOS, P.O. Box 475, 106 St. John St. Merrickville, Ontario K0G1N0, CANADA) accessible under: http://www.agbios.com/dbase.php.

| Event | | Company | Description | Crop | Patent Ref |
|---|---|---|---|---|---|
| | | | encoding gene from *S. viridochromogenes*. Resistance to other lepidopteran pests, including *H. zea, S. frugiperda, A. ipsilon*, and *S. albicosta*, is derived from MIR162, which contains the vip3Aa gene from *Bacillus thuringiensis* strain AB88. | | |
| A-147 | BT11 × MIR162 × MIR604 | Syngenta Seeds, Inc. | *Bacillus thuringiensis* Cry1Ab delta-endotoxin protein and the genetic material necessary for its production (via elements of vector pZO1502) in Event Bt11 corn (OECD Unique Identifier: SYN-BTØ11-1) × *Bacillus thuringiensis* Vip3Aa20 insecticidal protein and the genetic material necessary for its production (via elements of vector pNOV1300) in Event MIR162 maize (OECD Unique Identifier: SYN-IR162-4) × modified Cry3A protein and the genetic material necessary for its production (via elements of vector pZM26) in Event MIR604 corn (OECD Unique Identifier: SYN-IR6Ø4-5). | *Zea mays* L. (Maize) | |
| A-148 | BT11 × MIR604 | Syngenta Seeds, Inc. | Stacked insect resistant and herbicide tolerant maize produced by conventional cross breeding of parental lines BT11 (OECD unique identifier: SYN-BTØ11-1) and MIR604 (OECD unique identifier: SYN-IR6Ø5-5). Resistance to the European Corn Borer and tolerance to the herbicide glufosinate ammonium (Liberty) is derived from BT11, which contains the cry1Ab gene from *Bacillus thuringiensis* subsp. *kurstaki*, and the phosphinothricin N-acetyltransferase (PAT) encoding gene from *S. viridochromogenes*. Corn rootworm-resistance is derived from MIR604 which contains the mcry3A gene from *Bacillus thuringiensis*. | *Zea mays* L. (Maize) | |
| A-149 | BT11 × MIR604 × GA21 | Syngenta Seeds, Inc. | Stacked insect resistant and herbicide tolerant maize produced by conventional cross breeding of parental lines BT11 (OECD unique identifier: SYN-BTØ11-1), MIR604 (OECD unique identifier: SYN-IR6Ø5-5) and GA21 (OECD unique identifier: MON-ØØØ21-9). Resistance to the European Corn Borer and tolerance to the herbicide glufosinate ammonium (Liberty) is derived from BT11, which contains the cry1Ab gene from *Bacillus thuringiensis* | *Zea mays* L. (Maize) | |

TABLE A-continued

Non-exclusive list of transgenic plants and events for the design of experiments with the compound of formula (I) related to the invention (source: (AGBIOS, P.O. Box 475, 106 St. John St. Merrickville, Ontario K0G1N0, CANADA) accessible under: http://www.agbios.com/dbase.php.

| | Event | Company | Description | Crop | Patent Ref |
|---|---|---|---|---|---|
| | | | subsp. *kurstaki*, and the phosphinothricin N-acetyltransferase (PAT) encoding gene from *S. viridochromogenes*. Corn rootworm-resistance is derived from MIR604 which contains the mcry3A gene from *Bacillus thuringiensis*. Tolerance to glyphosate herbcicide is derived from GA21 which contains a a modified EPSPS gene from maize. | | |
| A-150 | CBH-351 | Aventis Crop Science | Insect-resistant and glufosinate ammonium herbicide tolerant maize developed by inserting genes encoding Cry9C protein from *Bacillus thuringiensis* subsp *tolworthi* and phosphinothricin acetyltransferase (PAT) from *Streptomyces hygroscopicus*. | *Zea mays* L. (Maize) | |
| A-151 | DAS-06275-8 | DOW AgroSciences LLC | Lepidopteran insect resistant and glufosinate ammonium herbicide-tolerant maize variety produced by inserting the cry1F gene from *Bacillus thuringiensis* var *aizawai* and the phosphinothricin acetyltransferase (PAT) from *Streptomyces hygroscopicus*. | *Zea mays* L. (Maize) | |
| A-152 | DAS-59122-7 | DOW AgroSciences LLC and Pioneer Hi-Bred International Inc. | Corn rootworm-resistant maize produced by inserting the cry34Ab1 and cry35Ab1 genes from *Bacillus thuringiensis* strain PS149B1. The PAT encoding gene from *Streptomyces viridochromogenes* was introduced as a selectable marker | *Zea mays* L. (Maize) | US 2006-070139, US 2011030086 |
| A-153 | DAS-59122-7 × NK603 | DOW AgroSciences LLC and Pioneer Hi-Bred International Inc. | Stacked insect resistant and herbicide tolerant maize produced by conventional cross breeding of parental lines DAS-59122-7 (OECD unique identifier: DAS-59122-7) with NK603 (OECD unique identifier: MON-ØØ6Ø3-6). Corn rootworm-resistance is derived from DAS-59122-7 which contains the cry34Ab1 and cry35Ab1 genes from *Bacillus thuringiensis* strain PS149B1. Tolerance to glyphosate herbcicide is derived from NK603. | *Zea mays* L. (Maize) | |
| A-154 | DAS-59122-7 × TC1507 × NK603 | DOW AgroSciences LLC and Pioneer Hi-Bred International Inc. | Stacked insect resistant and herbicide tolerant maize produced by conventional cross breeding of parental lines DAS-59122-7 (OECD unique identifier: DAS-59122-7) and TC1507 (OECD unique identifier: DAS-Ø15Ø7-1) with NK603 (OECD unique identifier: MON-ØØ6Ø3-6). Corn rootworm-resistance is derived from DAS-59122-7 which contains the cry34Ab1 | *Zea mays* L. (Maize) | |

TABLE A-continued

Non-exclusive list of transgenic plants and events for the design of experiments with the compound of formula (I) related to the invention (source: (AGBIOS, P.O. Box 475, 106 St. John St. Merrickville, Ontario K0G1N0, CANADA) accessible under: http://www.agbios.com/dbase.php.

| | Event | Company | Description | Crop | Patent Ref |
|---|---|---|---|---|---|
| A-155 | DAS-Ø15Ø7-1 × MON-ØØ6Ø3-6 | DOW AgroSciences LLC | and cry35Ab1 genes from *Bacillus thuringiensis* strain PS149B1. Lepidopteran resistance and toleraance to glufosinate ammonium herbicide is derived from TC1507. Tolerance to glyphosate herbcicide is derived from NK603. Stacked insect resistant and herbicide tolerant corn hybrid derived from conventional cross-breeding of the parental lines 1507 (OECD identifier: DAS-Ø15Ø7-1) and NK603 (OECD identifier: MON-ØØ6Ø3-6). | *Zea mays* L. (Maize) | |
| A-156 | DBT418 | Dekalb Genetics Corporation | Insect-resistant and glufosinate ammonium herbicide tolerant maize developed by inserting genes encoding Cry1AC protein from *Bacillus thuringiensis* subsp *kurstaki* and phosphinothricin acetyltransferase (PAT) from *Streptomyces hygroscopicus* | *Zea mays* L. (Maize) | |
| A-157 | DK404SR | BASF Inc. | Somaclonal variants with a modified acetyl-CoA-carboxylase (ACCase) were selected by culture of embryos on sethoxydim enriched medium. | *Zea mays* L. (Maize) | |
| A-158 | DP-098140-6 | PIONEER HI-BRED INTERNATIONAL | Glyphosate tolerance/ALS inhibitor tolerance | *Zea mays* L. (Maize) | WO 2008/112019, US2010240059 |
| A-159 | DP-Ø9814Ø-6 (Event 98140) | Pioneer Hi-Bred International Inc. | Corn line 98140 was genetically engineered to express the GAT4621 (glyphosate acetyltransferase) and ZM-HRA (modified version of a maize acetolactate synthase) proteins. The GAT4621 protein, encoded by the gat4621 gene, confers tolerance to glyphosate-containing herbicides by acetylating glyphosate and thereby rendering it non-phytotoxic. The ZM-HRA protein, encoded by the zm-hra gene, confers tolerance to the ALS-inhibiting class of herbicides. | *Zea mays* L. (Maize) | |
| A-160 | Event 3272 | Syngenta Seeds, Inc. | Maize line expressing a heat stable alpha-amylase gene amy797E for use in the dry-grind ethanol process. The phosphomannose isomerase gene from *E. coli* was used as a selectable marker. | *Zea mays* L. (Maize) | |
| A-161 | Event 98140 | Pioneer Hi-Bred International Inc. | Maize event expressing tolerance to glyphosate herbicide, via expression of a modified bacterial glyphosate N-acetyltransferase, and ALS-inhibiting herbicides, vial expression of a modified form of the maize acetolactate synthase enzyme. | *Zea mays* L. (Maize) | |

TABLE A-continued

Non-exclusive list of transgenic plants and events for the design of experiments with the compound of formula (I) related to the invention (source: (AGBIOS, P.O. Box 475, 106 St. John St. Merrickville, Ontario K0G1N0, CANADA) accessible under: http://www.agbios.com/dbase.php.

|  | Event | Company | Description | Crop | Patent Ref |
|---|---|---|---|---|---|
| A-162 | EXP1910 IT | Syngenta Seeds, Inc. (formerly Zeneca Seeds) | Tolerance to the imidazolinone herbicide, imazethapyr, induced by chemical mutagenesis of the acetolactate synthase (ALS) enzyme using ethyl methanesulfonate (EMS). | Zea mays L. (Maize) |  |
| A-163 | FI117 | DEKALB GENETICS CORP | Glyphosate resistance | Zea mays L. (Maize) | U.S. Pat. No. 6,040,497 |
| A-164 | GA21 | Monsanto Company | Introduction, by particle bombardment, of a modified 5-enolpyruvyl shikimate-3-phosphate synthase (EPSPS), an enzyme involved in the shikimate biochemical pathway for the production of the aromatic amino acids | Zea mays L. (Maize) | U.S. Pat. No. 6,040,497 |
| A-165 | GA21 × MON810 | Monsanto Company | Stacked insect resistant and herbicide tolerant corn hybrid derived from conventional cross-breeding of the parental lines GA21 (OECD identifider: MON-ØØØ21-9) and MON810 (OECD identifier: MON-ØØ810-6). | Zea mays L. (Maize) |  |
| A-166 | GAT-ZM1 | BAYER CROPSCIENCE N.V. | Glufosinate tolerance | Zea mays L. (Maize) | WO 01/51654 |
| A-167 | GG25 | DEKALB GENETICS CORP | Glyphosate resistance | Zea mays L. (Maize) | U.S. Pat. No. 6,040,497 |
| A-168 | GJ11 | DEKALB GENETICS CORP | Glyphosate resistance | Zea mays L. (Maize) | U.S. Pat. No. 6,040,497 |
| A-169 | IT | Pioneer Hi-Bred International Inc. | Tolerance to the imidazolinone herbicide, imazethapyr, was obtained by in vitro selection of somaclonal variants. | Zea mays L. (Maize) |  |
| A-170 | LY038 | Monsanto Company | Altered amino acid composition, specifically elevated levels of lysine, through the introduction of the cordapA gene, derived from Corynebacterium glutamicum, encoding the enzyme dihydrodipicolinate synthase (cDHDPS) | Zea mays L. (Maize) | U.S. Pat. No. 7,157,281, US2010212051, US 2007028322 |
| A-171 | MIR162 | SYNGENTA PARTICIPA-TIONS AG | Insect resistance | Zea mays L. (Maize) | WO 2007142840 |
| A-172 | MIR604 | Syngenta Seeds, Inc. | Corn rootworm resistant maize produced by transformation with a modified cry3A gene. The phosphomannose isomerase gene from E. coli was used as a selectable marker; (Cry3a055) | Zea mays L. (Maize) | EP 1 737 290 |
| A-173 | MIR604 × GA21 | Syngenta Seeds, Inc. | Stacked insect resistant and herbicide tolerant maize produced by conventional cross breeding of parental lines MIR604 (OECD unique identifier: SYN-IR6Ø5-5) and GA21 (OECD unique identifier: MON-ØØØ21-9). Corn rootworm-resistance is derived from MIR604 which contains the mcry3A gene from Bacillus thuringiensis. Tolerance to glyphosate | Zea mays L. (Maize) |  |

TABLE A-continued

Non-exclusive list of transgenic plants and events for the design of experiments with the compound of formula (I) related to the invention (source: (AGBIOS, P.O. Box 475, 106 St. John St. Merrickville, Ontario K0G1N0, CANADA) accessible under: http://www.agbios.com/dbase.php.

| | Event | Company | Description | Crop | Patent Ref |
|---|---|---|---|---|---|
| A-174 | MON80100 | Monsanto Company | herbcicide is derived from GA21. Insect-resistant maize produced by inserting the cry1Ab gene from *Bacillus thuringiensis* subsp. *kurstaki*. The genetic modification affords resistance to attack by the European corn borer (ECB). | *Zea mays* L. (Maize) | |
| A-175 | MON802 | Monsanto Company | Insect-resistant and glyphosate herbicide tolerant maize produced by inserting the genes encoding the Cry1Ab protein from *Bacillus thuringiensis* and the 5-enolpyruvylshikimate-3-phosphate synthase (EPSPS) from *A. tumefaciens* strain CP4. | *Zea mays* L. (Maize) | |
| A-176 | MON809 | Pioneer Hi-Bred International Inc. | Resistance to European corn borer (*Ostrinia nubilalis*) by introduction of a synthetic cry1Ab gene. Glyphosate resistance via introduction of the bacterial version of a plant enzyme, 5-enolpyruvyl shikimate-3-phosphate synthase (EPSPS). | *Zea mays* L. (Maize) | |
| A-177 | MON810 | Monsanto Company | Insect-resistant maize produced by inserting a truncated form of the cry1Ab gene from *Bacillus thuringiensis* subsp. *kurstaki* HD-1. The genetic modification affords resistance to attack by the European corn borer (ECB) | *Zea mays* L. (Maize) | US 2004-180373 |
| A-178 | MON810 × MON88017 | Monsanto Company | Stacked insect resistant and glyphosate tolerant maize derived from conventional cross-breeding of the parental lines MON810 (OECD identifier: MON-00810-6) and MON88017 (OECD identifier: MON-88017-3). European corn borer (ECB) resistance is derived from a truncated form of the cry1Ab gene from *Bacillus thuringiensis* subsp. *kurstaki* HD-1 present in MON810. Corn rootworm resistance is derived from the cry3Bb1 gene from *Bacillus thuringiensis* subspecies *kumamotoensis* strain EG4691 present in MON88017. Glyphosate tolerance is derived from a 5-enolpyruvylshikimate-3-phosphate synthase (EPSPS) encoding gene from *Agrobacterium tumefaciens* strain CP4 present in MON88017. | *Zea mays* L. (Maize) | |
| A-179 | MON832 | Monsanto Company | Introduction, by particle bombardment, of glyphosate oxidase (GOX) and a modified 5-enolpyruvyl shikimate-3-phosphate synthase (EPSPS), an enzyme involved in the shikimate biochemical pathway for the | *Zea mays* L. (Maize) | |

TABLE A-continued

Non-exclusive list of transgenic plants and events for the design of experiments with the compound of formula (I) related to the invention (source: (AGBIOS, P.O. Box 475, 106 St. John St. Merrickville, Ontario K0G1N0, CANADA) accessible under: http://www.agbios.com/dbase.php.

|  | Event | Company | Description | Crop | Patent Ref |
|---|---|---|---|---|---|
| A-180 | MON863 | Monsanto Company | production of the aromatic amino acids. Corn root worm resistant maize produced by inserting the cry3Bb1 gene from *Bacillus thuringiensis* subsp. *kumamotoensis*. | *Zea mays* L. (Maize) | |
| A-181 | MON863 × MON810 | Monsanto Company | Stacked insect resistant corn hybrid derived from conventional cross-breeding of the parental lines MON863 (OECD identifier: MON-ØØ863-5) and MON810 (OECD identifier: MON-ØØ81Ø-6) | *Zea mays* L. (Maize) | |
| A-182 | MON863 × MON810 × NK603 | Monsanto Company | Stacked insect resistant and herbicide tolerant corn hybrid derived from conventional cross-breeding of the stacked hybrid MON-ØØ863-5 × MON-ØØ81Ø-6 and NK603 (OECD identifier: MON-ØØ6Ø3-6). | *Zea mays* L. (Maize) | |
| A-183 | MON863 × NK603 | Monsanto Company | Stacked insect resistant and herbicide tolerant corn hybrid derived from conventional cross-breeding of the parental lines MON863 (OECD identifier: MON-ØØ863-5) and NK603 (OECD identifier: MON-ØØ6Ø3-6). | *Zea mays* L. (Maize) | |
| A-184 | MON87460 | Monsanto Company | Drought tolerance; Water deficit tolerance | *Zea mays* L. (Maize) | WO 2009111263 |
| A-185 | MON88017 | Monsanto Company | Corn rootworm-resistant maize produced by inserting the cry3Bb1 gene from *Bacillus thuringiensis* subspecies *kumamotoensis* strain EG4691. Glyphosate tolerance derived by inserting a 5-enolpyruvylshikimate-3-phosphate synthase (EPSPS) encoding gene from *Agrobacterium tumefaciens* strain CP4 | *Zea mays* L. (Maize) | WO2005059103 |
| A-186 | MON89034 | Monsanto Company | Maize event expressing two different insecticidal proteins from *Bacillus thuringiensis* providing resistance to number of lepidopteran pests; nsect resistance (Lepidoptera-Cry1A.105- Cry2Ab) | *Zea mays* L. (Maize) | WO 2007140256 |
| A-187 | MON89034 × MON88017 | Monsanto Company | Stacked insect resistant and glyphosate tolerant maize derived from conventional cross-breeding of the parental lines MON89034 (OECD identifier: MON-89Ø34-3) and MON88017 (OECD identifier: MON-88Ø17-3). Resistance to Lepiopteran insects is derived from two crygenes present in MON89043. Corn rootworm resistance is derived from a single cry genes and glyphosate tolerance is derived from the 5-enolpyruvylshikimate-3-phosphate synthase (EPSPS) encoding gene from *Agrobacterium tumefaciens* present in MON88017. | *Zea mays* L. (Maize) | |

TABLE A-continued

Non-exclusive list of transgenic plants and events for the design of experiments with the compound of formula (I) related to the invention (source: (AGBIOS, P.O. Box 475, 106 St. John St. Merrickville, Ontario K0G1N0, CANADA) accessible under: http://www.agbios.com/dbase.php.

|  | Event | Company | Description | Crop | Patent Ref |
|---|---|---|---|---|---|
| A-188 | MON89034 × NK603 | Monsanto Company | Stacked insect resistant and herbicide tolerant maize produced by conventional cross breeding of parental lines MON89034 (OECD identifier: MON-89Ø34-3) with NK603 (OECD unique identifier: MON-ØØ6Ø3-6). Resistance to Lepiopteran insects is derived from two crygenes present in MON89043. Tolerance to glyphosate herbcicide is derived from NK603. | Zea mays L. (Maize) | |
| A-189 | MON89034 × TC1507 × MON88017 × DAS-59122-7 | Monsanto Company | Stacked insect resistant and herbicide tolerant maize produced by conventional cross breeding of parental lines: MON89034, TC1507, MON88017, and DAS-59122. Resistance to the above-ground and below-ground insect pests and tolerance to glyphosate and glufosinate-ammonium containing herbicides. | Zea mays L. (Maize) | |
| A-190 | MON-ØØ6Ø3-6 × MON-ØØ81Ø-6 | Monsanto Company | Stacked insect resistant and herbicide tolerant corn hybrid derived from conventional cross-breeding of the parental lines NK603 (OECD identifier: MON-ØØ6Ø3-6) and MON810 (OECD identifier: MON-ØØ81Ø-6). | Zea mays L. (Maize) | |
| A-191 | MON-ØØ81Ø-6 × LY038 | Monsanto Company | Stacked insect resistant and enhanced lysine content maize derived from conventional cross-breeding of the parental lines MON810 (OECD identifier: MON-ØØ81Ø-6) and LY038 (OECD identifier: REN-ØØØ38-3). | Zea mays L. (Maize) | |
| A-192 | MON-ØØ863-5 × MON-ØØ6Ø3-6 | Monsanto Company | Stacked insect resistant and herbicide tolerant corn hybrid derived from conventional cross-breeding of the parental lines MON863 (OECD identifier: MON-ØØ863-5) and NK603 (OECD identifier: MON-ØØ6Ø3-6). | Zea mays L. (Maize) | |
| A-193 | MON-ØØ863-5 × MON-ØØ81Ø-6 | Monsanto Company | Stacked insect resistant corn hybrid derived from conventional cross-breeding of the parental lines MON863 (OECD identifier: MON-ØØ863-5) and MON810 (OECD identifier: MON-ØØ81Ø-6) | Zea mays L. (Maize) | |
| A-194 | MON-ØØ863-5 × MON-ØØ81Ø-6 × MON-ØØ6Ø3-6 | Monsanto Company | Stacked insect resistant and herbicide tolerant corn hybrid derived from conventional cross-breeding of the stacked hybrid MON-ØØ863-5 × MON-ØØ81Ø-6 and NK603 (OECD identifier: MON-ØØ6Ø3-6). | Zea mays L. (Maize) | |
| A-195 | MON-ØØØ21-9 × MON-ØØ81Ø-6 | Monsanto Company | Stacked insect resistant and herbicide tolerant corn hybrid derived from conventional cross-breeding of the parental lines GA21 (OECD identifider: MON-ØØØ21-9) | Zea mays L. (Maize) | |

TABLE A-continued

Non-exclusive list of transgenic plants and events for the design of experiments with the compound of formula (I) related to the invention (source: (AGBIOS, P.O. Box 475, 106 St. John St. Merrickville, Ontario K0G1N0, CANADA) accessible under: http://www.agbios.com/dbase.php.

|   | Event | Company | Description | Crop | Patent Ref |
|---|---|---|---|---|---|
| A-196 | MS3 | Bayer CropScience (Aventis CropScience(AgrEvo)) | and MON810 (OECD identifier: MON-ØØ81Ø-6). Male sterility caused by expression of the barnase ribonuclease gene from *Bacillus amyloliquefaciens*; PPT resistance was via PPT-acetyltransferase (PAT). | Zea mays L. (Maize) | |
| A-197 | MS6 | Bayer CropScience (Aventis CropScience(AgrEvo)) | Male sterility caused by expression of the barnase ribonuclease gene from *Bacillus amyloliquefaciens*; PPT resistance was via PPT-acetyltransferase (PAT). | Zea mays L. (Maize) | |
| A-198 | NK603 | Monsanto Company | Introduction, by particle bombardment, of a modified 5-enolpyruvyl shikimate-3-phosphate synthase (EPSPS), an enzyme involved in the shikimate biochemical pathway for the production of the aromatic amino acids. | Zea mays L. (Maize) | |
| A-199 | NK603 × MON810 | Monsanto Company | Stacked insect resistant and herbicide tolerant corn hybrid derived from conventional cross-breeding of the parental lines NK603 (OECD identifier: MON-ØØ6Ø3-6) and MON810 (OECD identifier: MON-ØØ81Ø-6). | Zea mays L. (Maize) | |
| A-200 | NK603 × T25 | Monsanto Company | Stacked glufosinate ammonium and glyphosate herbicide tolerant maize hybrid derived from conventional cross-breeding of the parental lines NK603 (OECD identifier: MON-ØØ6Ø3-6) and T25 (OECD identifier: ACS-ZM003-2). | Zea mays L. (Maize) | |
| A-201 | PV-ZMGT32 (NK603) | MONSANTO TECHNOLOGY LLC | Glyphosate tolerance | Zea mays L. (Maize) | US 2007-056056 |
| A-202 | PV-ZMGT32 (nk603) | MONSANTO TECHNOLOGY LLC | Glyphosate tolerance | Zea mays L. (Maize) | US 2007292854 |
| A-203 | PV-ZMIR13 (MON863) | MONSANTO TECHNOLOGY LLC | Insect resistance (Cry3Bb) | Zea mays L. (Maize) | US 2006-095986 |
| A-204 | SYN-BTØ11-1 × MON-ØØØ21-9 | Syngenta Seeds, Inc. | Stacked insect resistant and herbicide tolerant maize produced by conventional cross breeding of parental lines BT11 (OECD unique identifier: SYN-BTØ11-1) and GA21 (OECD unique identifier: MON-ØØØ21-9). | Zea mays L. (Maize) | |
| A-205 | T14 | Bayer CropScience (Aventis CropScience(AgrEvo)) | Glufosinate herbicide tolerant maize produced by inserting the phosphinothricin N-acetyltransferase (PAT) encoding gene from the aerobic actinomycete *Streptomyces viridochromogenes*. | Zea mays L. (Maize) | |
| A-206 | T14, T25 | Bayer CropScience (Aventis CropScience(AgrEvo)) | Glufosinate herbicide tolerant maize produced by inserting the phosphinothricin N-acetyltransferase (PAT) encoding gene from the aerobic actinomycete *Streptomyces viridochromogenes*. | Zea mays L. (Maize) | |

TABLE A-continued

Non-exclusive list of transgenic plants and events for the design of experiments with the compound of formula (I) related to the invention (source: (AGBIOS, P.O. Box 475, 106 St. John St. Merrickville, Ontario K0G1N0, CANADA) accessible under: http://www.agbios.com/dbase.php.

| | Event | Company | Description | Crop | Patent Ref |
|---|---|---|---|---|---|
| A-207 | T25 × MON810 | Bayer CropScience (Aventis CropScience(AgrEvo)) | Stacked insect resistant and herbicide tolerant corn hybrid derived from conventional cross-breeding of the parental lines T25 (OECD identifier: ACS-ZMØØ3-2) and MON810 (OECD identifier: MON-ØØ81Ø-6). | Zea mays L. (Maize) | |
| A-208 | TC1507 | Mycogen (c/o Dow AgroSciences); Pioneer (c/o Dupont) | Insect-resistant and glufosinate ammonium herbicide tolerant maize produced by inserting the cry1F gene from Bacillus thuringiensis var. aizawai and the phosphinothricin N-acetyltransferase encoding gene from Streptomyces viridochromogenes; Insect resistance (Cry1F) | Zea mays L. (Maize) | U.S. Pat. No. 7,435,807 |
| A-209 | TC1507 × DAS-59122-7 | DOW AgroSciences LLC and Pioneer Hi-Bred International Inc. | Stacked insect resistant and herbicide tolerant maize produced by conventional cross breeding of parental lines TC1507 (OECD unique identifier: DAS-Ø15Ø7-1) with DAS-59122-7 (OECD unique identifier: DAS-59122-7). Resistance to lepidopteran insects is derived from TC1507 due the presence of the cry1F gene from Bacillus thuringiensis var. aizawai. Corn rootworm-resistance is derived from DAS-59122-7 which contains the cry34Ab1 and cry35Ab1 genes from Bacillus thuringiensis strain PS149B1. Tolerance to glufosinate ammonium herbcicide is derived from TC1507 from the phosphinothricin N-acetyltransferase encoding gene from Streptomyces viridochromogenes. | Zea mays L. (Maize) | |
| A-210 | VIP1034 | SYNGENTA PARTICIPATIONS AG | Insect resistance | Zea mays L. (Maize) | WO 03/052073 |
| A-211 | E6611.32.1.38/ DP-32138-1/ 32138 | Pioneer Hi-Bred International Inc. | 1) MS45: anther-specific 5126 (Zea mays) promoter > fertility restoration Ms45 (Zea mays) coding sequence > fertility restoration Ms45 (Zea mays) 3'-untranslated region 2) ZM-AA1: polygalacturonase 47 (Zea mays) promoter > brittle-1 (Zea mays) chloroplast transit peptide > alpha-amylase-1 (Zea mays) truncated coding sequence > >In2-1 (Zea mays) 3'-untranslated region 3) DSRED2: 35S (Cauliflower Mosaic Virus) enhancer > lipid transfer protein-2 (Hordeum vulgare) promoter > red fluorescent protein (Dicosoma sp.) variant coding sequence > protein inhibitor II (Solanum tuberosum) 3'-untranslated region | zea mays L. (Maize) | WO 2009103049, MX 2010008977 |

TABLE A-continued

Non-exclusive list of transgenic plants and events for the design of experiments with the compound of formula (I) related to the invention (source: (AGBIOS, P.O. Box 475, 106 St. John St. Merrickville, Ontario K0G1N0, CANADA) accessible under: http://www.agbios.com/dbase.php.

| | Event | Company | Description | Crop | Patent Ref |
|---|---|---|---|---|---|
| A-212 | DAS-40278-9 | DOW AgroSciences LLC | RB7 MARv3>zmUbiquitin 1 promoter>aad1>zmPER5 3'UTR>RB 7 MARv4. The aad-1 gene confers tolerance to 2,4- dichlorophenoxyacetic acid and aryloxyphenoxypropionate (commonly referred to as "fop" herbicides such as quizalofop) herbicides | Zea mays L. (Maize) | WO 2011022469 |
| A-213 | MIR604 | Syngenta Participations AG | 1) CRY3A: metallotionin-like gene (Zea mays) promoter > delta-endotoxin cry3a (Bacillus thuringiensis subsp. tenebrionis) coding sequence, modified to include a cathepsin-G protease recognition site and maize codon optimized > nopaline synthase (Agrobacterium tumefaciens) 3'-untranslated region 2) PMI: polyubiquitin (Zea mays) promoter (incl. first intron) > mannose-6-phosphate isomerase (Escherichia coli) coding sequence > nopaline synthase (Agrobacterium tumefaciens) 3'-untranslated region | Zea mays L. (Maize) | US 2005216970, US 2008167456, US 2011111420 |
| A-214 | MON87427 | MONSANTO TECHNOLOGY LLC | The transgene insert and expression cassette of MON87427 comprises the promoter and leader from the cauliflower mosaic virus (CaMV) 35 S containing a duplicated enhancer region (P-e35S); operably linked to a DNA leader derived from the first intron from the maize heat shock protein 70 gene (I-HSP70); operably linked to a DNA molecule encoding an N-terminal chloroplast transit peptide from the shkG gene from Arabidopsis thaliana EPSPS (Ts-CTP2); operably linked to a DNA molecule derived from the aroA gene from the Agrobacterium sp. strain CP4 and encoding the CP4 EPSPS protein; operably linked to a 3' UTR DNA molecule derived from the nopaline synthase (T-NOS) gene from Agrobacterium tumefaciens. | Zea mays L. (Maize) | WO 2011062904 |
| A-215 | DP-004114-3 | Pioneer Hi-Bred International Inc. | cry1F, cry34Ab1, cry35Ab1, and pat: resistance to certain lepidopteran and coleopteran pests, as well as tolerance to phosphinothricin. | Zea mays L. (Maize) | US 2011154523 |
| A-216 | DP-032316-8 | Pioneer Hi-Bred International Inc. | Cry1F, cry34Ab1, cry35Ab1, pat: resistance to certain lepidopteran and coleopteran pests, as well as tolerance to phosphinothricin | Zea mays L. (Maize) | US 2011154524 |
| A-217 | DP-040416-8a | Pioneer Hi-Bred International Inc. | Cry1F, cry34Ab1, cry35Ab1, pat: resistance to certain lepidopteran and coleopteran pests, as well as tolerance to phosphinothricin | Zea mays L. (Maize) | US 20110154525 |

TABLE A-continued

Non-exclusive list of transgenic plants and events for the design of experiments with the compound of formula (I) related to the invention (source: (AGBIOS, P.O. Box 475, 106 St. John St. Merrickville, Ontario K0G1N0, CANADA) accessible under: http://www.agbios.com/dbase.php.

| Event | | Company | Description | Crop | Patent Ref |
|---|---|---|---|---|---|
| A-218 | DP-043A47-3 | Pioneer Hi-Bred International Inc. | Cry1F, cry34Ab1, cry35Ab1, pat: resistance to certain lepidopteran and coleopteran pests, as well as tolerance to phosphinothricin | *Zea mays* L. (Maize) | US20110154526 |

Particularly useful transgenic plants which may be treated according to the invention are plants containing transformation events, or a combination of transformation events, and that are listed for example in the databases for various national or regional regulatory agencies including Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US2002120964 or WO2002/034946); Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control—herbicide tolerance, deposited as PTA-6233, described in WO2005/103266 or US2005216969); Event 3006-210-23 (cotton, insect control—herbicide tolerance, deposited as PTA-6233, described in US2007143876 or WO2005/103266); Event 3272 (corn, quality trait, deposited as PTA-9972, described in WO2006098952 or US2006230473); Event 40416 (corn, insect control—herbicide tolerance, deposited as ATCC PTA-11508, described in WO2011/075593); Event 43A47 (corn, insect control—herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US2006162007 or WO2004053062); Event B16 (corn, herbicide tolerance, not deposited, described in US2003126634); Event BPS-CV127-9 (soybean, herbicide tolerance, deposited as NCIMB No. 41603, described in WO2010/080829); Event CE43-67B (cotton, insect control, deposited as DSM ACC2724, described in US2009217423 or WO2006/128573); Event CE44-69D (cotton, insect control, not deposited, described in US20100024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US2006130175 or WO2004039986); Event COT202 (cotton, insect control, not deposited, described in US2007067868 or WO2005054479); Event COT203 (cotton, insect control, not deposited, described in WO2005/054480); Event DAS40278 (corn, herbicide tolerance, deposited as ATCC PTA-10244, described in WO2011/022469); Event DAS-59122-7 (corn, insect control—herbicide tolerance, deposited as ATCC PTA 11384, described in US2006070139); Event DAS-59132 (corn, insect control—herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US2009137395 or WO2008/112019); Event DP-305423-1 (soybean, quality trait, not deposited, described in US2008312082 or WO2008/054747); Event DP-32138-1 (corn, hybridization system, deposited as ATCC PTA-9158, described in US20090210970 or WO2009/103049); Event DP-356043-5 (soybean, herbicide tolerance, deposited as ATCC PTA-8287, described in US20100184079 or WO2008/002872); Event EE-1 (brinjal, insect control, not deposited, described in WO2007/091277); Event FI117 (corn, herbicide tolerance, deposited as ATCC 209031, described in US2006059581 or WO1998/044140); Event GA21 (corn, herbicide tolerance, deposited as ATCC 209033, described in US2005086719 or WO1998/044140); Event GG25 (corn, herbicide tolerance, deposited as ATCC 209032, described in US2005188434 or WO1998/044140); Event GHB119 (cotton, insect control—herbicide tolerance, deposited as ATCC PTA-8398, described in WO2008/151780); Event GHB614 (cotton, herbicide tolerance, deposited as ATCC PTA-6878, described in US2010050282 or WO2007/017186); Event GJ11 (corn, herbicide tolerance, deposited as ATCC 209030, described in US2005188434 or WO1998/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US2004172669 or WO2004/074492); Event JOPLIN1 (wheat, disease tolerance, not deposited, described in US2008064032); Event LL27 (soybean, herbicide tolerance, deposited as NCIMB41658, described in WO2006/108674 or US2008320616); Event LL55 (soybean, herbicide tolerance, deposited as NCIMB 41660, described in WO2006/108675 or US2008196127); Event LLcotton25 (cotton, herbicide tolerance, deposited as ATCC PTA-3343, described in WO2003013224 or US2003097687); Event LLRICE06 (rice, herbicide tolerance, deposited as ATCC-23352, described in U.S. Pat. No. 6,468,747 or WO2000/026345); Event LLRICE601 (rice, herbicide tolerance, deposited as ATCC PTA-2600, described in US20082289060 or WO2000/026356); Event LY038 (corn, quality trait, deposited as ATCC PTA-5623, described in US2007028322 or WO2005061720); Event MIR162 (corn, insect control, deposited as PTA-8166, described in US2009300784 or WO2007/142840); Event MIR604 (corn, insect control, not deposited, described in US2008167456 or WO2005103301); Event MON15985 (cotton, insect control, deposited as ATCC PTA-2516, described in US2004-250317 or WO2002/100163); Event MON810 (corn, insect control, not deposited, described in US2002102582); Event MON863 (corn, insect control, deposited as ATCC PTA-2605, described in WO2004/011601 or US2006095986); Event MON87427 (corn, pollination control, deposited as ATCC PTA-7899, described in WO2011/062904); Event MON87460 (corn, stress tolerance, deposited as ATCC PTA-8910, described in WO2009/111263 or US20110138504); Event MON87701 (soybean, insect control, deposited as ATCC PTA-8194, described in US2009130071 or WO2009/064652); Event MON87705 (soybean, quality trait—herbicide tolerance, deposited as ATCC PTA-9241, described in US20100080887 or WO2010/037016); Event MON87708 (soybean, herbicide tolerance, deposited as ATCC PTA9670, described in WO2011/034704); Event MON87754 (soybean, quality trait, deposited as ATCC PTA-9385, described in WO2010/024976); Event MON87769 (soybean, quality trait, deposited as ATCC PTA-8911, described in US20110067141 or WO2009/102873); Event MON88017 (corn, insect control—herbicide tolerance, deposited as ATCC PTA-5582, described in US2008028482 or WO2005/059103); Event MON88913 (cotton, herbicide tolerance, deposited as ATCC PTA-4854, described in WO2004/072235 or US2006059590); Event MON89034 (corn, insect control, deposited as ATCC PTA-7455, described in WO2007/140256 or US2008260932); Event MON89788 (soybean, herbicide tolerance, deposited as ATCC PTA-6708, described in US2006282915 or WO2006/130436); Event MS11 (oilseed rape, pollination control—herbicide tolerance, deposited as ATCC PTA-850 or PTA-2485, described in WO2001/031042); Event MS8 (oilseed rape, pollination control—herbicide tolerance, deposited as ATCC PTA-730, described in WO2001/041558 or US2003188347); Event NK603 (corn, herbicide tolerance, deposited as ATCC PTA-2478, described in US2007-292854); Event PE-7 (rice, insect control, not deposited, described in WO2008/114282); Event RF3 (oilseed rape, pollination control—herbicide tolerance, deposited as ATCC PTA-730, described in WO2001/041558 or US2003188347); Event RT73 (oilseed rape, herbicide tolerance, not deposited, described in WO2002/036831 or US2008070260); Event T227-1 (sugar beet, herbicide tolerance, not deposited, described in WO2002/44407 or US2009265817); Event T25 (corn, herbicide tolerance, not deposited, described in US2001029014 or WO2001/051654); Event T304-40 (cotton, insect control—herbicide tolerance, deposited as ATCC PTA-8171, described in US2010077501 or WO2008/122406); Event T342-142 (cotton, insect control, not deposited, described in WO2006/128568); Event TC1507 (corn, insect control—herbicide tolerance, not deposited, described in US2005039226 or WO2004/099447); Event VIP1034 (corn, insect control—herbicide tolerance, deposited as ATCC PTA-3925, described in WO2003/052073), Event 32316 (corn, insect control-herbicide tolerance, deposited as PTA-11507, described in WO2011/084632), Event 4114 (corn, insect control-herbicide tolerance, deposited as PTA-11506, described in WO2011/084621).

Plants that may be treated according to the invention are hybrid plants that already express the characteristic of heterosis or hybrid vigor which results in generally higher yield, vigor, health and resistance towards biotic and abiotic stresses). Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species (WO 92/05251, WO 95/09910, WO 98/27806, WO 05/002324, WO 06/021972 and U.S. Pat. No. 6,229,072). However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar (e.g. WO 91/02069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-resistant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science 221, 370-371), the CP4 gene of the bacterium *Agrobacterium* sp. (Barry et al., 1992, Curr. Topics Plant Physiol. 7, 139-145), the genes encoding a Petunia EPSPS (Shah et al., 1986, Science 233, 478-481), a Tomato EPSPS (Gasser et al., 1988, J. Biol. Chem. 263, 4280-4289), or an *Eleusine* EPSPS (WO 01/66704). It can also be a mutated EPSPS as described in for example EP 0837944, WO 00/66746, WO 00/66747 or WO02/26995. Glyphosate-tolerant plants can also be obtained by expressing a gene that encodes a glyphosate oxido-reductase enzyme as described in U.S. Pat. Nos. 5,776,760 and 5,463,175. Glyphosate-tolerant plants can also be obtained by expressing a gene that encodes a glyphosate acetyl transferase enzyme as described in for example WO 02/36782, WO 03/092360, WO 05/012515 and WO 07/024,782. Glyphosate-tolerant plants can also be obtained by selecting plants containing naturally-occurring mutations of the above-mentioned genes, as described in for example WO 01/024615 or WO 03/013226. Plants expressing EPSPS genes that confer glyphosate tolerance are described in e.g. U.S. patent application Ser. Nos. 11/517,991, 10/739,610, 12/139,408, 12/352,532, 11/312,866, 11/315,678, 12/421,292, 11/400,598, 11/651,752, 11/681,285, 11/605,824, 12/468,205, 11/760,570, 11/762,526, 11/769,327, 11/769,255, 11/943,801 or 12/362,774. Plants comprising other genes that confer glyphosate tolerance, such as decarboxylase genes, are described in e.g. U.S. patent application Ser. Nos. 11/588,811, 11/185,342, 12/364,724, 11/185,560 or 12/423,926.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition, e.g. described in U.S. patent application Ser. No. 11/760,602. One such efficient detoxifying enzyme is an enzyme encoding a phosphinothricin acetyltransferase (such as the bar or pat protein from *Streptomyces* species). Plants expressing an exogenous phosphinothricin acetyltransferase are for example described in U.S. Pat. Nos. 5,561,236; 5,648,477; 5,646,024; 5,273,894; 5,637,489; 5,276,268; 5,739,082; 5,908,810 and 7,112,665.

Further herbicide-tolerant plants are also plants that are made tolerant to the herbicides inhibiting the enzyme hydroxyphenylpyruvatedioxygenase (HPPD). HPPD is an enzyme that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme as described in WO 96/38567, WO 99/24585, WO 99/24586, WO 2009/144079, WO 2002/046387, or U.S. Pat. No. 6,768,044. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate deshydrogenase (PDH) activity in addition to a gene encoding an HPPD-tolerant enzyme, as described in WO 2004/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Still further herbicide resistant plants are plants that are made tolerant to acetolactate synthase (ALS) inhibitors. Known ALS-inhibitors include, for example, sulfonylurea, imidazolinone, triazolopyrimidines, pryimidinyoxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright (2002, Weed Science 50:700-712), but also, in U.S. Pat. Nos. 5,605,011, 5,378,824, 5,141,870, and 5,013,659. The production of sulfonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270. Other imidazolinone-tolerant plants are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerant plants are also described in for example WO 07/024,782 and U.S. Patent Application No. 61/288,958.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084,082, for rice in WO 97/41218, for sugar beet in U.S. Pat. No. 5,773,702 and WO 99/057965, for lettuce in U.S. Pat. No. 5,198,599, or for sunflower in WO 01/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al. (1998, Microbiology and Molecular Biology Reviews, 62: 807-813), updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP 1999141 and WO 2007/107302), or such proteins encoded by synthetic genes as e.g. described in and U.S. patent application Ser. No. 12/249,016; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al. 2001, Nat. Biotechnol. 19: 668-72; Schnepf et al. 2006, Applied Environm. Microbiol. 71, 1765-1774) or the binary toxin made up of the Cry1A or Cry1F proteins and the Cry2Aa or Cry2Ab or Cry2Ae proteins (U.S. patent application Ser. No. 12/214,022 and EP 08010791.5); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON89034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102; or 9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. Patent Appl. Nos. 61/126,083 and 61/195,019), or the binary toxin made up of the VIP3 protein and the Cry2Aa or Cry2Ab or Cry2Ae proteins (U.S. patent application Ser. No. 12/214,022 and EP 08010791.5).

10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein)

Of course, an insect-resistant transgenic plant, as used herein, also includes any plant comprising a combination of genes encoding the proteins of any one of the above classes 1 to 10. In one embodiment, an insect-resistant plant contains more than one transgene encoding a protein of any one of the above classes 1 to 10, to expand the range of target insect species affected when using different proteins directed at different target insect species, or to delay insect resistance development to the plants by using different proteins insecticidal to the same target insect species but having a different mode of action, such as binding to different receptor binding sites in the insect.

An "insect-resistant transgenic plant", as used herein, further includes any plant containing at least one transgene comprising a sequence producing upon expression a double-stranded RNA which upon ingestion by a plant insect pest inhibits the growth of this insect pest, as described e.g. in WO 2007/080126, WO 2006/129204, WO 2007/074405, WO 2007/080127 and WO 2007/035650.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

1) plants which contain a transgene capable of reducing the expression and/or the activity of poly(ADP-ribose) polymerase (PARP) gene in the plant cells or plants as described in WO 00/04173, WO/2006/045633, EP 04077984.5, or EP 06009836.5.
2) plants which contain a stress tolerance enhancing transgene capable of reducing the expression and/or the activity of the PARG encoding genes of the plants or plants cells, as described e.g. in WO 2004/090140.
3) plants which contain a stress tolerance enhancing transgene coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase as described e.g. in EP 04077624.7, WO 2006/133827, PCT/EP07/002,433, EP 1999263, or WO 2007/107326.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications. Said transgenic plants synthesizing a modified starch are disclosed, for example, in EP 0571427, WO 95/04826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, EP 06090134.5, EP 06090228.5, EP 06090227.7, EP 07090007.1, EP 07090009.7, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 2005/002359, U.S. Pat. No. 5,824,790, U.S. Pat. No. 6,013,861, WO 94/04693, WO 94/09144, WO 94/11520, WO 95/35026, WO 97/20936, WO 10/012,796, WO 10/003,701

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, as disclosed in EP 0663956, WO 96/01904, WO 96/21023, WO 98/39460, and WO 99/24593, plants producing alpha-1,4-glucans as disclosed in WO 95/31553, US 2002031826, U.S. Pat. No. 6,284,479, U.S. Pat. No. 5,712,107, WO 97/47806, WO 97/47807, WO 97/47808 and WO 00/14249, plants producing alpha-1,6 branched alpha-1,4-glucans, as disclosed in WO 00/73422, plants producing alternan, as disclosed in e.g. WO 00/47727, WO 00/73422, EP 06077301.7, U.S. Pat. No. 5,908,975 and EP 0728213, 3) transgenic plants which produce hyaluronan, as for example disclosed in WO 2006/032538, WO 2007/039314, WO 2007/039315, WO 2007/039316, JP 2006304779, and WO 2005/012529.

4) transgenic plants or hybrid plants, such as onions with characteristics such as 'high soluble solids content', 'low pungency' (LP) and/or 'long storage' (LS), as described in U.S. patent application Ser. No. 12/020,360 and 61/054,026.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:

a) Plants, such as cotton plants, containing an altered form of cellulose synthase genes as described in WO 98/00549 b) Plants, such as cotton plants, containing an altered form of rsw2 or rsw3 homologous nucleic acids as described in WO 2004/053219
c) Plants, such as cotton plants, with increased expression of sucrose phosphate synthase as described in WO 01/17333
d) Plants, such as cotton plants, with increased expression of sucrose synthase as described in WO 02/45485
e) Plants, such as cotton plants, wherein the timing of the plasmodesmatal gating at the basis of the fiber cell is altered, e.g. through downregulation of fiber-selective β-1,3-glucanase as described in WO 2005/017157, or as described in EP 08075514.3 or U.S. Patent Appl. No. 61/128,938
f) Plants, such as cotton plants, having fibers with altered reactivity, e.g. through the expression of N-acetylglucosaminetransferase gene including nodC and chitin synthase genes as described in WO 2006/136351

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics and include:
a) Plants, such as oilseed rape plants, producing oil having a high oleic acid content as described e.g. in U.S. Pat. No. 5,969,169, U.S. Pat. No. 5,840,946 or U.S. Pat. No. 6,323,392 or U.S. Pat. No. 6,063,947
b) Plants such as oilseed rape plants, producing oil having a low linolenic acid content as described in U.S. Pat. No. 6,270,828, U.S. Pat. No. 6,169,190, or U.S. Pat. No. 5,965,755
c) Plant such as oilseed rape plants, producing oil having a low level of saturated fatty acids as described e.g. in U.S. Pat. No. 5,434,283 or U.S. patent application Ser. No. 12/668,303

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering as described in U.S. Patent Appl. No. 61/135,230, WO09/068,313 and WO10/006,732.

Plants or plant cultivars (that can be obtained by plant biotechnology methods such as genetic engineering) which may also be treated according to the invention are plants, such as Tobacco plants, with altered post-translational protein modification patterns, for example as described in WO 10/121,818 and WO 10/145,846.

Particularly useful transgenic plants which may be treated according to the invention are plants containing transformation events, or combination of transformation events, that are the subject of petitions for non-regulated status, in the United States of America, to the Animal and Plant Health Inspection Service (APHIS) of the United States Department of Agriculture (USDA) whether such petitions are granted or are still pending. At any time this information is readily available from APHIS (4700 River Road Riverdale, Md. 20737, USA), for instance on its internet site (URL http://www.aphis.usda.gov/brs/not_reg.html). On the filing date of this application the petitions for nonregulated status that were pending with APHIS or granted by APHIS were those listed in Table B which contains the following information:

Petition: the identification number of the petition. Technical descriptions of the transformation events can be found in the individual petition documents which are obtainable from APHIS, for example on the APHIS website, by reference to this petition number. These descriptions are herein incorporated by reference.

Extension of Petition: reference to a previous petition for which an extension is requested.

Institution: the name of the entity submitting the petition.

Regulated article: the plant species concerned.

Transgenic phenotype: the trait conferred to the plants by the transformation event.

Transformation event or line: the name of the event or events (sometimes also designated as lines or lines) for which nonregulated status is requested.

APHIS documents: various documents published by APHIS in relation to the Petition and which can be requested with APHIS.

TABLE B

Non-exhaustive lists of transgenic plants and events for the conduction of experiments according to the invention obtained from the APHIS- data base of the United States Department of Agriculture (USDA). The data base can be found under the following link: http://www.aphis.usda.gov/animal_welfare/efoia/index.shtml.

| No | Petition | Extension of Petition Number *** | Institution | Crop | Transgenic Phenotype | Transformation Event or Line |
|---|---|---|---|---|---|---|
| B-1 | 10-070-01p | | Virginia Tech | Peanut | Sclerotinia blight resistant | N70, P39, and W171 |
| B-2 | 09-349-01p | | Dow AgroSciences | Soybean | 2,4-D and glufosinate tolerant | DAS-68416-4 |
| B-3 | 09-328-01p | | Bayer Crop Science | Soybean | glyphosate and isoxaflutole tolerant | FG72 |
| B-4 | 09-233-01p | | Dow | Corn | 2,4-D and ACCase-inhibitor tolerant | DAS-40278-9 |
| B-5 | 09-201-01p | | Monsanto | Soybean | improved fatty acid profile | MON-87705-6 |
| B-6 | 09-183-01p | | Monsanto | Soybean | stearidonic acid produced | MON-87769 |
| B-7 | 09-082-01p | | Monsanto | Soybean | Lepidopteran resistant | MON 87701 |

TABLE B-continued

Non-exhaustive lists of transgenic plants and events for the conduction of experiments according to the invention obtained from the APHIS- data base of the United States Department of Agriculture (USDA). The data base can be found under the following link: http://www.aphis.usda.gov/animal_welfare/efoia/index.shtml.

| No | Petition | Extension of Petition Number *** | Institution | Crop | Transgenic Phenotype | Transformation Event or Line |
|---|---|---|---|---|---|---|
| B-8 | 09-063-01p | | Stine Seed | Corn | Glyphosate tolerant | HCEM485 |
| B-9 | 09-055-01p | | Monsanto | Corn | Drought Tolerant | MON 87460 |
| B-10 | 09-015-01p | | BASF Plant Science, LLC | Soybean | imidazolinone tolerant | BPS-CV127-9 Soybean |
| B-11 | 08-366-01p | | ArborGen | Eucalyptus | Freeze Tolerant, Fertility Altered | ARB-FTE1-08 |
| B-12 | 08-340-01p | | Bayer | Cotton | Glufosinate Tolerant, Insect Resistant | T304-40XGHB119 |
| B-13 | 08-338-01p | | Pioneer | Corn | Male Sterile, Fertility Restored, Visual Marker | DP-32138-1 |
| B-14 | 08-315-01p | | Florigene | Rose | Altered Flower Color | IFD-52401-4 and IFD-52901-9 |
| B-15 | 07-108-01p | | Syngenta | Cotton | Lepidopteran Resistant | COT67B |
| B-16 | 06-354-01p | | Pioneer | Soybean | High Oleic Acid | DP-305423-1 |
| B-17 | 05-280-01p | | Syngenta | Corn | Thermostable alpha-amylase | 3272 |
| B-18 | 04-110-01p | | Monsanto & Forage Genetics | Alfalfa | Glyphosate Tolerant | J101, J163 |
| B-19 | 03-104-01p | | Monsanto & Scotts | Creeping bentgrass | Glyphosate Tolerant | ASR368 |
| B-20 | 07-253-01p | | Syngenta | Corn | Lepidopteran resistant | MIR-162 Maize |
| B-21 | 07-152-01p | | Pioneer | Corn | glyphosate & Imidazolinone tolerant | DP-098140-6 |
| B-22 | 04-337-01p | | University of Florida | Papaya | Papaya Ringspot Virus Resistant | X17-2 |
| B-23 | 06-332-01p | | Bayer CropScience | Cotton | Glyphosate tolerant | GHB614 |
| B-24 | 06-298-01p | | Monsanto | Corn | European Corn Borer resistant | MON 89034 |
| B-25 | 06-271-01p | | Pioneer | Soybean | Glyphosate & acetolactate synthase tolerant | 356043 (DP-356043-5) |
| B-26 | 06-234-01p | 98-329-01p | Bayer CropScience | Rice | Phosphinothricin tolerant | LLRICE601 |
| B-27 | 06-178-01p | | Monsanto | Soybean | Glyphosate tolerant | MON 89788 |
| B-28 | 04-362-01p | | Syngenta | Corn | Corn Rootworm Protected | MIR604 |
| B-29 | 04-264-01p | | ARS | Plum | Plum Pox Virus Resistant | C5 |
| B-30 | 04-229-01p | | Monsanto | Corn | High Lysine | LY038 |
| B-31 | 04-125-01p | | Monsanto | Corn | Corn Rootworm Resistant | 88017 |
| B-32 | 04-086-01p | | Monsanto | Cotton | Glyphosate Tolerant | MON 88913 |
| B-33 | 03-353-01p | | Dow | Corn | Corn Rootworm Resistant | 59122 |
| B-34 | 03-323-01p | | Monsanto | Sugar Beet | Glyphosate Tolerant | H7-1 |
| B-35 | 03-181-01p | 00-136-01p | Dow | Corn | Lepidopteran Resistant & Phosphinothricin tolerant | TC-6275 |
| B-36 | 03-155-01p | | Syngenta | Cotton | Lepidopteran Resistant | COT 102 |
| B-37 | 03-036-01p | | Mycogen/Dow | Cotton | Lepidopteran Resistant | 281-24-236 |
| B-38 | 03-036-02p | | Mycogen/Dow | Cotton | Lepidopteran Resistant | 3006-210-23 |
| B-39 | 02-042-01p | | Aventis | Cotton | Phosphinothericin tolerant | LLCotton25 |
| B-40 | 01-324-01p | 98-216-01p | Monsanto | Rapeseed | Glyphosate tolerant | RT200 |

TABLE B-continued

Non-exhaustive lists of transgenic plants and events for the conduction of experiments according to the invention obtained from the APHIS- data base of the United States Department of Agriculture (USDA). The data base can be found under the following link: http://www.aphis.usda.gov/animal_welfare/efoia/index.shtml.

| No | Petition | Extension of Petition Number *** | Institution | Crop | Transgenic Phenotype | Transformation Event or Line |
|---|---|---|---|---|---|---|
| B-41 | 01-206-01p | 98-278-01p | Aventis | Rapeseed | Phosphinothricin tolerant & pollination control | MS1 & RF1/RF2 |
| B-42 | 01-206-02p | 97-205-01p | Aventis | Rapeseed | Phosphinothricin tolerant | Topas 19/2 |
| B-43 | 01-137-01p | | Monsanto | Corn | Corn Rootworm Resistant | MON 863 |
| B-44 | 01-121-01p | | Vector | Tobacco | Reduced nicotine | Vector 21-41 |
| B-45 | 00-342-01p | | Monsanto | Cotton | Lepidopteran resistant | Cotton Event 15985 |
| B-46 | 00-136-01p | | Mycogen c/o Dow & Pioneer | Corn | Lepidopteran resistant tolerant | Line 1507 phosphinothricin |
| B-47 | 00-011-01p | 97-099-01p | Monsanto | Corn | Glyphosate tolerant | NK603 |
| B-48 | 99-173-01p | 97-204-01p | Monsanto | Potato | PLRV & CPB resistant | RBMT22-82 |
| B-49 | 98-349-01p | 95-228-01p | AgrEvo | Corn | Phosphinothricin tolerant and Male sterile | MS6 |
| B-50 | 98-335-01p | | U. of Saskatchewan | Flax | Tolerant to soil residues of sulfonyl urea herbicide | CDC Triffid |
| B-51 | 98-329-01p | | AgrEvo | Rice | Phosphinothricin tolerant | LLRICE06, LLRICE62 |
| B-52 | 98-278-01p | | AgrEvo | Rapeseed | Phosphinothricin tolerant & Pollination control | MS8 & RF3 |
| B-53 | 98-238-01p | | AgrEvo | Soybean | Phosphinothricin tolerant | GU262 |
| B-54 | 98-216-01p | | Monsanto | Rapeseed | Glyphosate tolerant | RT73 |
| B-55 | 98-173-01p | | Novartis Seeds & Monsanto | Beet | Glyphosate tolerant | GTSB77 |
| B-56 | 98-014-01p | 96-068-01p | AgrEvo | Soybean | Phosphinothricin tolerant | A5547-127 |
| B-57 | 97-342-01p | | Pioneer | Corn | Male sterile & Phosphinothricin tolerant | 676, 678, 680 |
| B-58 | 97-339-01p | | Monsanto | Potato | CPB & PVY resistant | RBMT15-101, SEMT15-02, SEMT15-15 |
| B-59 | 97-336-01p | | AgrEvo | Beet | Phosphinothricin tolerant | T-120-7 |
| B-60 | 97-287-01p | | Monsanto | Tomato | Lepidopteran resistant | 5345 |
| B-61 | 97-265-01p | | AgrEvo | Corn | Phosphinothricin tolerant & Lep. resistant | CBH-351 |
| B-62 | 97-205-01p | | AgrEvo | Rapeseed | Phosphinothricin tolerant | T45 |
| B-63 | 97-204-01p | | Monsanto | Potato | CPB & PLRV resistant | RBMT21-129 & RBMT21-350 |
| B-64 | 97-148-01p | | Bejo | Cichorium intybus | Male sterile | RM3-3, RM3-4, RM3-6 |
| B-65 | 97-099-01p | | Monsanto | Corn | Glyphosate tolerant | GA21 |
| B-66 | 97-013-01p | | Calgene | Cotton | Bromoxynil tolerant & Lepidopteran resistant | Events 31807 & 31808 |
| B-67 | 97-008-01p | | Du Pont | Soybean | Oil profile altered | G94-1, G94-19, G-168 |
| B-68 | 96-317-01p | | Monsanto | Corn | Glyphosate tolerant & ECB resistant | MON802 |
| B-69 | 96-291-01p | | DeKalb | Corn | European Corn Borer resistant | DBT418 |

TABLE B-continued

Non-exhaustive lists of transgenic plants and events for the conduction of experiments according to the invention obtained from the APHIS- data base of the United States Department of Agriculture (USDA). The data base can be found under the following link: http://www.aphis.usda.gov/animal_welfare/efoia/index.shtml.

| No | Petition | Extension of Petition Number *** | Institution | Crop | Transgenic Phenotype | Transformation Event or Line |
|---|---|---|---|---|---|---|
| B-70 | 96-248-01p | 92-196-01p | Calgene | Tomato | Fruit ripening altered | 1 additional FLAVRSAVR line |
| B-71 | 96-068-01p | | AgrEvo | Soybean | Phosphinothricin tolerant | W62, W98, A2704-12, A2704-21, A5547-35 |
| B-72 | 96-051-01p | | Cornell U | Papaya | PRSV resistant | 55-1, 63-1 |
| B-73 | 96-017-01p | 95-093-01p | Monsanto | Corn | European Corn Borer resistant | MON809 & MON810 |
| B-74 | 95-352-01p | | Asgrow | Squash | CMV, ZYMV, WMV2 resistant | CZW-3 |
| B-75 | 95-338-01p | | Monsanto | Potato | CPB resistant | SBT02-5 & −7, ATBT04-6 & −27, −30, −31, −36 |
| B-76 | 95-324-01p | | Agritope | Tomato | Fruit ripening altered | 35 1 N |
| B-77 | 95-256-01p | | Du Pont | Cotton | Sulfonylurea tolerant | 19-51a |
| B-78 | 95-228-01p | | Plant Genetic Systems | Corn | Male sterile | MS3 |
| B-79 | 95-195-01p | | Northrup King | Corn | European Corn Borer resistant | Bt11 |
| B-80 | 95-179-01p | 92-196-01p | Calgene | Tomato | Fruit ripening altered | 2 additional FLAVRSAVR lines |
| B-81 | 95-145-01p | | DeKalb | Corn | Phosphinothricin tolerant | B16 |
| B-82 | 95-093-01p | | Monsanto | Corn | Lepidopteran resistant | MON 80100 |
| B-83 | 95-053-01p | | Monsanto | Tomato | Fruit ripening altered | 8338 |
| B-84 | 95-045-01p | | Monsanto | Cotton | Glyphosate tolerant | 1445, 1698 |
| B-85 | 95-030-01p | 92-196-01p | Calgene | Tomato | Fruit ripening altered | 20 additional FLAVRSAVR lines |
| B-86 | 94-357-01p | | AgrEvo | Corn | Phosphinothricin tolerant | T14, T25 |
| B-87 | 94-319-01p | | Ciba Seeds | Corn | Lepidopteran resistant | Event 176 |
| B-88 | 94-308-01p | | Monsanto | Cotton | Lepidopteran resistant | 531, 757, 1076 |
| B-89 | 94-290-01p | | Zeneca & Petoseed | Tomato | Fruit polygalacturonase level decreased | B, Da, F |
| B-90 | 94-257-01p | | Monsanto | Potato | Coleopteran resistant | BT6, BT10, BT12, BT16, BT17, BT18, BT23 |
| B-91 | 94-230-01p | 92-196-01p | Calgene | Tomato | Fruit ripening altered | 9 additional FLAVRSAVR lines |
| B-92 | 94-228-01p | | DNA Plant Tech | Tomato | Fruit ripening altered | 1345-4 |
| B-93 | 94-227-01p | 92-196-01p | Calgene | Tomato | Fruit ripening altered | Line N73 1436-111 |
| B-94 | 94-090-01p | | Calgene | Rapeseed | Oil profile altered | pCGN3828-212/86- 18 & 23 |
| B-95 | 93-258-01p | | Monsanto | Soybean | Glyphosate tolerant | 40-3-2 |
| B-96 | 93-196-01p | | Calgene | Cotton | Bromoxynil tolerant | BXN |
| B-97 | 92-204-01p | | Upjohn | Squash | WMV2 & ZYMV resistant | ZW-20 |

TABLE B-continued

Non-exhaustive lists of transgenic plants and events for the conduction of experiments according to the invention obtained from the APHIS- data base of the United States Department of Agriculture (USDA). The data base can be found under the following link: http://www.aphis.usda.gov/animal_welfare/efoia/index.shtml.

| No | Petition | Extension of Petition Number *** | Institution | Crop | Transgenic Phenotype | Transformation Event or Line |
|---|---|---|---|---|---|---|
| B-98 | 92-196-01p | | Calgene | Tomato | Fruit ripening altered | FLAVR SAVR |

Abbreviation used in this table:
CMV—Cucumber Mosaic Virus
CPB—Colorado potato beetle
PLRV—Potato Leaf Roll Virus
PRSV—Papaya Ringspot Virus
PVY—Potato Virus Y
WMV2—Watermelon Mosaic Virus 2
ZYMV—Zucchini Yellow Mosaic Virus Additional particularly useful plants which may be treated according to the invention containing single transformation events or combinations of transformation events are listed for example in the databases from various national or regional regulatory agencies (see for example http://gmoinfo.jrc.it/gmp_browse.aspx and http://www.agbios.com/dbase.php).

Further particularly transgenic plants include plants which may be treated according to the invention containing a transgene in an agronomically neutral or beneficial position as described in any of the patent publications listed in Table C.

TABLE C

Non-exhaustive list of traits for the conduction of experiments with a compound of formula (I), formula (I-1-1), or formula (I-1-2) or a mixture of two compounds (I-1-1)/(I-1-7), or (I-1-2)/(I-1-8) or a composition comprising a compound of the formula (1) with a further agrochemically active ingredient according to the present invention.

| No. | Trait | Reference |
|---|---|---|
| C-1 | Water use efficiency | WO 2000/073475 |
| | | WO2009/150541 |
| | | WO2009/150541 |
| C-2 | Nitrogen use efficiency | WO 1995/009911 |
| | | WO 1997/030163 |
| | | WO 2007/092704 |
| | | WO 2007/076115 |
| | | WO 2005/103270 |
| | | WO 2002/002776 |
| | | WO2008/051608 |
| | | WO2008/112613 |
| | | WO2008/112613 |
| | | WO2008/118394 |
| | | WO2009/015096 |
| | | WO2009/061776 |
| | | WO2009/105492 |
| | | WO2009/105612 |
| | | WO2009/117853 |
| | | WO2010/006010 |
| | | WO2009/117853 |
| | | WO2009/061776 |
| | | WO2009/015096 |
| | | WO2009/105492 |
| | | WO2009/105612 |
| | | WO2010/007496 |
| | | WO2010/036866 |
| | | WO2010/053621 |
| | | WO2010/053867 |
| | | WO2010/077890 |
| | | WO2010/086220 |
| | | WO2010/111568 |
| | | WO2010/140388 |
| | | WO2010/007496 |
| C-3 | Improved photosynthesis | WO2011/022597 |
| | | WO2011/022608 |
| | | WO 2008/056915 |
| | | WO 2004/101751 |
| C-4 | Nematode resistance | WO 1995/020669 |
| | | WO 2001/051627 |
| | | WO 2008/139334 |
| | | WO 2008/095972 |
| | | WO 2006/085966 |
| | | WO 2003/033651 |
| | | WO 1999/060141 |
| | | WO 1998/012335 |
| | | WO 1996/030517 |
| | | WO 1993/018170 |
| | | WO2008/095886 |
| | | WO2008/095887 |
| | | WO2008/095888 |
| | | WO2008/095889 |
| | | WO2008/095910 |
| | | WO2008/095911 |
| | | WO2008/095916 |
| | | WO2008/095919 |
| | | WO2008/095969 |
| | | WO2008/095970 |
| | | WO2008/095972 |
| | | WO2008/110522 |
| | | WO2008/139334 |
| | | WO2008/152008 |
| | | WO2010/077858 |
| | | WO 2010/091230 |
| | | WO 2010/102172 |
| | | WO 2010/106163 |
| | | WO2011/082217 |
| | | WO2011/003783 |
| | | WO2007/146767 |
| C-5 | Reduced pod dehiscence | WO 2006/009649 |
| | | WO 2004/113542 |
| | | WO 1999/015680 |
| | | WO 1999/000502 |
| | | WO 1997/013865 |
| | | WO 1996/030529 |
| | | WO 1994/023043 |
| C-6 | Aphid resistance | WO 2006/125065 |
| | | WO 1997/046080 |
| | | WO 2008/067043 |
| | | WO 2004/072109 |

TABLE C-continued

Non-exhaustive list of traits for the conduction of experiments with a compound of formula (I), formula (I-1-1), or formula (I-1-2) or a mixture of two compounds (I-1-1)/(I-1-7), or (I-1-2)/(I-1-8) or a composition comprising a compound of the formula (1) with a further agrochemically active ingredient according to the present invention.

| No. | Trait | Reference |
|---|---|---|
| | | WO2009/091860 |
| | | WO2010036764 |
| C-7 | Sclerotinia resistance | WO 2006/135717 |
| | | WO 2006/055851 |
| | | WO 2005/090578 |
| | | WO 2005/000007 |
| | | WO 2002/099385 |
| | | WO 2002/061043 |
| C-8 | Botrytis resistance | WO 2006/046861 |
| | | WO 2002/085105 |
| C-9 | Bremia resistance | US 20070022496 |
| | | WO 2000/063432 |
| | | WO 2004/049786 |
| | | WO2009/111627 |
| | | WO2009/111627 |
| C-10 | Erwinia resistance | WO 2004/049786 |
| C-11 | Closterovirus resistance | WO 2007/073167 |
| | | WO 2007/053015 |
| | | WO 2002/022836 |
| C-12 | Stress tolerance (including drought tolerance) | WO 2010/019838 |
| | | WO 2009/049110 |
| | | WO2008/002480 |
| | | WO2005/033318 |
| | | WO2008/002480 |
| | | WO2008/005210 |
| | | WO2008/006033 |
| | | WO2008/008779 |
| | | WO2008/022486 |
| | | WO2008/025097 |
| | | WO2008/027534 |
| | | WO2008/027540 |
| | | WO2008/037902 |
| | | WO2008/046069 |
| | | WO2008/053487 |
| | | WO2008/057642 |
| | | WO2008/061240 |
| | | WO2008/064222 |
| | | WO2008/064341 |
| | | WO2008/073617 |
| | | WO2008/074025 |
| | | WO2008/076844 |
| | | WO2008/096138 |
| | | WO2008/110848 |
| | | WO2008/116829 |
| | | WO2008/117537 |
| | | WO2008/121320 |
| | | WO2008/125245 |
| | | WO2008/142034 |
| | | WO2008/142036 |
| | | WO2008/145675 |
| | | WO2008/150165 |
| | | WO2008/092935 |
| | | WO2008/145675 |
| | | WO2009/010460 |
| | | WO2009/016240 |
| | | WO2009/031664 |
| | | WO2009/038581 |
| | | WO2009/049110 |
| | | WO2009/053511 |
| | | WO2009/054735 |
| | | WO2009/067580 |
| | | WO2009/068588 |
| | | WO2009/073605 |
| | | WO2009/077611 |
| | | WO2009/079508 |
| | | WO2009/079529 |
| | | WO2009/083958 |
| | | WO2009/086229 |
| | | WO2009/092009 |
| | | WO2009/094401 |
| | | WO2009/094527 |
| | | WO2009/102965 |
| | | WO2009/114733 |
| | | WO2009/117448 |
| | | WO2009/126359 |
| | | WO2009/126462 |
| | | WO2009/129162 |
| | | WO2009/132057 |
| | | WO2009/141824 |
| | | WO2009/148330 |
| | | WO2010/003917 |
| | | WO 2010/055024 |
| | | WO 2010/058428 |
| | | WO 2010/064934 |
| | | WO2010/076756 |
| | | WO 2010/083178 |
| | | WO 2010/086221 |
| | | WO 2010/086277 |
| | | WO 2010/101818 |
| | | WO 2010/104848 |
| | | WO 2010/118338 |
| | | WO 2010/120017 |
| | | WO 2010/120054 |
| | | WO 2010/121316 |
| | | WO 2010/127579 |
| | | WO 2010/134654 |
| | | WO 2010/139993 |
| | | WO2010/039750 |
| | | WO2011/034968 |
| | | WO2011/001286 |
| | | WO2011/017492 |
| | | WO2011/018662 |
| | | WO2011/024065 |
| | | WO2011/038389 |
| | | WO2011/46772 |
| | | WO2011/053897 |
| | | WO2011/052169 |
| | | WO2011/063706 |
| | | WO2011/067745 |
| | | WO2011/079277 |
| | | WO2011/080674 |
| | | WO2011/083290 |
| | | WO2011/083298 |
| | | WO2011/091764 |
| C-13 | Tobamovirus resistance | WO 2006/038794 |
| | | WO2009086850 |
| C-14 | Yield | WO2008/125983 |
| | | WO2008/015263 |
| | | WO2008/021021 |
| | | WO2008/043849 |
| | | WO2008/044150 |
| | | WO2008/049183 |
| | | WO2008/056915 |
| | | WO2008/059048 |
| | | WO2008/062049 |
| | | WO2008/071767 |
| | | WO2008/074891 |
| | | WO2008/087932 |
| | | WO2008/092910 |
| | | WO2008/092935 |
| | | WO2008/104598 |
| | | WO2008/111779 |
| | | WO2008/122980 |
| | | WO2008/135206 |
| | | WO2008/135467 |
| | | WO2008/135603 |
| | | WO2008/137108 |
| | | WO2008/138975 |
| | | WO2008/142146 |
| | | WO2008/142163 |
| | | WO2008/145629 |
| | | WO2008/145761 |

TABLE C-continued

Non-exhaustive list of traits for the conduction of experiments with a compound of formula (I), formula (I-1-1), or formula (I-1-2) or a mixture of two compounds (I-1-1)/(I-1-7), or (I-1-2)/(I-1-8) or a composition comprising a compound of the formula (1) with a further agrochemically active ingredient according to the present invention.

| No. | Trait | Reference |
|---|---|---|
| | | WO2008/148872 |
| | | WO2009//127671 |
| | | WO2009/065912 |
| | | WO2009/000789 |
| | | WO2009/000848 |
| | | WO2009/000876 |
| | | WO2009/003977 |
| | | WO2009/009142 |
| | | WO2009/012467 |
| | | WO2009/013225 |
| | | WO2009/013263 |
| | | WO2009/014665 |
| | | WO2009/016104 |
| | | WO2009/016212 |
| | | WO2009/016232 |
| | | WO2009/034188 |
| | | WO2009/037279 |
| | | WO2009/037329 |
| | | WO2009/037338 |
| | | WO2009/040665 |
| | | WO2009/056566 |
| | | WO2009/060040 |
| | | WO2009/068564 |
| | | WO2009/072676 |
| | | WO2009/073069 |
| | | WO2009/075860 |
| | | WO2009/077973 |
| | | WO2009/080743 |
| | | WO2009/080802 |
| | | WO2009/091518 |
| | | WO2009/092772 |
| | | WO2009/095455 |
| | | WO2009/095641 |
| | | WO2009/095881 |
| | | WO2009/097133 |
| | | WO2009/106596 |
| | | WO2009/108513 |
| | | WO2009/113684 |
| | | WO2009/134339 |
| | | WO2009/135130 |
| | | WO2009/135810 |
| | | WO2009/145290 |
| | | WO2009/150170 |
| | | WO2009/153208 |
| | | WO2009/156360 |
| | | WO2010/012796 |
| | | WO2010/037228 |
| | | WO2010/000794 |
| | | WO2010/005298 |
| | | WO2010/006732 |
| | | WO2010/007035 |
| | | WO2010/012760 |
| | | WO2010/019872 |
| | | WO2010/023310 |
| | | WO2010//023320 |
| | | WO2010/025465 |
| | | WO2010/025466 |
| | | WO2010/028205 |
| | | WO2010/028456 |
| | | WO2010/033564 |
| | | WO2010/034652 |
| | | WO2010/034672 |
| | | WO2010/034681 |
| | | WO2010/035784 |
| | | WO2010/039750 |
| | | WO2010/046221 |
| | | WO2010/046471 |
| | | WO2010/049897 |
| | | WO2010/055837 |
| | | WO 2010/065867 |
| | | WO2010/069847 |
| | | WO2010/075143 |
| | | WO2010/075243 |
| | | WO2010/100595 |
| | | WO2010/102220 |
| | | WO2010/104092 |
| | | WO2010/108836 |
| | | WO2010/120862 |
| | | WO2010/123667 |
| | | WO2010/124953 |
| | | WO2010/125036 |
| | | WO2010/127969 |
| | | WO2010/129501 |
| | | WO2010/140388 |
| | | WO2010/140672 |
| | | WO2011/011273 |
| | | WO2011/000466 |
| | | WO2011/003800 |
| | | WO2011/006717 |
| | | WO2011/008510 |
| | | WO2011/009801 |
| | | WO2011/011412 |
| | | WO2011/015985 |
| | | WO2011/020746 |
| | | WO2011/021190 |
| | | WO2011/025514 |
| | | WO2011/025515 |
| | | WO2011/025516 |
| | | WO2011/025840 |
| | | WO2011/031680 |
| | | WO2011/036160 |
| | | WO2011/036232 |
| | | WO2011/041796 |
| | | WO2011/044254 |
| | | WO2011/048009 |
| | | WO2011/053898 |
| | | WO2011/051120 |
| | | WO2011/058029 |
| | | WO2011/061656 |
| | | WO2011/085062 |
| | | WO2011/088065 |
| C-15 | Oil content/composition | WO 2010/045324 |
| | | WO 2010/053541 |
| | | WO 2010/130725 |
| | | WO 2010/140682 |
| | | WO2011/006948 |
| | | WO2011/049627 |
| | | WO2011/060946 |
| | | WO2011/062748 |
| | | WO2011/064181 |
| | | WO2011/064183 |
| | | WO2011/075716 |
| | | WO2011/079005 |
| C-16 | Biopharmaceutical production | WO 2010/121818 |
| C-17 | Improved recombination | WO2010/071418 |
| | | WO 2010/133616 |
| C-18 | Altered inflorescence | WO 2010/069004 |
| C-19 | Disease control (other) | WO 2010/059558 |
| | | WO2010/075352 |
| | | WO2010/075498 |
| | | WO 2010/085289 |
| | | WO 2010/085295 |
| | | WO 2010/085373 |
| | | WO2009/000736 |
| | | WO2009/065863 |
| | | WO2009/112505 |
| | | WO 2010/089374 |
| | | WO 2010/120452 |
| | | WO 2010/123904 |
| | | WO 2010/135782 |
| | | WO2011/025860 |
| | | WO2011/041256 |

TABLE C-continued

Non-exhaustive list of traits for the conduction of experiments with a compound of formula (I), formula (I-1-1), or formula (I-1-2) or a mixture of two compounds (I-1-1)/(I-1-7), or (I-1-2)/(I-1-8) or a composition comprising a compound of the formula (1) with a further agrochemically active ingredient according to the present invention.

| No. | Trait | Reference |
|---|---|---|
|  |  | WO2011/002992 |
|  |  | WO2011/014749 |
|  |  | WO2011/031006 |
|  |  | WO2011/031922 |
|  |  | WO2011/075584 |
|  |  | WO2011/075585 |
|  |  | WO2011/075586 |
|  |  | WO2011/075587 |
|  |  | WO2011/075588 |
|  |  | WO2011/084622 |
|  |  | WO2011/084626 |
|  |  | WO2011/084627 |
|  |  | WO2011/084629 |
|  |  | WO2011/084630 |
|  |  | WO2011/084631 |
|  |  | WO2011/084314 |
|  |  | WO2011/084324 |
|  |  | WO2011/023571 |
|  |  | WO2011/040880 |
|  |  | WO2011/082304 |
|  |  | WO2011/003783 |
|  |  | WO2011/020797 |
| C-20 | Herbicide tolerance | U.S. Pat. No. 4,761,373 |
|  |  | U.S. Pat. No. 5,304,732 |
|  |  | U.S. Pat. No. 5,331,107 |
|  |  | U.S. Pat. No. 5,718,079 |
|  |  | U.S. Pat. No. 6,211,438 |
|  |  | U.S. Pat. No. 6,211,439 |
|  |  | U.S. Pat. No. 6,222,100 |
|  |  | US 2003/0217381 |
|  |  | US 2003/0217381 |
|  |  | WO2004/106529 |
|  |  | WO2000/27182 |
|  |  | WO2005/20673 |
|  |  | WO 2001/85970 |
|  |  | U.S. Pat. No. 5,545,822 |
|  |  | U.S. Pat. No. 5,736,629 |
|  |  | U.S. Pat. No. 5,773,703 |
|  |  | U.S. Pat. No. 7,405,347 |
|  |  | U.S. Pat. No. 7,504,561 |
|  |  | U.S. Pat. No. 7,538,262 |
|  |  | U.S. Pat. No. 7,488,866 |
|  |  | U.S. Pat. No. 7,534,937 |
|  |  | U.S. Pat. No. 7,700,842 |
|  |  | U.S. Pat. No. 7,674,958 |
|  |  | U.S. Pat. No. 7,910,805 |
|  |  | U.S. Pat. No. 7,960,615 |
|  |  | U.S. Pat. No. 8,003,854 |
|  |  | U.S. Pat. No. 7,834,249 |
|  |  | US 2008/0313769 |
|  |  | US 2007/0289035 |
|  |  | US 2007/0295251 |

Additional particularly useful plants which may be treated according to the invention with the compound of a compound of formula (I), formula (I-1-1), or formula (I-1-2) or a mixture of two compounds (I-1-1)/(I-1-7), or (I-1-2)/(I-1-8) or a composition comprising a compound of the formula (I) with a further agrochemically active ingredient are plants, containing and expressing a transgenic event according to D1-D48 as listed in Table D.

TABLE D

Non-exhaustive list of characteristics of transgenic plants which may be treated with a compound of formula (I), formula (I-1-1), or formula (I-1-2) or a mixture of two compounds (I-1-1)/(I-1-7), or (I-1-2)/(I-1-8) or a composition comprising a compound of the formula (1) with a further agrochemically active ingredient according to the invention.

| No. | Plant species | Transgenic event | Trait | Patent reference |
|---|---|---|---|---|
| D-1 | Corn | PV-ZMGT32 (NK603) | Glyphosate tolerance | US 2007-056056 |
| D-2 | Corn | MIR604 | Insect resistance (Cry3a055) | EP 1 737 290 |
| D-3 | Corn | LY038 | High lysine content | U.S. Pat. No. 7,157,281 |
| D-4 | Corn | 3272 | Self processing corn (alpha-amylase) | US 2006-230473 |
| D-5 | Corn | PV-ZMIR13 (MON863) | Insect resistance (Cry3Bb) | US 2006-095986 |
| D-6 | Corn | DAS-59122-7 | Insect resistance (Cry34Ab1/Cry35Ab1) | US 2006-070139 |
| D-7 | Corn | TC1507 | Insect resistance (Cry1F) | U.S. Pat. No. 7,435,807 |
| D-8 | Corn | MON810 | Insect resistance (Cry1Ab) | US 2004-180373 |
| D-9 | Corn | VIP1034 | Insect resistance | WO 03/052073 |
| D-10 | Corn | B16 | Glufosinate resistance | US 2003-126634 |
| D-11 | Corn | GA21 | Glyphosate resistance | U.S. Pat. No. 6,040,497 |
| D-12 | Corn | GG25 | Glyphosate resistance | U.S. Pat. No. 6,040,497 |
| D-13 | Corn | GJ11 | Glyphosate resistance | U.S. Pat. No. 6,040,497 |
| D-14 | Corn | FI117 | Glyphosate resistance | U.S. Pat. No. 6,040,497 |
| D-15 | Corn | GAT-ZM1 | Glufosinate tolerance | WO 01/51654 |
| D-16 | Corn | DP-098140-6 | Glyphosate tolerance/ALS inhibitor tolerance | WO 2008/112019 |
| D-17 | Wheat | Event 1 | Fusarium resistance (trichothecene 3-O-acetyltransferase) | CA 2561992 |
| D-18 | Sugar beet | T227-1 | Glyphosate tolerance | US 2004-117870 |
| D-19 | Sugar beet | H7-1 | Glyphosate tolerance | WO 2004-074492 |
| D-20 | Soybean | MON89788 | Glyphosate tolerance | US 2006-282915 |

TABLE D-continued

Non-exhaustive list of characteristics of transgenic plants which may
be treated with a compound of formula (I), formula (I-1-1), or formula
(I-1-2) or a mixture of two compounds (I-1-1)/(I-1-7), or (I-1-2)/(I-1-8) or
a composition comprising a compound of the formula (1) with a further
agrochemically active ingredient according to the invention.

| No. | Plant species | Transgenic event | Trait | Patent reference |
| --- | --- | --- | --- | --- |
| D-21 | Soybean | A2704-12 | Glufosinate tolerance | WO 2006/108674 |
| D-22 | Soybean | A5547-35 | Glufosinate tolerance | WO 2006/108675 |
| D-23 | Soybean | DP-305423-1 | High oleic acid/ALS inhibitor tolerance | WO 2008/054747 |
| D-24 | Rice | GAT-OS2 | Glufosinate tolerance | WO 01/83818 |
| D-25 | Rice | GAT-OS3 | Glufosinate tolerance | US 2008-289060 |
| D-26 | Rice | PE-7 | Insect resistance (Cry1Ac) | WO 2008/114282 |
| D-27 | Oilseed rape | MS-B2 | Male sterility | WO 01/31042 |
| D-28 | Oilseed rape | MS-BN1/RF-BN1 | Male sterility/restoration | WO 01/41558 |
| D-29 | Oilseed rape | RT73 | Glyphosate resistance | WO 02/36831 |
| D-30 | Cotton | CE43-67B | Insect resistance (Cry1Ab) | WO 2006/128573 |
| D-31 | Cotton | CE46-02A | Insect resistance (Cry1Ab) | WO 2006/128572 |
| D-32 | Cotton | CE44-69D | Insect resistance (Cry1Ab) | WO 2006/128571 |
| D-33 | Cotton | 1143-14A | Insect resistance (Cry1Ab) | WO 2006/128569 |
| D-34 | Cotton | 1143-51B | Insect resistance (Cry1Ab) | WO 2006/128570 |
| D-35 | Cotton | T342-142 | Insect resistance (Cry1Ab) | WO 2006/128568 |
| D-36 | Cotton | event3006-210-23 | Insect resistance (Cry1Ac) | WO 2005/103266 |
| D-37 | Cotton | PV-GHGT07 (1445) | Glyphosate tolerance | US 2004-148666 |
| D-38 | Cotton | MON88913 | Glyphosate tolerance | WO 2004/072235 |
| D-39 | Cotton | EE-GH3 | Glyphosate tolerance | WO 2007/017186 |
| D-40 | Cotton | T304-40 | Insect-resistance (Cry1Ab) | WO2008/122406 |
| D-41 | Cotton | Cot202 | Insect resistance (VIP3) | US 2007-067868 |
| D-42 | Cotton | LLcotton25 | Glufosinate resistance | WO 2007/017186 |
| D-43 | Cotton | EE-GH5 | Insect resistance (Cry1Ab) | WO 2008/122406 |
| D-44 | Cotton | event 281-24-236 | Insect resistance (Cry1F) | WO 2005/103266 |
| D-45 | Cotton | Cot102 | Insect resistance (Vip3A) | US 2006-130175 |
| D-46 | Cotton | MON 15985 | Insec resistance (Cry1A/Cry2Ab) | US 2004-250317 |
| D-47 | Bent Grass | Asr-368 | Glyphosate tolerance | US 2006-162007 |
| D-48 | Brinjal | EE-1 | Insect resistance (Cry1Ac) | WO 2007/091277 |

Additional particularly useful transgenic plants include plants which may be treated according to the invention containing and expressing one or more transgene and are described by the trade name in Table E.

TABLE E

Non-exhaustive lists of transgenic events and its trade names.

| No. | Trade name | Crop | Company | Genetic Modification | Additional information |
| --- | --- | --- | --- | --- | --- |
| E-1 | Roundup Ready ® | *Beta vulgaris* (sugarbeet) | Monsanto Company | Glyphosate tolerance | |
| E-2 | InVigor ® | *Brassica napus* (canola) | Bayer CropScience | Canola was transformed as described: Ø Expression of a gene that introduces tolerance to the herbicide Glyfosinate-Ammonium; Ø Introduction of a new hybridisation system for canola based on genetically modified pollen sterility (MS) and fertility restorer (RF) lines; Ø Expression of a gene introducing antibiotic resistence | |
| E-3 | Liberty Link ® | *Brassica napus* (canola) | BayerCropScience | Tolerance to Phosphinotricin | |
| E-4 | Roundup Ready ® | *Brassica napus* (canola) | Monsanto Company | Glyphosate tolerance | |
| E-5 | Clearfield ® | *Brassica napus* (canola) | BASF Corporation | Non-GM, tolerance to Imazamox | |
| E-6 | Optimum ™ GAT ™ | *Glycine max* L. (soybean) | Pioneer Hi-Bred International, Inc | Glyphosate and ALS-inhibitor tolerance | |

TABLE E-continued

Non-exhaustive lists of transgenic events and its trade names.

| No. | Trade name | Crop | Company | Genetic Modification | Additional information |
|---|---|---|---|---|---|
| E-7 | Roundup Ready ® | *Glycine max* L. (soybean) | Monsanto Company | Glyphosate tolerance | |
| E-8 | Roundup RReady2Yiel ™ | *Glycine max* L. (soybean) | Monsanto Company | Glyphosate tolerance | |
| E-9 | STS ® | *Glycine max* L. (soybean) | DuPont | Tolerance to Sulfonyl ureas | |
| E-10 | YIELD GARD ® | *Glycine max* L. (soybean) | Monsanto Company | | |
| E-11 | AFD ® | *Gossypium hirsutum* L. (cotton) | Bayer CropScience | The following lines belong to AFD ®: AFD5062LL, AFD5064F, AFD5065B2F; AFD seeds are available for different varieties/cultivars with integrated technology, for example technologies like Bollgard ®, Bollgard II, Roundup Ready, Roundup Ready Flex and LibertyLink ® | |
| E-12 | Bollgard II ® | *Gossypium hirsutum* L. (cotton) | Monsanto Company | MON 15985-Event: Cry2(A)b1; Cry1A(c) | |
| E-13 | Bollgard ® | *Gossypium hirsutum* L. (cotton) | Monsanto Company | Cry 1Ac | |
| E-14 | FiberMax ® | *Gossypium hirsutum* L. (cotton) | Bayer CropScience | | |
| E-15 | Liberty Link ® | *Gossypium hirsutum* L. (cotton) | Bayer CropScience | Tolerance to Phosphinotricin | |
| E-16 | Nucotn 33B | *Gossypium hirsutum* L. (cotton) | Delta Pine and Land | Bt toxin in varieties/cultivars of Delta Pine: Cry1Ac | |
| E-17 | Nucotn 35B | *Gossypium hirsutum* L. (cotton) | Delta Pine and Land | Bt toxin in varieties/cultivars of Delta Pine: Cry1Ac | |
| E-18 | Nucotn ® | *Gossypium hirsutum* L. (cotton) | Delta Pine and Land | Bt toxin in varieties/cultivars of Delta Pine | |
| E-19 | PhytoGen ™ | *Gossypium hirsutum* L. (cotton) | PhytoGen Seed Company, Dow AgroSciences LLC | Includes varieties/cultivars which contain for example Roundup Ready flex, Widestrike | |
| E-20 | Roundup Ready Flex ® | *Gossypium hirsutum* L. (cotton) | Monsanto Company | Glyphosate tolerance | |
| E-21 | Roundup Ready ® | *Gossypium hirsutum* L. (cotton) | Monsanto Company | Glyphosate tolerance | |
| E-22 | Widestrike ™ | *Gossypium hirsutum* L. (cotton) | Dow AgroSciences LLC | Cry1F and Cry1Ac | Monsanto/Dow |
| E-23 | YIELD GARD ® | *Gossypium hirsutum* L. (cotton) | Monsanto Company | | http://www.garstseed.com/GarstClient/Technology/agrisure.aspx |
| E-24 | Roundup Ready ® | *Medicago sativa* (alfalfa) | Monsanto Company | Glyphosate tolerance | |
| E-25 | Clearfield ® | *Oryza sativa* (rice) | BASF Corporation | Non-GM, tolerance to Imazamox | |
| E-26 | NewLeaf ® | *Solanum tuberosum* L. (potato) | Monsanto Company | Resistance against infection with potato leaf roll virus (PLRV) and damage caused by the potato beetle *Leptinotarsa decemlineata* | |
| E-27 | NewLeaf ® plus | *Solanum tuberosum* L. (potato) | Monsanto Company | Resistance against infection with potato leaf roll virus (PLRV) and damage caused by the potato beetle *Leptinotarsa decemlineata* | http://www.dowagro.com/phytogen/index.htm |

TABLE E-continued

Non-exhaustive lists of transgenic events and its trade names.

| No. | Trade name | Crop | Company | Genetic Modification | Additional information |
|---|---|---|---|---|---|
| E-28 | Protecta ® | *Solanum tuberosum* L. (potato) | | | |
| E-29 | Clearfield ® | Sunflower | BASF Corporation | Non-GM, tolerance to Imazamox | |
| E-30 | Roundup Ready ® | *Triticum aestivum* (wheat) | Monsanto Company | Glyphosate tolerance NK603 | |
| E-31 | Clearfield ® | *Triticum aestivum* (wheat) | BASF Corporation | Non-GM, tolerance to Imazamox | |
| E-32 | Agrisure ® (Familie) | *Zea mays* L. (corn) | Syngenta Seeds, Inc. | comprises Agrisure CB/LL (BT 11 event plus Phosphinotricin tolerance mediated by GA21 event); Agrisure CB/LL/RW (Bt 11 event, modified synthetic cry3A gene, Phosphinotricin tolerance mediated by GA21 event); Agrisure GT (Glyphosate tolerance); Agrisure GT/CB/LL(Glyphosate and tolerance Phosphinotricin tolerance mediated by GA21 event, Bt 11 event); Agrisure 3000GT (CB/LL/RW/GT: Glyphosate and tolerance Phosphinotricin tolerance mediated by GA21 event, Bt 11 event, modified synthetic cry3A gene); Agrisure GT/RW (Glyphosate tolerance, modified synthetic cry3A gene); Agrisure RW (modified synthetic cry3A gene); future traits | |
| E-33 | BiteGard ® | *Zea mays* L. (corn) | Novartis Seeds | cry1A(b) gene | |
| E-34 | Bt-Xtra ® | *Zea mays* L. (corn) | DEKALB Genetics Corporation | cry1Ac gene | |
| E-35 | Clearfield ® | *Zea mays* L. (corn) | BASF Corporation | Non-GM, tolerance to Imazamox | |
| E-36 | Herculex ® (Familie) | *Zea mays* L. (corn) | Dow AgroSciences LLC | | |
| E-37 | IMI ® | *Zea mays* L. (corn) | DuPont | Toleranz fur Imidazolinone | |
| E-38 | KnockOut ® | *Zea mays* L. (corn) | Syngenta Seeds, Inc. | SYN-EV176-9: cry1A(b)-Gen. | |
| E-39 | Mavera ® | *Zea mays* L. (corn) | Renessen LLC | Lysine rich | http://www.dowagro.com/widestrike/ |
| E-40 | NatureGard ® | *Zea mays* L. (corn) | Mycogen | cry1A(b) gene | |
| E-41 | Roundup Ready ® | *Zea mays* L. (corn) | Monsanto Company | Glyphosate tolerance | http://www.starlinkcorn.com/starlinkcorn.htm |
| E-42 | Roundup Ready ® 2 | *Zea mays* L. (corn) | Monsanto Company | Glyphosate tolerance | |
| E-43 | SmartStax | *Zea mays* L. (corn) | Monsanto Company | Combination of eight genes | |
| E-44 | StarLink ® | *Zea mays* L. (corn) | Aventis CropScience ->Bayer CropScience | Cry9c gene | |
| E-45 | STS ® | *Zea mays* L. (corn) | DuPont | Tolerance to Sulfonyl ureas | |
| E-46 | YIELD GARD ® | *Zea mays* L. (corn) | Monanto Company | Mon810, Cry1Ab1; Resistance against European corn borer | http://www.dowagro.com/herculex/about/herculexfamily/ |

TABLE E-continued

Non-exhaustive lists of transgenic events and its trade names.

| No. | Trade name | Crop | Company | Genetic Modification | Additional information |
|---|---|---|---|---|---|
| E-47 | YieldGard ® Plus | Zea mays L. (corn) | Monsanto Company | Mon810×Mon863, double stack, resistance against European corn borer and Western corn rootworm | |
| E-48 | YieldGard ® Rootworm | Zea mays L. (corn) | Monsanto Company | Mon863, Cry3Bb1, resistance against Western corn rootworm | |
| E-49 | YieldGard ® VT | Zea mays L. (corn) | Monsanto Company | Combination of several traits | |
| E-50 | YieldMaker ™ | Zea mays L. (corn) | DEKALB Genetics Corporation | contains Roundup Ready 2-Technology, YieldGard VT, YieldGard Corn Borer, YieldGard Rootworm and YieldGard Plus | |

Additional particularly useful plants which may be treated according to the invention with a compound of the formula (I), formula (I-1-1), or formula (I-1-2) or a mixture of two compounds (I-1-1)/(I-1-7), or (I-1-2)/(I-1-8) or a composition comprising a compound of the formula (I) with a further agrochemically active ingredient are plants or plant cultivars (that can be obtained by plant biotechnology methods such as genetic engineering) that contain multi stacks (alternative: combination) of one or more insect control traits and/or one or more nematode control traits and/or one or more herbicide tolerance/resistance traits and/or one or more disease control traits and/or one or more yield increasing traits and/or one or more quality altering traits and/or one or more abiotic stress traits.

Additional particularly useful plants or plant cultivars (that can be obtained by plant biotechnology methods such as genetic engineering) which may also be treated with a compound of the formula (I), formula (I-1-1), or formula (I-1-2) or a mixture of two compounds (I-1-1)/(I-1-7), or (I-1-2)/(I-1-8) or a composition comprising a compound of the formula (I), formula (I-1-1), or formula (I-1-2) or a mixture of two compounds (I-1-1)/(I-1-7), or (I-1-2)/(I-1-8) with a further agrochemically active ingredient according to the invention are plants that contain multi stacks (alternative: combination) of one or more insect control traits and/or one or more nematode control traits and/or one or more herbicide tolerance/resistance traits and/or one or more yield increasing traits and/or one or more abiotic stress traits.

Additional particularly useful plants or plant cultivars (that can be obtained by plant biotechnology methods such as genetic engineering) which may also be treated with a compound of the formula (I), formula (I-1-1), or formula (I-1-2) or a mixture of two compounds (I-1-1)/(I-1-7), or (I-1-2)/(I-1-8) or a composition comprising a compound of the formula (I) with a further agrochemically active ingredient according to the invention are plants that contain multi stacks (alternative: combination) of one or more insect control traits and/or one or more nematode control traits and/or one or more herbicide tolerance/resistance traits and/or one or more yield increasing traits.

Additional particularly useful plants or plant cultivars (that can be obtained by plant biotechnology methods such as genetic engineering) which may also be treated with a compound of the formula (I), formula (I-1-1), or formula (I-1-2) or a mixture of two compounds (I-1-1)/(I-1-7), or (I-1-2)/(I-1-8) or a composition comprising a compound of the formula (I) with a further agrochemically active ingredient according to the invention are plants that contain multi stacks (alternative: combination) of one or more insect control traits and/or one or more nematode control traits and/or one or more herbicide tolerance/resistance traits and/or one or more abiotic stress traits.

Additional particularly useful plants or plant cultivars (that can be obtained by plant biotechnology methods such as genetic engineering) which may also be treated with a compound of the formula (I), formula (I-1-1), or formula (I-1-2) or a mixture of two compounds (I-1-1)/(I-1-7), or (I-1-2)/(I-1-8) or a composition comprising a compound of the formula (I) with a further agrochemically active ingredient according to the invention are plants that contain multi stacks (alternative: combination) of one or more insect control traits and/or one or more nematode control traits and/or one or more herbicide tolerance/resistance traits.

Formulations

The present invention further provides formulations, and application forms prepared from them, as crop protection agents and/or pesticidal agents, such as drench, drip and spray liquors, comprising at least one of the active compounds of the invention. The application forms may comprise further crop protection agents and/or pesticidal agents, and/or activity-enhancing adjuvants such as penetrants, examples being vegetable oils such as, for example, rapeseed oil, sunflower oil, mineral oils such as, for example, liquid paraffins, alkyl esters of vegetable fatty acids, such as rapeseed oil or soybean oil methyl esters, or alkanol alkoxylates, and/or spreaders such as, for example, alkylsiloxanes and/or salts, examples being organic or inorganic ammonium or phosphonium salts, examples being ammonium sulphate or diammonium hydrogen phosphate, and/or retention promoters such as dioctyl sulphosuccinate or hydroxypropylguar polymers and/or humectants such as glycerol and/or fertilizers such as ammonium, potassium or phosphorous fertilizers, for example.

Examples of typical formulations include water-soluble liquids (SL), emulsifiable concentrates (EC), emulsions in water (EW), suspension concentrates (SC, SE, FS, OD), water-dispersible granules (WG), granules (GR) and capsule concentrates (CS); these and other possible types of formulation are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations may comprise active agrochemical compounds other than one or more active compounds of the invention.

The formulations or application forms in question preferably comprise auxiliaries, such as extenders, solvents, spontaneity promoters, carriers, emulsifiers, dispersants, frost protectants, biocides, thickeners and/or other auxiliaries, such as adjuvants, for example. An adjuvant in this context is a component which enhances the biological effect of the formulation, without the component itself having a biological effect. Examples of adjuvants are agents which promote the retention, spreading, attachment to the leaf surface, or penetration.

These formulations are produced in a known manner, for example by mixing the active compounds with auxiliaries such as, for example, extenders, solvents and/or solid carriers and/or further auxiliaries, such as, for example, surfactants. The formulations are prepared either in suitable plants or else before or during the application.

Suitable for use as auxiliaries are substances which are suitable for imparting to the formulation of the active compound or the application forms prepared from these formulations (such as, e.g., usable crop protection agents, such as spray liquors or seed dressings) particular properties such as certain physical, technical and/or biological properties.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

In principle it is possible to use all suitable solvents. Suitable solvents are, for example, aromatic hydrocarbons, such as xylene, toluene or alkylnaphthalenes, for example, chlorinated aromatic or aliphatic hydrocarbons, such as chlorobenzene, chloroethylene or methylene chloride, for example, aliphatic hydrocarbons, such as cyclohexane, for example, paraffins, petroleum fractions, mineral and vegetable oils, alcohols, such as methanol, ethanol, isopropanol, butanol or glycol, for example, and also their ethers and esters, ketones such as acetone, methyl ethyl ketone, methyl isobutyl ketone or cyclohexanone, for example, strongly polar solvents, such as dimethyl sulphoxide, and water.

All suitable carriers may in principle be used. Suitable carriers are in particular: for example, ammonium salts and ground natural minerals such as kaolins, clays, talc, chalk, quartz, attapulgite, montmorillonite or diatomaceous earth, and ground synthetic minerals, such as finely divided silica, alumina and natural or synthetic silicates, resins, waxes and/or solid fertilizers. Mixtures of such carriers may likewise be used. Carriers suitable for granules include the following: for example, crushed and fractionated natural minerals such as calcite, marble, pumice, sepiolite, dolomite, and also synthetic granules of inorganic and organic meals, and also granules of organic material such as sawdust, paper, coconut shells, maize cobs and tobacco stalks.

Liquefied gaseous extenders or solvents may also be used. Particularly suitable are those extenders or carriers which at standard temperature and under standard pressure are gaseous, examples being aerosol propellants, such as halogenated hydrocarbons, and also butane, propane, nitrogen and carbon dioxide.

Examples of emulsifiers and/or foam-formers, dispersants or wetting agents having ionic or nonionic properties, or mixtures of these surface-active substances, are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyltaurates), phosphoric esters of polyethoxylated alcohols or phenols, fatty acid esters of polyols, and derivatives of the compounds containing sulphates, sulphonates and phosphates, examples being alkylaryl polyglycol ethers, alkylsulphonates, alkyl sulphates, arylsulphonates, protein hydrolysates, lignin-sulphite waste liquors and methylcellulose. The presence of a surface-active substance is advantageous if one of the active compounds and/or one of the inert carriers is not soluble in water and if application takes place in water.

Further auxiliaries that may be present in the formulations and in the application forms derived from them include colorants such as inorganic pigments, examples being iron oxide, titanium oxide, Prussian Blue, and organic dyes, such as alizarin dyes, azo dyes and metal phthalocyanine dyes, and nutrients and trace nutrients, such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present. Additionally present may be foam-formers or defoamers.

Furthermore, the formulations and application forms derived from them may also comprise, as additional auxiliaries, stickers such as carboxymethylcellulose, natural and synthetic polymers in powder, granule or latex form, such as gum arabic, polyvinyl alcohol, polyvinyl acetate, and also natural phospholipids, such as cephalins and lecithins, and synthetic phospholipids. Further possible auxiliaries include mineral and vegetable oils.

There may possibly be further auxiliaries present in the formulations and the application forms derived from them. Examples of such additives include fragrances, protective colloids, binders, adhesives, thickeners, thixotropic substances, penetrants, retention promoters, stabilizers, sequestrants, complexing agents, humectants and spreaders. Generally speaking, the active compounds may be combined with any solid or liquid additive commonly used for formulation purposes.

Suitable retention promoters include all those substances which reduce the dynamic surface tension, such as dioctyl sulphosuccinate, or increase the viscoelasticity, such as hydroxypropylguar polymers, for example.

Suitable penetrants in the present context include all those substances which are typically used in order to enhance the penetration of active agrochemical compounds into plants. Penetrants in this context are defined in that, from the (generally aqueous) application liquor and/or from the spray coating, they are able to penetrate the cuticle of the plant and thereby increase the mobility of the active compounds in the cuticle. This property can be determined using the method described in the literature (Baur et al., 1997, Pesticide Science 51, 131-152). Examples include alcohol alkoxylates such as coconut fatty ethoxylate (10) or isotridecyl ethoxylate (12), fatty acid esters such as rapeseed or soybean oil methyl esters, fatty amine alkoxylates such as tallowamine ethoxylate (15), or ammonium and/or phosphonium salts such as ammonium sulphate or diammonium hydrogen phosphate, for example.

The formulations preferably comprise between 0.00000001% and 98% by weight of active compound or, with particular preference, between 0.01% and 95% by weight of active compound, more preferably between 0.5% and 90% by weight of active compound, based on the weight of the formulation.

The active compound content of the application forms (crop protection products) prepared from the formulations may vary within wide ranges. The active compound concentration of the application forms may be situated typically between 0.00000001% and 95% by weight of active compound, preferably between 0.00001% and 1% by weight, based on the weight of the application form.

In the compositions according to the invention the ratio of a compound of the formula (I) to an agrochemically active compound of group (B) can be varied within a relatively wide range. In general, the inventive combinations comprise active ingredients of the formula (I) to the mixing partner from group (II) in a ratio of 625:1 to 1:625; preferably in a ratio of 125:1 to 1.125, more preferably in a ratio of 25:1 to 1:25, even more preferably in a ratio of 5:1 to 1:5.

Application Methods

The treatment according to the invention of the plants and plant parts with a compound of the formula (I) or compositions is carried out directly or by action on their surroundings, habitat or storage space using customary treatment methods, for example by dipping, spraying, atomizing, irrigating, stem injection, in-furrow application, evaporating, dusting, fogging, broadcasting, foaming, painting, spreading-on, watering (drenching), drip irrigating and, in the case of propagation material, in particular in the case of seeds, furthermore as a powder for dry seed treatment, a solution for seed treatment, a water-soluble powder for slurry treatment, by incrusting, by coating with one or more layers, etc. It is furthermore possible to apply the active compounds by the ultra-low volume method, or to inject the active compound preparation or the active compound itself into the soil.

Generally, a compound of the formula (I) is applied in a rate of 1 g to 20 kg per ha, preferably 5 g to 5 kg per ha, most preferably 10 g to 1 kg per ha.

EXAMPLES

Formula for the Efficacy of the Combination of Two Compounds

The expected efficacy of a given combination of two compounds is calculated as follows (see Colby, S. R., "Calculating Synergistic and antagonistic Responses of Herbicide Combinations", Weeds 15, pp. 20-22, 1967):

if

X is the efficacy expressed in % mortality of insects on the control plants treated with compound A at a concentration of m ppm or m g/ha, Y is the efficacy expressed in % mortality of insects on the untreated transgenic plant expressing one or more insect-controlling transgenes E is the efficacy expressed in % mortality of insects on the transgenic plant expressing one or more insect-controlling transgenes and being treated with compound A then is $$E = X + Y - \frac{X \cdot Y}{100}.$$

If the observed insecticidal efficacy of the combination is higher than the one calculated as "E", then the combination of the two compounds is more than additive, i.e., there is a synergistic effect.

Example 1

*Nilaparvata lugens* on Transgenic Rice (*Oryza sativa*)

| Solvent: | 7 parts by weight of dimethylformamide |
| Emulsifier: | 2 parts by weight of alkylaryl polyglycolether |

To produce a suitable preparation of active compound, 1 part by weight of active compound is mixed with the stated amount of solvent and emulsifier, and the concentrate is diluted with emulsifier-containing water to the desired concentration.

Pots with transgenic rice plants containing insect resistance and herbicide resistance genes and non-transgenic control plants are treated in 2 replicates by being sprayed with the preparation of the active compound of the desired concentration and infested with larvae of the brown plant hopper (*Nilaparvata lugens*).

After the specified period of time, the mortality in % is determined. 100% means that all the larvae have been killed; 0% means that none of the larvae have been killed.

The results obtained were compared to the results of the compound on non-transgenic rice plants and the results of the non-treated transgenic rice plants.

TABLE 1

*Nilaparvata lugens* on rice

| Active Compound | Concentration in ppm | Mortality in % after 2 d | |
| --- | --- | --- | --- |
| Compound (I-1-1)/(I-1-7) on non-transgenic rice | 100 | 20 | |
| rice containing plant expressible Cry1Ab, Cry1C genes | — | 0 | |
| | | obs* | cal.** |
| Compound (I-1-1)/(I-1-7) on rice containing plant expressible Cry1Ab, Cry1C genes According to the invention | 100 | 100 | 20 |

*obs. = observed insecticidal efficacy,
**cal. = efficacy calculated with Colby-formula Example 2

*Zea Mays* (Corn) seed from events traited with Axmi205 were selected. Axmi205 historically shows efficacy against *Diabrotica virgifera* (western corn rootworm). The population of the seed used is not entirely transgenic; plants without the trait in their DNA were used for control comparisons.

Seed was treated with seed applied compound (I-1-1/I-1-7) using a hege bowl treater. Rates were applied as mg ai/seed.

Each chemical evaluation was handled as a separate trial and had non-target variables controlled.

During testing, samples of each plant were submitted for PCR to determine if an individual plant carried the Axmi205 gene (positive or negative). Plants for which no PCR results could be obtained were not included in the results.

Seed were planted into germination mix at a rate of one seed per root-trainer. Testing was conducted as a randomized complete block with 30 replications. Plants were maintained in a greenhouse and periodically assessed for emergence. After approximately three weeks from planting, plants were infested with *Diabrotica virgifera* (western corn rootworm). Western corn rootworm eggs were infested into the root system of plants. At approximately 15 days post infestation plants were extracted and insect feeding damage was evaluated following Iowa State University's Node-Injury Scale at www.ent.iastate.edu/pest/rootworm/nodeinjury/nodeinjury.html.

The trait Axmi205 is known to have efficacy on western corn rootworm (*D. virgifera*). Compound (I-1-1)/(I-1-7) is an experimental insecticide. Witnessed root damage in the controls was lower than that of seed treated with the lowest rate of Compound (I-1-1)/(I-1-7). This could be due to lower pressure in the control due to variation within pest establishment. Compound (I-1-1)/(I-1-7) as an individual component appeared to present little efficacy against western corn rootworm. However, examining Compound (I-1-1)/(I-1-7) at a rate of 0.125 mg ai/seed there was a 26% reduction in root feeding damage in the presences of Axmi205. At the highest rate of Compound (I-1-1)/(I-1-7) the reduction increases to 32%. The addition of Compound (I-1-1)/(I-1-7) at a rate of 0.5 mg ai/seed to Axmi205 also resulted in a 32% reduction of root damage, while the addition of Compound (I-1-1)/(I-1-7) to negative seed did not consistently result in reduced damage. At the highest rate of Compound (I-1-1)/(I-1-7)), the presence of Amxi205 reduced root damage by more than one would expect from Axmi205 alone (11% to 32%). See Table 2.

TABLE 2

| | PCR | Plant Emergence | | | | Insect Efficacy |
|---|---|---|---|---|---|---|
| Trait Target Criteria | Axmi205 Corn Negative or Positive | Axmi205 Corn Emerged | Axmi205 Corn Emerged | Axmi205 Corn Emerged | Axmi205 Corn Emerged | Axmi205 *D. virgifera* Root Damage Rating |
| Trt/Date | 7/19/2011 | 7/10/2011 | 7/11/2011 | 7/12/2011 | 7/14/2011 | 8/23/2011 |
| UTC** | Negative 11 plants | 7% | 37% | 37% | 37% | 0.89 |
| UTC + Axmi205 | Positive 18 plants | 7% | 60% | 60% | 60% | 0.79 |
| COMPOUND (I-1-1)/(I-1-7) @ 0.125 mg ai/seed + Axmi205 | Negative 12 plants | 0% | 40% | 40% | 40% | 1.56 |
| COMPOUND (I-1-1)/(I-1-7) @ 0.125 mg ai/seed + Axmi205 | Positive 17 plants | 0% | 57% | 57% | 57% | 1.16 |
| COMPOUND (I-1-1)/(I-1-7) @ 0.25 mg ai/seed | Negative 18 plants | 17% | 60% | 60% | 60% | 0.88 |
| COMPOUND (I-1-1)/(I-1-7) @ 0.25 mg ai/seed + Axmi205 | Positive 12 plants | 0% | 40% | 40% | 40% | 0.75 |
| COMPOUND (I-1-1)/(I-1-7) @ 0.5 mg ai/seed | Negative 18 plants | 13% | 53% | 57% | 60% | 0.79 |
| COMPOUND (I-1-1)/(I-1-7) @ 0.5 + Axmi205 mg ai/seed | Positive 12 plants | 7% | 40% | 40% | 40% | 0.54 |

*Root Damage Rating 0 = undamaged; 3 = severely damaged
**UTC = untreated control; plants were infested with WCRW but not treated with compound (I-1-1)/(I-1-7)

Example 3

*Nezara viridula* on Transgenic Soybean (*Glycine max*)

| | |
|---|---|
| Solvent: | 7 parts by weight of dimethylformamide |
| Emulsifier: | 2 parts by weight of alkylaryl polyglycolether |

To produce a suitable preparation of active compound, 1 part by weight of active compound is mixed with the stated amount of solvent and emulsifier, and the concentrate is diluted with emulsifier-containing water to the desired concentration.

Seeds of the transgenic *Glycine max* line MON89788 deposited at the American Type Culture Collection (ATCC) were obtained under the number ATCC-PTA-6708 from LGC Standards GmbH, Mercatorstr. 51, 46485 Wesel, Germany. The MON89788 line is described in the US patent application US 2006/0282915 and contains a Glyphosate tolerance mediating 5-enol-pyruvyl shikimate-3-phosphate synthase gene derived from *Agrobacterium* sp. Strain CP4 (CP4 EPSPS).

The Glyphosate tolerance of plants was confirmed by dipping a leaf into Roundup® UltraMax (Monsanto) solution (0.75%).

Single potted non-transgenic and transgenic soybean plants are treated in 2 replicates by being sprayed with the preparation of the active compound of the desired concentration and infested with larvae of the southern green stink bug (*Nezara viridula*).

After the specified period of time, the mortality in % is determined. 100% means that all the larvae have been killed; 0% means that none of the larvae have been killed.

The results obtained were compared to the results of the compound on non-transgenic soybean plants and the results of the non-treated transgenic soybean plants.

TABLE 3

*Nezara viridula* on soybean (*Glycine max*)

| Active Compound | Concentration in ppm | Mortality in % after 2 d | |
|---|---|---|---|
| Compound (I-1-1)/(I-1-7) on non-transgenic soybean | 20 | 17 | |
| MON89788 soybean | — | 0 | |
| | | obs* | cal.** |
| Compound (I-1-1)/(I-1-7) on MON89788 soybean According to the invention | 20 | 50 | 17 |

*obs. = observed insecticidal efficacy,
**cal. = efficacy calculated with Colby-formula

Example 4

*Spodoptera frugiperda* on Transgenic Maize (*Zea mays*)

| | |
|---|---|
| Solvent: | 7 parts by weight of dimethylformamide |
| Emulsifier: | 2 parts by weight of alkylaryl polyglycolether |

To produce a suitable preparation of active compound, 1 part by weight of active compound is mixed with the stated amount of solvent and emulsifier, and the concentrate is diluted with emulsifier-containing water to the desired concentration.

Seeds of the transgenic *Zea mays* line GA21 deposited at the American Type Culture Collection (ATCC) were obtained under the number ATCC-209033 from LGC Standards GmbH, Mercatorstr. 51, 46485 Wesel, Germany. The Ga21 line is described in the U.S. Pat. No. 6,040,497 and contains a modified 5-enol-pyruvyl shikimate-3-phosphate synthase gene (mEPSPS) of *Zea mays* conferring glyphosate tolerance. The Glyphosate tolerance of plants was confirmed by dipping a leaf into Roundup® UltraMax (Monsanto) solution (0.75%).

Single potted non-transgenic or transgenic maize plants are treated in 2 replicates by being sprayed with the preparation of the active compound of the desired concentration and are infested with caterpillars of the fall army worm (*Spodoptera frugiperda*).

After the specified period of time, the mortality in % is determined. 100% means that all the caterpillars have been killed; 0% means that none of the caterpillars have been killed.

The results obtained were compared to the results of the compound on non-transgenic maize plants and the results of the non-treated transgenic maize plants.

TABLE 4

*Spodoptera frugiperda* on maize

| Active Compound | Concentration in ppm | Mortality in % after 3 d | |
|---|---|---|---|
| Compound (I-1-1)/(I-1-7) on non-transgenic maize | 0.16 | 80 | |
| GA21 maize (mEPSPS) | — | 10 | |
| | | obs* | cal.** |
| Compound (I-1-1)/(I-1-7) on GA21 maize According to the invention | 0.16 | 100 | 82 |

*obs. = observed insecticidal efficacy,
**cal. = efficacy calculated with Colby-formula

The invention claimed is:

1. A method for controlling insects, and/or acarids and/or nematodes comprising applying a mixture of compounds 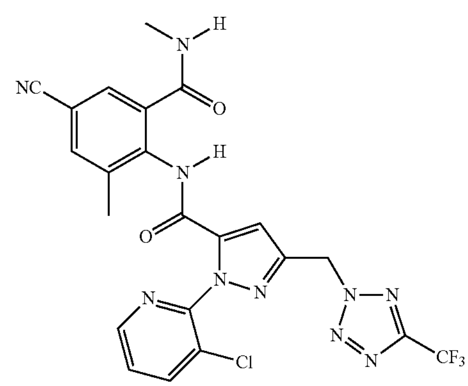 and wherein the compounds may also be present as an N-oxide and/or salt thereof, on one or more transgenic crops.

2. A method for controlling insects and/or acarids and/or nematodes according to claim 1, comprising applying a composition comprising A) the mixture of compounds and B) one or more additional agrochemically active compounds.

3. The method according to claim 1, wherein the compounds are at a rate of 5 g to 5 kg per ha.

4. The method for controlling insects, and/or acarids and/or nematodes according to claim 1, comprising applying the compounds on seeds of one or more transgenic crops.

5. The method of for controlling insects, and/or acarids and/or nematodes according to claim 1, comprising applying the compounds to one or more of transgenic corn, soybean, cotton, rice, oilseed rape, sugar cane, sugar beet, potatoes, vegetables, tomatoes, curcurbits, tobacco, coffee, and fruits.

6. The method according to claim 1, which increases yield.

7. The method according to claim 1, wherein the crop is transgenic corn.

8. The method according to claim 1, wherein the crop is transgenic soybean.

9. The method according to claim 1, wherein the crop is transgenic rice.

* * * * *